US007196059B2

(12) United States Patent
Soltero et al.

(10) Patent No.: US 7,196,059 B2
(45) Date of Patent: *Mar. 27, 2007

(54) PHARMACEUTICAL COMPOSITIONS OF INSULIN DRUG-OLIGOMER CONJUGATES AND METHODS OF TREATING DISEASES THEREWITH

(75) Inventors: Richard Soltero, Holly Springs, NC (US); Balasingam Radhakrishnan, Chapel Hill, NC (US); Nnochiri N. Ekwuribe, Cary, NC (US); Bruce Rehlaender, Chapel Hill, NC (US); Anthony Hickey, Chapel Hill, NC (US); Li Li Bovet, Chapel Hill, NC (US)

(73) Assignee: Biocon Limited, Bangalore (IN)

( * ) Notice: Subject to any disclaimer, the term of this patent is extended or adjusted under 35 U.S.C. 154(b) by 0 days.

This patent is subject to a terminal disclaimer.

(21) Appl. No.: 10/382,155

(22) Filed: Mar. 5, 2003

(65) Prior Publication Data

US 2004/0038866 A1 Feb. 26, 2004

Related U.S. Application Data

(63) Continuation-in-part of application No. 10/235,284, filed on Sep. 5, 2002, now Pat. No. 6,770,625, and a continuation-in-part of application No. 10/235,381, filed on Sep. 5, 2002, now Pat. No. 6,867,183.

(60) Provisional application No. 60/377,865, filed on May 3, 2002, provisional application No. 60/318,193, filed on Sep. 7, 2001.

(51) Int. Cl.
*A61K 38/28* (2006.01)
*C07K 14/62* (2006.01)
(52) U.S. Cl. .............................. 514/3; 514/784; 530/303

(58) Field of Classification Search .................... 514/3, 514/4, 784, 808; 424/450; 530/303, 304, 530/305, 345
See application file for complete search history.

(56) References Cited

U.S. PATENT DOCUMENTS 3,256,153 A 6/1966 Heimlech .................... 424/497

(Continued)

FOREIGN PATENT DOCUMENTS

DE 196 32 440 A1 2/1998

(Continued)

OTHER PUBLICATIONS

Agarwal et al. "Polymethyacrylate-based Microparticulates of Insulin for Oral Delivery: Preparation and In Vitro Dissolution Stability in the Presence of Enzyme Inhibitors" *International Journal of Pharmaceutics* 225:31-39 (2001).

(Continued)

*Primary Examiner*—Jeffrey Edwin Russel
(74) *Attorney, Agent, or Firm*—Marianne Fuierer; William A. Barrett; Moore & Van Allen PLLC

(57) ABSTRACT

Pharmaceutical compositions that include insulin, an insulin drug-oligomer conjugate, a fatty acid component, and a bile salt component or a bile salt component without a fatty acid component are described. The insulin drug is covalently coupled to an oligomeric moiety. The fatty acid component and the bile salt component, when together, can be present in a weight-to-weight ratio of between 1:15 and 15:1. Methods of treating an insulin deficiency in a subject in need of such treatment using such pharmaceutical compositions are also provided, as are methods of providing such pharmaceutical compositions.

34 Claims, 15 Drawing Sheets

U.S. PATENT DOCUMENTS

| | | | |
|---|---|---|---|
| 3,868,356 A | 2/1975 | Smyth | 530/303 |
| 3,919,411 A | 11/1975 | Glass et al. | 424/78.27 |
| 3,950,517 A | 4/1976 | Lindsay et al. | 514/3 |
| 4,003,792 A | 1/1977 | Mill et al. | 530/303 |
| 4,044,196 A | 8/1977 | Huper et al. | 526/271 |
| 4,087,390 A | 5/1978 | Shields | 525/54.11 |
| 4,093,574 A | 6/1978 | Shields | 525/54.11 |
| 4,100,117 A | 7/1978 | Shields | 525/54.11 |
| 4,156,719 A | 5/1979 | Sezaki et al. | 424/118 |
| 4,179,337 A | 12/1979 | Davis et al. | 435/181 |
| 4,223,163 A | 9/1980 | Guilloty | 568/618 |
| 4,229,438 A | 10/1980 | Fujino et al. | 514/15 |
| 4,253,998 A | 3/1981 | Sarantakis | 525/54.11 |
| 4,277,394 A | 7/1981 | Fujino et al. | 530/330 |
| 4,338,306 A | 7/1982 | Kitao et al. | 514/4 |
| 4,348,387 A | 9/1982 | Brownlee et al. | 514/4 |
| 4,410,547 A | 10/1983 | Ueno et al. | 514/557 |
| 4,469,681 A | 9/1984 | Brownlee et al. | 514/4 |
| 4,472,382 A | 9/1984 | Labrie et al. | 514/15 |
| 4,554,101 A | 11/1985 | Hopp | 514/17 |
| 4,579,730 A | 4/1986 | Kidron et al. | 514/3 |
| 4,585,754 A | 4/1986 | Meisner et al. | 514/8 |
| 4,602,043 A | 7/1986 | Geho | 514/646 |
| 4,622,392 A | 11/1986 | Hong et al. | 536/29 |
| 4,662,872 A | 5/1987 | Cane | 604/151 |
| 4,684,524 A | 8/1987 | Eckenhoff et al. | 424/469 |
| 4,698,264 A | 10/1987 | Steinke | 428/402.2 |
| 4,704,394 A | 11/1987 | Geho | 514/288 |
| 4,717,566 A | 1/1988 | Eckenhoff et al. | 424/438 |
| 4,744,976 A | 5/1988 | Snipes et al. | 424/408 |
| 4,761,287 A | 8/1988 | Geho | 424/450 |
| 4,772,471 A | 9/1988 | Vanlerberghe et al. | 424/450 |
| 4,797,288 A | 1/1989 | Sharma et al. | 424/476 |
| 4,801,575 A | 1/1989 | Pardridge | 514/4 |
| 4,822,337 A | 4/1989 | Newhouse et al. | 604/50 |
| 4,839,341 A | 6/1989 | Massey et al. | 514/4 |
| 4,840,799 A | 6/1989 | Applegren et al. | 424/493 |
| 4,849,405 A | 7/1989 | Ecanow | 514/3 |
| 4,863,896 A | 9/1989 | Geho et al. | 514/4 |
| 4,917,888 A | 4/1990 | Katre et al. | 424/85.91 |
| 4,935,246 A | 6/1990 | Ahrens | 424/490 |
| 4,946,828 A | 8/1990 | Markussen | 514/3 |
| 4,957,910 A | 9/1990 | Sutton et al. | 514/185 |
| 4,963,367 A | 10/1990 | Ecanow | 424/485 |
| 4,963,526 A | 10/1990 | Ecanow | 514/3 |
| 4,994,439 A | 2/1991 | Longenecker et al. | 514/3 |
| 5,013,556 A | 5/1991 | Woodle et al. | 424/450 |
| 5,055,300 A | 10/1991 | Gupta | 424/409 |
| 5,055,304 A | 10/1991 | Makino et al. | 424/465 |
| 5,089,261 A | 2/1992 | Nitecki et al. | 424/85.2 |
| 5,093,198 A | 3/1992 | Speaker et al. | 428/402.21 |
| 5,099,074 A | 3/1992 | Meuller et al. | 568/617 |
| 5,122,614 A | 6/1992 | Zalipsky | 548/520 |
| 5,157,021 A | 10/1992 | Balschmidt et al. | 514/3 |
| 5,162,430 A | 11/1992 | Rhee et al. | 525/54.1 |
| 5,164,366 A | 11/1992 | Balschmidt et al. | 514/3 |
| 5,202,415 A | 4/1993 | Jonassen et al. | 530/303 |
| 5,206,219 A | 4/1993 | Desai | 514/3 |
| 5,283,236 A | 2/1994 | Chiou | 514/2 |
| 5,286,637 A | 2/1994 | Veronese et al. | 435/183 |
| 5,292,802 A | 3/1994 | Rhee et al. | 525/54.1 |
| 5,298,410 A | 3/1994 | Phillips et al. | 435/188 |
| 5,304,473 A | 4/1994 | Belagaje et al. | 435/69.7 |
| 5,308,889 A | 5/1994 | Rhee et al. | 525/54.1 |
| 5,312,808 A | 5/1994 | Shorr et al. | 514/6 |
| 5,320,094 A | 6/1994 | Laube et al. | 128/203.12 |
| 5,320,840 A | 6/1994 | Camble et al. | 424/85.1 |
| 5,321,009 A | 6/1994 | Baeder et al. | 514/4 |
| 5,324,775 A | 6/1994 | Rhee et al. | 525/54.2 |
| 5,328,955 A | 7/1994 | Rhee et al. | 525/54.1 |
| 5,349,052 A | 9/1994 | Delgado et al. | 530/351 |
| 5,359,030 A | 10/1994 | Ekwuribe | 530/303 |
| 5,364,838 A | 11/1994 | Rubsamen | 514/3 |
| 5,405,621 A | 4/1995 | Sipos | 424/490 |
| 5,405,877 A | 4/1995 | Greenwald et al. | 514/772.3 |
| 5,413,791 A | 5/1995 | Rhee et al. | 424/422 |
| 5,415,872 A | 5/1995 | Sipos | 424/490 |
| 5,420,108 A | 5/1995 | Shohet | 514/3 |
| 5,428,128 A | 6/1995 | Mensi-Fattohi et al. | 530/302 |
| 5,438,040 A | 8/1995 | Ekwuribe | 514/3 |
| 5,444,041 A | 8/1995 | Owen et al. | 514/2 |
| 5,446,091 A | 8/1995 | Rhee et al. | 525/54.1 |
| 5,457,066 A | 10/1995 | Frank et al. | 435/68.1 |
| 5,461,031 A | 10/1995 | De Felippis | 514/4 |
| 5,468,478 A | 11/1995 | Saifer et al. | 424/78.27 |
| 5,468,727 A | 11/1995 | Phillips et al. | 514/12 |
| 5,504,188 A | 4/1996 | Baker et al. | 530/304 |
| 5,506,203 A | 4/1996 | Bäckström et al. | 514/4 |
| 5,518,998 A | 5/1996 | Bäckström et al. | 514/3 |
| 5,523,348 A | 6/1996 | Rhee et al. | 525/54.1 |
| 5,529,915 A | 6/1996 | Phillips et al. | 435/188 |
| 5,545,618 A | 8/1996 | Buckley et al. | 514/12 |
| 5,550,188 A | 8/1996 | Rhee et al. | 525/54.1 |
| 5,567,422 A | 10/1996 | Greenwald | 424/78.3 |
| 5,579,797 A | 12/1996 | Rogers | 135/90 |
| 5,606,038 A | 2/1997 | Regen | 536/6.5 |
| 5,612,460 A | 3/1997 | Zalipsky | 530/391.9 |
| 5,631,347 A | 5/1997 | Baker et al. | 530/303 |
| 5,637,749 A | 6/1997 | Greenwald | 558/6 |
| 5,643,575 A | 7/1997 | Martinez et al. | 424/194.1 |
| 5,646,242 A | 7/1997 | Baker et al. | 530/303 |
| 5,650,388 A | 7/1997 | Shorr et al. | 514/6 |
| 5,658,878 A | 8/1997 | Bäckström et al. | 514/3 |
| 5,681,567 A | 10/1997 | Martinez et al. | 424/178.1 |
| 5,681,811 A | 10/1997 | Ekwuribe | 514/8 |
| 5,693,609 A | 12/1997 | Baker et al. | 514/3 |
| 5,693,769 A | 12/1997 | Kahne et al. | 536/5 |
| 5,700,904 A | 12/1997 | Baker et al. | 530/305 |
| 5,704,910 A | 1/1998 | Humes | 604/52 |
| 5,707,648 A | 1/1998 | Yiv | 424/450 |
| 5,714,519 A | 2/1998 | Cincotta et al. | 514/616 |
| 5,714,639 A | 2/1998 | Bowman et al. | 568/620 |
| 5,738,846 A | 4/1998 | Greenwald et al. | 424/85.7 |
| 5,747,445 A | 5/1998 | Bäckström et al. | 514/4 |
| 5,747,642 A | 5/1998 | De Felippis | 530/304 |
| 5,750,497 A | 5/1998 | Havelund et al. | 514/3 |
| 5,763,396 A | 6/1998 | Weiner et al. | 514/3 |
| 5,766,620 A | 6/1998 | Heiber et al. | 424/436 |
| 5,824,638 A | 10/1998 | Burnside et al. | 514/3 |
| 5,830,853 A | 11/1998 | Bäckström et al. | 514/4 |
| 5,830,918 A | 11/1998 | Sportsman et al. | 514/648 |
| 5,843,886 A | 12/1998 | Weiner et al. | 514/3 |
| 5,849,860 A | 12/1998 | Hakimi et al. | 528/370 |
| 5,853,748 A | 12/1998 | New | 424/439 |
| 5,854,208 A | 12/1998 | Jones et al. | 514/3 |
| 5,856,451 A | 1/1999 | Olsen et al. | 530/402 |
| 5,866,538 A | 2/1999 | Norup et al. | 514/3 |
| 5,866,584 A | 2/1999 | Cincotta et al. | 514/288 |
| 5,874,111 A | 2/1999 | Maitra et al. | 424/499 |
| 5,889,153 A | 3/1999 | Suzuki et al. | 530/350 |
| 5,898,028 A | 4/1999 | Jensen et al. | 514/4 |
| 5,902,588 A | 5/1999 | Greenwald et al. | 424/278.1 |
| 5,905,140 A | 5/1999 | Hansen | 530/303 |
| 5,907,030 A | 5/1999 | Shen et al. | 530/331 |
| 5,922,675 A | 7/1999 | Baker et al. | 514/4 |
| 5,932,462 A | 8/1999 | Harris et al. | 435/188 |
| 5,942,248 A | 8/1999 | Barnwell | 424/457 |
| 5,948,751 A | 9/1999 | Kimer et al. | 514/4 |
| 5,952,008 A | 9/1999 | Bäckström et al. | 424/499 |
| 5,952,297 A | 9/1999 | De Felippis et al. | 514/3 |
| 5,962,267 A | 10/1999 | Shin et al. | 435/69.4 |
| 5,968,549 A | 10/1999 | New et al. | 424/450 |
| 5,969,040 A | 10/1999 | Hallahan et al. | 525/54.1 |
| 5,981,709 A | 11/1999 | Greenwald et al. | 530/351 |

| | | | |
|---|---|---|---|
| 5,985,263 A | 11/1999 | Lee et al. | 424/85.2 |
| 5,997,848 A | 12/1999 | Patton et al. | 424/46 |
| 6,004,574 A | 12/1999 | Bäckström et al. | 424/434 |
| 6,011,008 A | 1/2000 | Domb et al. | 514/8 |
| 6,025,325 A | 2/2000 | Campfield et al. | 514/2 |
| 6,034,054 A | 3/2000 | De Felippis et al. | 514/4 |
| 6,042,822 A | 3/2000 | Gilbert et al. | 424/85.7 |
| 6,043,214 A | 3/2000 | Jensen et al. | 514/3 |
| 6,051,551 A | 4/2000 | Hughes et al. | 514/3 |
| 6,057,292 A | 5/2000 | Cunningham et al. | 514/12 |
| 6,063,761 A | 5/2000 | Jones et al. | 514/3 |
| 6,093,391 A | 7/2000 | Kabanov et al. | 424/85.1 |
| 6,113,906 A | 9/2000 | Greenwald et al. | 424/194.1 |
| 6,147,108 A | 11/2000 | Hauptman | 514/449 |
| 6,165,976 A | 12/2000 | Bäckström et al. | 514/3 |
| 6,177,087 B1 | 1/2001 | Greenwald et al. | 424/278.1 |
| 6,191,105 B1 | 2/2001 | Ekwuribe et al. | 514/3 |
| 6,200,602 B1 | 3/2001 | Watts et al. | 424/463 |
| 6,211,144 B1 | 4/2001 | Havelund | 514/4 |
| 6,248,363 B1 | 6/2001 | Patel et al. | 424/497 |
| 6,251,856 B1 | 6/2001 | Markussen et al. | 514/3 |
| 6,255,502 B1 | 7/2001 | Penkler et al. | 552/549 |
| 6,258,377 B1 | 7/2001 | New et al. | 424/450 |
| 6,268,335 B1 | 7/2001 | Brader | 514/3 |
| 6,306,440 B1 | 10/2001 | Bäckström et al. | 424/499 |
| 6,309,663 B1 | 10/2001 | Patel et al. | 424/450 |
| 6,310,038 B1 | 10/2001 | Havelund | 514/4 |
| 6,323,311 B1 | 11/2001 | Liu et al. | 530/303 |
| 6,335,316 B1 | 1/2002 | Hughes et al. | 514/3 |
| 6,342,225 B1 | 1/2002 | Jones et al. | 424/193.1 |
| 6,368,629 B1 * | 4/2002 | Watanabe et al. | 424/482 |
| 6,506,730 B1 | 1/2003 | Lee et al. | 514/12 |
| 6,770,625 B2 * | 8/2004 | Soltero et al. | 514/12 |
| 2002/0018811 A1 | 2/2002 | Penteado et al. | 424/474 |
| 2002/0160938 A1 | 10/2002 | Brandenberg et al. | 514/3 |
| 2003/0004304 A1 | 1/2003 | Ekwuribe et al. | 528/425 |
| 2003/0027748 A1 | 2/2003 | Ekwuribe et al. | 514/3 |
| 2003/0027995 A1 | 2/2003 | Ekwuribe et al. | 530/399 |
| 2003/0050228 A1 | 3/2003 | Ekwuribe et al. | 514/3 |
| 2003/0060606 A1 | 3/2003 | Ekwuribe et al. | 530/399 |
| 2003/0069170 A1 | 4/2003 | Soltero et al. | 514/2 |
| 2003/0083232 A1 | 5/2003 | Soltero et al. | 514/3 |
| 2003/0087808 A1 | 5/2003 | Soltero et al. | 514/3 |
| 2003/0144468 A1 | 7/2003 | Ekwuribe et al. | 528/425 |
| 2003/0166508 A1 * | 9/2003 | Zhang | 514/3 |

FOREIGN PATENT DOCUMENTS

| | | |
|---|---|---|
| EP | 0 031 567 | 7/1981 |
| EP | 0511903 | 4/1992 |
| EP | 0483465 B1 | 5/1992 |
| EP | 0 483 465 | 8/1995 |
| EP | 0 597 007 | 10/1996 |
| EP | 0 621 777 | 11/1996 |
| EP | 0 822 218 A2 | 2/1998 |
| EP | 0 797 615 | 1/1999 |
| GB | 1 492 997 | 11/1977 |
| JP | 52057313 A | 5/1977 |
| JP | 01207320 | 8/1989 |
| JP | 1 254 699 | 10/1989 |
| WO | WO 93/01802 | 2/1993 |
| WO | WO 95/09831 | 4/1995 |
| WO | WO 95/30641 | 11/1995 |
| WO | WO 98/07745 | 2/1998 |
| WO | WO 99/32134 | 7/1999 |
| WO | WO 99/65941 | 12/1999 |
| WO | WO 00/078302 A1 | 12/2000 |
| WO | WO 01/12230 | 2/2001 |
| WO | WO 02/20037 A1 * | 3/2002 |

OTHER PUBLICATIONS

Allaudeen et al. "Orally Active Insulin: A Single Insulin Conjugate Selected for Future Studies" 60th Annual Meeting of the American Diabetes Assoc., Atlanta, GA, Jun. 2000 (Abstract).

Anderson et al. "HIM2, a Novel Modified Insulin, has Improved Systemic Pharmacokinetics in Normal Dogs, Compared to Unmodified Insulin" American Diabetes Association 62nd Annual Meeting, Jun. 2002 (Abstract).

Aoki et al. "Chronic Intermittent Intravenous Insulin Therapy: A New Frontier in Diabetes Therapy" *Diabetes Technology & Therapeutics* 3(1):111-123 (2001).

Block, Lawrence H. "Pharmaceutical Emulsions and Microemulsions" *Pharmaceutical Dosage Forms: Disperse Systems* vol. 2, Ed. Lieberman et al., pp. 47-109 (1996).

Bone et al. "Successful Treatment of an Insulin Dependent Rat Model of Human Type I Diabetes with Orally Active Insulin" Program and Abstracts, 4th International Workshop on Lessons from Animal Diabetes, Omiva, Japan, Nov. 1994 (Abstract).

Bone et al. "Successful Treatment of Type 1 Diabetes with Orally-Active Insulin: Studies in The Insulin Dependent BB/S Rat" Program and Abstracts, 55th Annual Meeting of the American Diabetes Association, Atlanta Georgia, Jun. 1995 (Abstract).

Brange and Volund "Insulin Analogs with Improved Pharmacokinetic Profiles" *Advanced Drug Delivery Reviews* 35:307-335 (1999).

Cleland et al. "Emerging Protein Delivery Methods". *Current Opinion in Biotechnology* 12:212-219 (2001).

Clement et al. "Effects of Multiple Doses of Orally Administered Hexyl Insulin M2 (HIM2) on Postprandial Blood Glucose (PPG) Concentrations in Type 1 Diabetic (T1) Patients" American Diabetes Association 62nd Annual Meeting, Jun. 2002 (Poster).

Clement et al. "Oral Insulin Product Hexyl-Insulin Monoconjugate 2 (HIM2) in Type 1 Diabetes Mellitus: The Glucose Stabilization Effects of HIM2" *Diabetes Technology & Therapeutics* 4(4):459-466 (2002).

Clement, Stephen "A Dose-Escalation Study of the Effects of Two Sequential Doses of Oral Modified Insulin on Blood Glucose Concentrations in Patients with Type 1 Diabetes Mellitus" American Diabetes Association Annual Meeting (Jun. 25, 2001) (Abstract).

Clement, Stephen "A Dose-Escalation Study of the Effects of Two Sequential Doses of Oral Modified Insulin on Blood Glucose Concentrations in Patients with Type 1 Diabetes Mellitus" American Diabetes Association Annual Meeting (Jun. 25, 2001) (Poster).

Damge et al. "Poly(alkyl cyanoacrylate) Nanospheres for Oral Administration of Insulin" *Journal of Pharmaceutical Sciences* 86(12):1403-1409 (Dec. 1997).

Dandona et al. "Effect of an Oral Modified Insulin on Blood Glucose Levels in Fasting and Fed Type 1 Diabetic Patients Receiving a 'Basal' Regimen of Injected Insulin" American Diabetes Association Annual Meeting (Jun. 25, 2001) (Abstract).

Ekwuribe et al. "Oral Insulin Delivery: Hydrolyzable Amphiphilic Oligomer Conjugates Prolong Glucose Reduction" *Proceed. Int'l Symp. Control. Rel. Bioact. Mater*. 26:147-148 (1999).

Ekwuribe et al. *Calcitonin Drug-Oligomer Conjugates, and Uses Thereof*, U.S. Appl. No. 10/166,355, filed Nov. 8, 2002, including Preliminary Amendment dated Feb. 26, 2003 and Supplemental Preliminary Amendment dated Mar. 31, 2003.

Ekwuribe et al. *Mixtures of Drug-Oligomer Conjugates Comprising Polyalkylene Glycol, Uses Thereof, and Methods of Making Same*, U.S. Appl. No. 09/873,797, filed Jun. 4, 2001.

Ekwuribe, Nnochiri "Conjugation-Stabilized Polypeptide Compositions, Therapeutic Delivery and Diagnostic Formulations Comprising Same, and Method of Making and Using the Same" *Biotechnology Advances* 14(4):575-576 (1996) (Abstract).

Francis et al. "Polyethylene Glycol Modification: Relevance of Improved Methodology to Tumour Targeting" Journal of Drug Targeting 3:321-340 (1996).

Guzman et al. "Effects of Fatty Ethers and Stearic Acid on the Gastrointestinal Absorption of Insulin" *PRHSJ* 9(2):155-159 (1990).

Harris, J. Milton "Laboratory Synthesis of Polyethylene Glycol Derivatives" *J. Macromol. Science—Rev. Macromol. Chem. Phys.* C25(3):325-373 (1985).

Hinds et al. "Synthesis and Characterization of Poly(ethylene glycol)-Insulin Conjugates" *Bioconjugate Chem.* 11:195-201 (2000).

Hosny et al. "Promotion of Oral Insulin Absorption in Diabetic Rabbits Using pH-Dependent Coated Capsules Containing Sodium Cholate" *Pharmaceutica Acta Helvetiae* 72:203-207 (1997).

Kipnes et al. "Control of Postprandial Plasma Glucose by an Oral Insulin Product (HIM2) in Patients with Type 2 Diabetes" *Emerging Treatments and Technologies* 26:2 (2003).

Kipnes et al. "The Effects of an Oral Modified Insulin on Postprandial Blood Glucose Levels in Patients with Type 2 Diabetes" American Diabetes Association Annual Meeting (Jun. 24, 2001) (Abstract).

Kipnes et al. "The Effects of an Oral Modified Insulin on Postprandial Blood Glucose Levels in Patients with Type 2 Diabetes Mellitus" American Diabetes Association Annual Meeting (Jun. 2001) (Poster).

Kube, D.M. "Multitalented Proteins Play a Key Role in Therapeutics" *Genomics and Proteomics* (Sep. 2002).

Marschutz et al. "Oral Peptide Drug Delivery: Polymer-Inhibitor Conjugates Protecting Insulin from Enzymatic Degradation In Vitro" *Biomaterials* 21:1499-1507 (2000).

Mesiha et al. "Hypoglycaemic effect of oral insulin preparations containing Brij 35, 52, 58 or 92 and stearic acid" *J. Pharm. Pharmacol.* 33:733-734 (1981).

Michael et al. "Loss of Insulin Signaling in Hepatocytes Leads to Severe Insulin Resistance and Progressive Hepatic Dysfunction" *Molecular Cell* 6:87-97 (1999).

Moghaddam, Amir "Use of polyethylene glycol polymers for bioconjugations and drug development" *American Biotechnology Laboratory* pp. 42, 44 (Jul. 2001).

Musabayane et al. "Orally Administered, Insulin-Loaded Amidated Pectin Hydrogel Beads Sustain Plasma Concentrations of Insulin in Streptozotocin-Diabetic Rats" *Journal of Endocrinology* 164:1-6 (2000).

Neubauer et al. "Influence of Polyethylene Glycol Insulin on Lipid Tissues of Experimental Animals" *Diabetes* 32:953-958 (Oct. 1983).

Pang, David C. "Bridging Gaps in Drug Discovery and Development" *Pharmaceutical Technology* 22:82-94 (Nov. 1998).

Pauletti et al. "Improvement of Oral Peptide Bioavailability: Peptidomimetics and Prodrug Strategies" *Advanced Drug Delivery Reviews* 27:235-256 (1997).

Puskas et al. "Investigation of Chymotrypsin Digestion Profile of Orally Active Insulin Conjugate HIM2" Program and Abstracts, 2001 Annual Meeting & Exposition, Amer. Assoc. Pharm. Sci., Denver, CO, Oct. 2001 (Abstract).

Radhakrishnan et al. "Chemical Modification of Insulin with Amphiphilic Polymers Improves Intestinal Delivery," Proceed. Intl. Symp. Control. Rel. Bioact. Mater. 25:124-125 (1998).

Radhakrishnan et al. "Oral Delivery of Insulin: Single Selective Modification at B29-LYS With Amphiphilic Oligomer" Program and Abstracts, 1999 National Meeting of the Ameri. Assoc. Pharm. Scient., New Orleans, LA (1999) (Abstract).

Rhadhakrishnan et al., Stability and Physical Characteristics of Orally Active Amphiphilic Human Insulin Analog, Methoxy (Polyethylene Glycol) Hexanoyl Human Recombinant Insulin (HIM2) *Proceed. Int'l Symp Control Rel. Bioact. Mater*, vol. 27 pp. 1038-1039 (2000).

Radhakrishnan et al. "Structure-Activity Relationship of Insulin Modified with Amphiphilic Polymers" Program and Abstracts, 1998 National Meeting of the Amer. Assoc. Pharm. Scient., San Francisco, CA Pharm. Sci. 1(1):S-59 (1998) (Abstract).

Radhakrishnan et al., *Insulin Polypeptide-Oligomer Conjugates, Proinsulin Polypeptide-Oligomer Conjugates and Methods of Synthesizing Same*, U.S. Appl. No. 10/389,499, filed Mar. 17, 2003.

Richards et al. "Self-Association Properties of Monomeric Insulin Analogs Under Formulation Conditions" *Pharmaceutical Research* 15(9):1434-1441 (1998).

Scott-Moncrieff et al. "Enhancement of Intestinal Insulin Absorption by Bile Salt-Fatty Acid Mixed Micelles in Dogs" Journal of Pharmaceutical Sciences 83(10):1465-1469 (1994).

Shah and Shen "Transcellular Delivery of an Insulin-Transferrin Conjugate in Enterocyte-like Caco-2 Cells" *Journal of Pharmaceutical Sciences* 85(12):1306-1311 (1996).

Shen et al. "(C) Means to Enhance Penetration; (3) Enhancement of polypeptide and protein absorption by macromolecular carriers via endocytosis and transcytosis" *Advanced Drug Del. Reviews* 8:93-113 (1992).

Sindelar et al. "A Comparison of the Effects of Selective Increases in Peripheral or Portal Insulin on Hepatic Glucose Production in the Conscious Dog" *Diabetes* 45:1594-1604 (1996).

Sirokman et al. "Refolding and proton pumping activity of a polyethylene glycol-bacteriorhodopsin water-soluble conjugate" *Protein Science* 12:1161-1170 (1993).

Sluzky et al. "Kinetics of Insulin Aggregation in Aqueous Solutions Upon Agitation in the Presence of Hydrophobic Surfaces" *Proc. Natl. Acad. Sci.* 88:9377-9381 (Nov. 1991).

Soltero et al. *Insulin Polypeptide-Oligomer Conjugates, Proinsulin Polypeptide-Oligomer Conjugates and Methods of Synthesizing Same* U.S. Appl. No. 10/382,022, filed Mar. 5, 2003.

Soltero et al. *Pharmaceutical Compositions of Drug-Oligomer Conjugates and Methods of Treating Diseases Therewith* U.S. Appl. No. 10/382,069, filed Mar. 5, 2003.

Soltero et al. *Pharmaceutical Compositions of Insulin Drug-Oligomer Conjugates and Methods of Treating Diseases Therewith* U.S. Appl. No. 10/382,155, filed Mar. 5, 2003.

Song et al., "Direct Measurement of Pulsatile Insulin Secretion from the Portal Vein in Human Subjects" *Journal of Clinical Endocrinology & Metabolism* 85(12):4491-4499 (2000).

Still and McAllister "Effects of Orally Active Modified Insulin in Type 1 Diabetic Patients" *Clinical Pharmacol. Therap.* 69(2):P95 (Feb. 2001) (Abstract).

Still and McAllister "Effects of Orally Active Modified Insulin in Type 1 Diabetic Patients" Slide Presentation Annual Meeting of the American Society for Clinical Pharmacology & Therapeutics, Orlando, FL, Mar. 9, 2001.

Still and McAllister "Effects of Orally Active Modified Insulin in Type I Diabetic Patients" Annual Meeting of the American Society for Clinical Pharmacology & Therapeutics, Orlando, FL, Mar. 9, 2001 (Handout).

Still et al. "Magnitude and Variability of Pharmacokinetic and Glucodynamic Responses to Modified Human Insulin Administered Orally to Healthy Volunteers" *Diabetes Research and Clinical Practice* 56:S77 (2002) (Abstract).

Still et al., *Methods of Reducing Hypoglycemic Episodes in the Treatment of Diabetes Mellitus*, U.S. Appl. No. 10/461,199, filed Jun. 13, 2003.

Still, J. Gordon "Development of Oral Insulin: Progress and Current Status" *Diabetes/Metabolism Research and Reviews* 18(1):S29-S37 (2002).

Still, J. Gordon "Oral Insulin Development" Slide Presentation, VI International St. Barts Symposium Diabetes 2000: Therapy and Technology, London, England, May 12, 2000.

Stocklin et al. "A Stable Isotope Dilution Assay for the In Vivo Determination of Insulin Levels in Humans by Mass Spectrometry" *Diabetes* 46(1):1-7 (Jan. 1997).

Uchio et al. "Site-Specific Insulin Conjugates with Enhanced Stability and Extended Action Profile" *Advanced Drug Delivery Reviews* 35:289-306 (1999).

Vreeland et al. "Molar Mass Profiling of Synthetic Polymers by Free-Solution Capillary Electrophoresis of DNA-Polymer Conjugates" *Analytical Chemistry* 73(8):1795-1803 (2001).

Wei et al. "A Poly(Ethylene Glycol) Water-soluble Conjugate of Porin: Refolding to the Native State" *Biochemistry* 34:6408-6415 (1995).

Xia et al. "Effects of polyoxyethylene chain length distribution on the interfacial properties of polyethylene glycol n-dodecyl ether" *Yingyong Huaxue* 2(4): 59-65 (1985) (Abstract).

Zalipsky et al. "Peptide Attachment to Extremities of Liposomal Surface Grafted PEG Chains: Preparation of the Long-Circulating Form of Laminin Pentapeptide YIGSR" *Bioconjugate Chem.* 6:705-708 (1995).

Ziv and Bendayan "Intestinal Absorption of Peptides Through the Enterocytes" *Microscopy Research and Technique* 49:346-352 (2000).

International Search Report for International Application No. PCT/US02/28536 dated Sep. 15, 2003.

International Search Report for International Application No. PCT/US02//28429 dated Mar. 14, 2003.

Abuchowski, A. and F. F. Davis, "Soluble Polymer-Enzyme Adducts," pp. 368-383, Enzymes as Drugs, J. S. Holcenberg, John Wiley, 1981.

Akiyama, M. et al., "The Synthesis of New Derivatives of 1-.beta.-D-Arabinofuranosylcytosine," Chem. Pharm. Bull., 1978, 26(3): p. 981-984.

Allcock et al., "Contemporary Polymer Chemistry," 394-403 (2nd. ed., 1991).

Ansell, S. et al., "Application of Oligo-(14-amino-3,6,9,12-tetraoxatetradecanoic acid) Lipid Conjugates as Steric Barrier Molecules in Liposomal Formulations," Bioconjugate Chem., 10: 653-666 (1999).

Aoshima, M. et al., "N.sup.4 -Behenoyl-1-.beta.-D-Arabinofuranosylcytosine as a Potential New Antitumor Agent," Cancer Research, 1977, 37: pp. 2481-2486.

Baker, D. C. et al., "Prodrugs of 9-.beta.-D-Arabinofuranosyladenine. 1. Synthesis and Evaluation of Some 5'-(O-Acyl) Derivatives," J. Med. Chem., 1978, 21(12): pp. 1218-1221.

Banting et al., "Pancreatic Extracts in the Treatment of Diabetes Mellitus: Preliminary Report," Can. Med. Assoc. J., 145(10): 1281-1286 (1991).

Banting, R. G., et al, "Pancreatic Extracts in the Treatment of Diabetes Mellitus," The Canadian Med. Assoc. J. 1992, 12: 141-146.

Baudys et al., "Stabilization and Intestinal Absorption of Human Calcitonin," J. Contr. Rel. vol. 39, pp. 145-151 (1996).

Baudys, M. et al., "Synthesis and Characterization of Different Glycosylated Derivatives of Insulin" Proceed. Intern. Symp. Cont. Rel. Bioactive. Mater., 1992, 19: 210-211.

Boccu, E. et al., "Pharmacokinetic Properties of Polyethylene Glycol Derivatized Superoxide Dismutase," Pharm. Res. Comm., 1982 14: 113-120.

Brange, J., "Galenics of Insulin: The Physico-Chemical and Pharmaceutical Aspects of Insulin and Insulin Preparations," Novo Research Institute, Denmark, 18-100 (1987).

Brange, J. et al, "Chemical Stability of Insulin. 1. Hydrolytic Degradation During Storage of Pharmaceutical Preparations," Pharm. Res., 1992, 9 (6): 715-726.

Brange, J. et al, "Chemical Stability of Insulin. 2. Formation of Higher Molecular Weight Transformation Products During Storage of Pharmaceutical Preparations," Pharm. Res., 1992, 9 (6) 727-734.

Chen et al., "Synthesis and Properties of AMA Amphiphiles," J. Org. Chem., 64: 6870-6873 (1999).

Chien, Y. W., Novel Drug Delivery Systems, pp. 678-679, Marcell Deffer, Inc., New York, N.Y., 1992.

Conradi, R.A., et al., "The Influence of Peptide Structure on Transport Across Caco-2 Cells," Pharm. Res., 1991, 8(12): 1453-1459.

Coombes, A.G.A. et al., "Biodegradable Polymeric Microparticles for Drug Delivery and Vaccine Formulation: the Surface Attachment of Hydrophilic Species Using the Concept of Poly(Ethylene Glycol) Anchoring Segments," Biomaterials, 18: 1153-1161 (1997).

Coudert et al., "A Novel, Unequivocal Synthesis of Polyethylene Glycols," Synthetic Communications, 16(1): 19-26 (1986).

Delgado et al.; "The Uses and Properties of PEG-Linked Proteins" Critical Reviews in Therapeutic Drug Carrier Systems 9:3,4 249-304 (1992).

Engel et al.; "Insulin: Intestinal Absorption as Water-in-Oil-in-Water Emulsions" NATURE 219 856-857 (1968).

Fasano, Alessio; "Innovative strategies for the oral delivery of drugs and peptides" TIBTECH 16 152-157 (1998).

Forst et al., "New Aspects on Biological Activity of C-peptide in IDDM Patients," Exp. Clin. Endocrinol. Diabetes, 106: 270-276 (1998).

Gish, D. T. et al., "Nucleic Acids. 11. Synthesis of 5'-Esters of 1-.beta.-D-Arabinofuranosylcytosine Possessing Antileukemic and Immunosuppressive Activity," J. Med. Chem., 1971, 14(12): pp. 1159-1162.

Gombotz et al., "Biodegradable Polymers for Protein and Peptide Drug Delivery," Bioconjugate Chem., 6: 332-351 (1995).

Harris, J. Milton, "Laboratory Synthesis of Polyethylene Glycol Derivatives," J. Macromol. Science—Rev. Macromol. Chem. Phys., C25(3): 325-373 (1985).

Hashimoto et al., "Synthesis of Palmitoyl Derivatives of Insulin and Their Biological Activities," Pharmaceutical Research, 6(2): 171-176 (1989).

Hostetler, K. Y. et al., "Synthesis and Antiretroviral Activity of Phospholipid Analogs of Azidothymidine and Other Antiviral Nucleosides," The Journal of Biological Chemistry, 1990, 265(11): pp. 6112-6117.

Hong, C. I. et al., "Nucleoside Conjugates. 7. Synthesis and Antitumor Activity of 1-.beta.-D-Arabinofuranosylcytosine Conjugates of Ether Lipids," J. Med. Chem., 1986, 29: pp. 2038-2044.

Igarashi, R. et al, "Biologically Active Peptides Conjugated with Lecithin for DDS" Proceed. Intern. Symp. Cont. Rel. Bioactiv. Mater. 1990, 17 367-368.

Kemmler et al., "On the Nature and Subcellular Localization of the Proinsulin Converting Enzymes," Federation Proceedings, 30(Abstract 924): 1210Abs (1971).

Kemmler et al., "Studies on the Conversion of Proinsulin to Insulin: I. Converison in Vitro with Trypsin and Carboxypeptidase B," The Journal of Biological Chemistry, 246(22) 6786-6791 (Nov. 25, 1971).

King et al.; "Preparation of Protein Conjugates with Alkoxypolyethylene Glycols" Int. J. Peptide Protein Res. 16 147-155 (1980).

M. Maislos et al, "The Source of the Circulating Aggregate of Insulin in Type I Diabetic Patients is Therapeutic Insulin" J. Clin. Invest., 1986, 77: 717-723.

Nucci, et al. "The Therapeutic Value of Poly(ethylen Glycol)—Modified Proteins" Ac. Drug. Del. Rev. 6: 133-151 1991.

Oka, K. et al, "Enhanced Intestinal Absorption of a Hydrophobic Polymer-conjugated Protein Drug, Smancs, in an Oily Formulation" Pharm. Res., 1990, 7 (8): 852-855.

Patel et al. "Oral Administration of Insulin By Encapsulation Within Liposomes" FEBS Lett. 62(1) 60-63 1976.

Price, JC, *Polyethlyene Glycol*, 355-361, not dated.

Ratner, R. E. et al, "Persistent Cutaneous Insulin Allergy Resulting from High-Molecular Weight Insulin Aggregates," Diabetes, 1990, 39: 728-733.

Robbins, D. C. et al, "Antibodies to Covalent Aggregates of Insulin in Blood of Insulin-Using Diabetic Patients" Diabetes, 1987, 36: 838-841.

Russell-Jones, G. J. "Vitamin B12 Drug Delivery", Proceed. Intern. Symp. Control. Rel. Bioactive. Mater., 1992, 19: 102-103.

Saffran et al. "A Model for the Study of the Oral Administration of Peptide Hormones" Can J Biochem 57 548-553 1979.

Saffran, M. et al, "A New Approach to the Oral Administration of Insulin and Other Peptide Drugs," Science, 1986, 233: 1081-1084.

Santiago, N. et al, "Oral Immunization of Rats with Influenza Virus M Protein (M1) Microspheres," Proceed. Intern. Symp. Cont. Rel. Bioactive. Mater., 1992, 19: 116-117.

Savva et al., "Effect of PEG Homopolymer and Grafted Amphiphilic PEG-Palmityl on the Thermotropic Phase Behavior of 1,2-Dipalmitoyl-SN-Glycero-3-Phosphocholine Bilayer," Journal of Liposome Research, 9(3): 357-365 (1999).

Shichiri et al.; "Enteral Absorption of Water-in-Oil-in-Water Insulin Emulsions in Rabbits" Diabetologia 10 317-321 (1974).

Szleifer, I. et al., "Spontaneous Liposome Formation Induced by Grafted Poly(Ethylene Oxide) Layers: Theoretical Prediciton and Experimental Verification," Proceedings of the National Academy of Sciences of the United States of America, 95(3): 1032-1037 (Feb. 3, 1998).

Taniguchi, T. et al., "Synthesis of Acyloyl Lysozyme and Improvement of its Lymphatic Transport Following Small Intestinal Administration in Rats" Proceed. Intern. Symp. Control. Rel. Bioactiv. Mater., 1992, 19: 104-105.

Wahren et al., "Role of C-peptide in Human Physiology," Am. J. Physiol. Endocrinol. Metab., 278: E759-E768 (2000).

Tyle, Praveen, "Iontophoretic Devices for Drug Delivery," Pharma Research, 3:6 318-326 (1986).

Zalipsky, S. et al., "Attachment of Drugs to Polyethylene Glycols," Eur. Polym. J., 1983, 19(12): pp. 1177-1183.

* cited by examiner

PHARMACEUTICAL COMPOSITIONS OF INSULIN DRUG-OLIGOMER CONJUGATES AND METHODS OF TREATING DISEASES THEREWITH

RELATED APPLICATIONS

This application is a continuation-in-part application of U.S. application Ser. No. 10/235,284, filed Sep. 5, 2002, which now U.S. Pat. No. 6,770,625 to Soltero, and of U.S. application Ser. No. 10/235,381, filed Sep. 5, 2002, which is now U.S. Pat. No. 6,867,183 to Soltero, and which applications claim the benefit of U.S. Provisional Application No. 60/318,193, filed Sep. 7, 2001 and U.S. Provisional Application No. 60/377,865, filed May 3, 2002, the disclosures of each of which are incorporated herein by reference in their entireties.

FIELD OF THE INVENTION

The present invention relates to pharmaceutical compositions and methods of treating diseases therewith.

BACKGROUND OF THE INVENTION

The insulin polypeptide is the primary hormone responsible for controlling the transport, utilization and storage of glucose in the body. The β-cells of the pancreatic islets secrete a single chain precursor of insulin, known as proinsulin. Proteolysis of proinsulin results in removal of certain basic amino acids in the proinsulin chain along with the connecting peptide (C-peptide) to yield the biologically active polypeptide insulin.

The insulin molecule has been highly conserved in evolution and generally consists of two chains of amino acids linked by disulfide bonds. In the natural human, two-chain insulin molecule (mw 5,800 Daltons), the A-chain is composed of 21 amino acid residues and has glycine at the amino terminus and the B-chain has 30 amino acid residues and phenylalanine at the amino terminus.

Insulin can exist as a monomer or may aggregate into a dimer or a hexamer formed from three of the dimers. Biological activity, i.e., the ability to bind to receptors and stimulate the biological actions of insulin, resides in the monomer.

Diabetes is a biological disorder involving improper carbohydrate metabolism. Diabetes results from insufficient production of, or reduced sensitivity to, insulin. In persons with diabetes, the normal ability to use glucose is inhibited, leading to elevated blood sugar levels (hyperglycemia). As glucose accumulates in the blood, excess levels of sugar are excreted in the urine (glycosuria). Other symptoms of diabetes include increased urinary volume and frequency, thirst, itching, hunger, weight loss, and weakness.

There are two varieties of diabetes. Type I is insulin-dependent diabetes mellitus, or IDDM. IDDM was formerly referred to as "juvenile onset diabetes." In IDDM, insulin is not secreted by the pancreas and must be provided from an external source. Type II or adult-onset diabetes can ordinarily be controlled by diet, although in some advanced cases, administration of insulin is required.

Untreated diabetes leads to ketosis, the accumulation of ketones, which are products of fat breakdown, in the blood. Ketosis is followed by the accumulation of acid in the blood (acidosis), nausea and vomiting. As the toxic products of disordered carbohydrate and fat metabolism continue to build up, the patient goes into a diabetic coma, which leads to death. Before the isolation of insulin in the 1920s, most patients died within a short time after onset.

The use of insulin as a treatment for diabetes dates to 1922, when Banting et al. ("Pancreatic Extracts in the Treatment of Diabetes Mellitus," *Can. Med. Assoc. J.*, 12:141–146 (1922)) showed that the active extract from the pancreas had therapeutic effects in diabetic dogs. In that same year, treatment of a diabetic patient with pancreatic extracts resulted in a dramatic, life-saving clinical improvement.

Until recently, bovine and porcine insulin were used almost exclusively to treat diabetes in humans. Today, however, numerous variations in insulin between species are known. Each variation differs from natural human insulin in having amino acid substitution(s) at one or more positions in the A- and/or B-chain. Despite these differences, most mammalian insulin has comparable biological activity. The advent of recombinant technology has enabled commercial scale manufacture of human insulin (e.g., Humulin™ insulin, commercially available from Eli Lilly and Company, Indianapolis, Ind.) or genetically engineered insulin having biological activity comparable to natural human insulin.

Treatment of diabetes typically requires regular injections of insulin. Due to the inconvenience of insulin injections, various approaches have been attempted to formulate insulin for administration by non-injectable routes.

For example, U.S. Pat. No. 4,338,306 to Kitao et al. proposes pharmaceutical compositions for rectal administration of insulin. The pharmaceutical compositions include insulin and fatty acids having 8 to 14 carbon atoms and nontoxic salts thereof.

U.S. Pat. No. 4,579,730 to Kidron et al. proposes pharmaceutical compositions for the oral administration of insulin. The pharmaceutical compositions include insulin, a bile acid or alkali metal salt thereof, the bile acid being selected from the group consisting of cholic acid, chenodeoxycholic acid, taurocholic acid, taurochenodeoxycholic acid, glycocholic acid, glycochenocholic acid, 3β-hydroxy-12-ketocholic acid, 12α-3β-dihydrocholic acid, and ursodesoxycholic acid, and a protease inhibitor. The composition is provided with an enterocoating to assure passage through the stomach and release in the intestine.

U.S. Pat. No. 5,283,236 to Chiou proposes compositions for systemic delivery of insulin through the eyes where the drug passes into the nasolacrimal duct and becomes absorbed into circulation. The composition includes insulin and an enhancing agent. The enhancing agents proposed include, either alone or in combination, surfactants such as polyoxyethylene ethers of fatty acids and bile salts and acids such as cholic acid, deoxycholic acid, glycocholic acid, glycodeoxycholic acid, taurocholic acid, taurodeoxycholic acid, sodium cholate, sodium glycocholate, glycocholate, sodium deoxycholate, sodium taurodeoxycholate, chenodeoxycholic acid, and ursodeoxycholic acid. The enhancer is present in a concentration ranging from 0.1% to 5% (w/v).

U.S. Pat. No. 5,658,878 to Bäckström et al. proposes a therapeutic preparation for inhalation that includes insulin and a substance, which enhances the absorption of insulin in the lower respiratory tract. The enhancer can be a sodium salt of a saturated fatty acid of carbon chain length 10 (i.e., sodium caprate), 12 (sodium laurate), or 14 (sodium myristate). Potassium and lysine salts of capric acid are also proposed. Bäckström et al. note that if the carbon chain length is shorter than about 10, the surface activity of the surfactant may be too low, and if the chain length is longer than about 14, decreased solubility of the fatty acid in water limits its usefulness. As an alternative to the proposed fatty acid enhancers, Bäckström et al. propose the use of the following bile salts—sodium ursodeoxycholate, sodium taurocholate, sodium glycocholate, and sodium taurodihydrofusidate.

U.S. Pat. No. 5,853,748 to New proposes enteric-coated compositions for oral administration of insulin. The composition includes insulin, a bile salt or bile acid, and carbonate or bicarbonate ions, which are used to adjust the pH of the gut to a pH of from 7.5 to 9.

U.S. Pat. No. 6,200,602 to Watts et al. proposes drug delivery compositions for colonic delivery of insulin. The drug delivery compositions include insulin, an absorption promoter which (a) includes a mixture of fatty acids having 6 to 16 carbon atoms or a salt thereof and a dispersing agent, or (b) comprises a mixture of mono/diglycerides of medium chain fatty acids and a dispersing agent, and a coating to prevent the release of the insulin and absorption promoter until the tablet, capsule or pellet reaches the proximal colon.

It is desirable to provide pharmaceutical compositions for administration of insulin that can provide improved bioavailability when compared to the conventional compositions described above.

SUMMARY OF THE INVENTION

Pharmaceutical compositions according to embodiments of the present invention use a mixture of bile salts and fatty acids in various ratios to provide synergistic effects in the administration of insulin and/or insulin drug-oligomer conjugates that cannot be achieved with bile salts or fatty acids alone. For example, in some embodiments of the present invention, using mixtures of bile salts and fatty acids in a particular ratio alters the precipitation characteristics of the bile salt so that the bile salt more readily re-solubilizes if it happens to precipitate out of the pharmaceutical composition (e.g., upon encountering an acidic environment in the gut). As another example, in some embodiments of the present invention, using mixtures of bile salts and fatty acids in a particular ratio lowers the precipitation point of the bile salt in the pharmaceutical composition, providing additional buffering capacity for the pharmaceutical composition.

According to embodiments of the present invention, a pharmaceutical composition includes insulin or an insulin drug-oligomer conjugate wherein the conjugate includes an insulin drug covalently coupled to an oligomeric moiety, a fatty acid component that includes a fatty acid, and a bile salt component that includes a bile salt, or a bile salt component without a fatty acid component. The fatty acid component and the bile salt component can be present in a weight-to-weight ratio of between 1:15 and 15:1 or any ratio in between these values. The fatty acid component is present in an amount sufficient to lower the precipitation point of the bile salt compared to a precipitation point of the bile salt if the fatty acid component were not present in the pharmaceutical composition. The bile salt component is present in an amount sufficient to lower the solubility point of the fatty acid compared to a solubility point of the fatty acid if the bile salt were not present in the pharmaceutical composition.

According to other embodiments of the present invention, a pharmaceutical composition includes insulin or an insulin drug-oligomer conjugate that includes an insulin drug covalently coupled to an oligomeric moiety, a bile salt component comprising a bile salt, and a fatty acid component comprising a fatty acid, or a bile salt component without a fatty acid component. The fatty acid component and the bile salt component, when together, can be present in a weight-to-weight ratio of anywhere between 1:15 and 15:1. The fatty acid component is present in a first amount such that, at the precipitation point of the bile salt, the bile salt precipitates as first bile salt particles that, upon a return to a pH above the precipitation point of the bile salt, re-solubilize more quickly than second bile salt particles that would have precipitated if the fatty acid component were not present in the composition.

According to still other embodiments of the present invention, a pharmaceutical composition includes insulin or an insulin drug-oligomer conjugate that includes an insulin drug covalently coupled to an oligomeric moiety, between 0.1 and 15% (w/v) of a fatty acid component, and between 0.1 and 15% (w/v) of a bile salt component. The fatty acid component and the bile salt component, when together, can be present in any weight-to-weight ratio of anywhere between 1:15 and 15:1.

According to other embodiments of the present invention, methods of treating an insulin deficiency in a subject in need of such treatment include administering to the subject a pharmaceutical composition according to embodiments of the present invention.

According to still other embodiments of the present invention, a method of providing a pharmaceutical composition includes selecting an amount of a bile salt to include in the composition based on the ability of the bile salt to increase the solubility of a fatty acid component when the composition has a pH of 8.5 or less.

According to yet other embodiments of the present invention, a method of providing a pharmaceutical composition includes selecting an amount of a fatty acid to include in the composition based on the ability of the fatty acid to lower the precipitation point of a bile salt component in the composition to a pH of 5.5 or less.

According to other embodiments of the present invention, a method of providing a pharmaceutical composition includes selecting an amount of a fatty acid to include in the composition based on the ability of the fatty acid to alter the precipitation characteristics of a bile salt component in the composition.

DETAILED DESCRIPTION OF THE INVENTION

Figure 1:
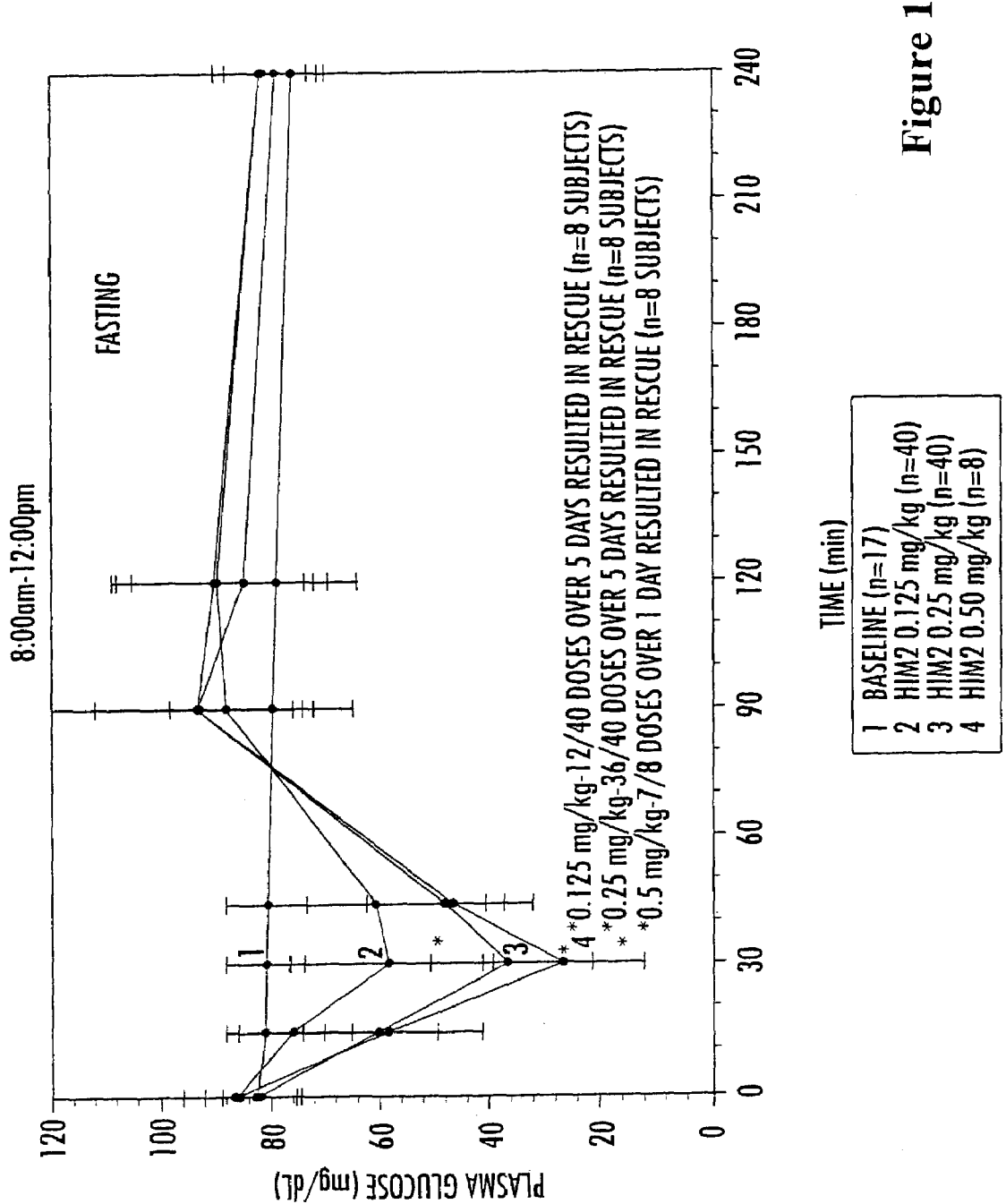
FIG. 1 illustrates a comparison of mean plasma glucose vs. time curves resulting from oral administration of various doses of embodiments of the present invention in fasting, non-diabetic subjects compared with a mean plasma glucose vs. time curve for baseline plasma glucose.

Certain embodiments of the present invention are based on the surprising and unexpected discovery that fatty acids and bile salts in combination have a synergistic effect, which is more than an additive effect on the bioavailability and/or bioefficacy of a drug or drug oligomer-conjugate when administered in combination with the drug or drug oligomer conjugate.

The present invention now will be described more fully hereinafter with reference to the accompanying drawings, in which various embodiments of the invention are shown. This invention can, however, be embodied in many different forms and should not be construed as limited to the embodiments set forth herein; rather, these embodiments are provided so that this disclosure will be thorough and complete, and will fully convey the scope of the invention to those skilled in the art.

All amino acid abbreviations used in this disclosure are those accepted by the United States Patent and Trademark Office as set forth in 37 C.F.R. § 1.822(b).

As used herein, the term "between" when used to describe various ranges should be interpreted to include the endpoints of the described ranges.

As used herein, the term "substantially monodispersed" is used to describe a mixture of compounds wherein at least about 95 percent of the compounds in the mixture have the same molecular weight.

As used herein, the term "monodispersed" is used to describe a mixture of compounds wherein about 100 percent of the compounds in the mixture have the same molecular weight.

As used herein, the term "insulin polypeptide" means a polypeptide possessing at least some of the biological activity of insulin (e.g., ability to affect the body through insulin's primary mechanism of action). For example, an insulin polypeptide can be a polypeptide such as insulin having an A-chain polypeptide and a B-chain polypeptide coupled to the A-chain polypeptide by disulfide bonds. In various embodiments of the present invention, the insulin polypeptide can possess a majority of the biological activity of insulin and can possess substantially all of the biological activity of insulin, and in some embodiments, can possess all of the biological activity of insulin.

As used herein, the term "insulin" means without limitation the insulin of one of the following species human, cow, pig, sheep, horse, dog, chicken, duck, whale, or the like provided by natural, synthetic, or genetically engineered sources. In various embodiments of the present invention, insulin is human insulin.

As used herein, the term "insulin analog" means insulin wherein one or more of the amino acids have been replaced while retaining some or all of the activity of the insulin. The analog is described by noting the replacement amino acids with the position of the replacement as a superscript followed by a description of the insulin. For example, "Pro$^{B29}$ insulin, human" means that the lysine typically found at the B29 position of a human insulin molecule has been replaced with proline.

Insulin analogs can be obtained by various means, as will be understood by those skilled in the art. For example, certain amino acids can be substituted for other amino acids in the insulin structure without eliminating a therapeutically beneficial effect. As the interactive capacity and nature of insulin defines its biological functional activity, certain amino acid sequence substitutions can be made in the amino acid sequence and nevertheless remain a polypeptide without eliminating a therapeutically beneficial effect.

In making such substitutions, the hydropathic index of amino acids can be considered. The importance of the hydropathic amino acid index in conferring interactive biologic function on a polypeptide is generally understood in the art. It is accepted that the relative hydropathic character of the amino acid contributes to the secondary structure of the resultant polypeptide, which in turn defines the interaction of the protein with other molecules, for example, enzymes, substrates, receptors, DNA, antibodies, antigens, and the like. Each amino acid has been assigned a hydropathic index on the basis of its hydrophobicity and charge characteristics as follows: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). As will be understood by those skilled in the art, certain amino acids can be substituted by other amino acids having a similar hydropathic index or score and still result in a polypeptide with similar biological activity, i.e., still obtain a biological functionally equivalent polypeptide. In making such changes, the substitution of amino acids whose hydropathic indices are within ±2 of each other is desirable, those, which are within ±1 of each other, are also desirable, and those within ±0.5 of each other are also desirable.

It is also understood in the art that the substitution of like amino acids can be made effectively on the basis of hydrophilicity. U.S. Pat. No. 4,554,101, the disclosure of which is incorporate herein in its entirety, provides that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: arginine (+3.0); lysine (±3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5) cysteine (−1.0); methionine (−1.3); valine (−1.5); leucine (−1.8); isoleucine (−1.8); tyrosine ('phenylalanine (−2.5); tryptophan (−3.4). As is understood by those skilled in the art, an amino acid can be substituted for another having a similar hydrophilicity value and still obtain a biologically equivalent, and in particular, an immunologically equivalent polypeptide. In such changes, the substitution of amino acids whose hydrophilicity values are within ±2 of each other is desirable, those that are within ±1 of each other are also desirable, and those within ±0.5 of each other are also desirable.

As outlined above, amino acid substitutions are generally therefore based on the relative similarity of the amino acid side-chain substituents, for example, their hydrophobicity, hydrophilicity, charge, size, and the like. Exemplary substitutions (i.e., amino acids that can be interchanged without significantly altering the biological activity of the polypeptide) that take various of the foregoing characteristics into consideration are well known to those of skill in the art and include, for example: arginine and lysine; glutamate and aspartate; serine and threonine; glutamine and asparagine; and valine, leucine and isoleucine.

As will be understood by those skilled in the art, insulin and/or insulin analogs of this invention can be prepared by a variety of recognized peptide synthesis techniques including, but not limited to, classical (solution) methods, solid phase methods, semi-synthetic methods, and recombinant DNA methods.

Examples of human insulin analogs include, but are not limited to, $Gly^{A21}$ insulin, human; $Gly^{A21}$ $Gln^{B3}$ insulin, human; $Ala^{A21}$ insulin, human; $Ala^{A21}$ $Gln^{B3}$ insulin, human; $Gln^{B3}$ insulin, human; $Gln^{B30}$ insulin, human; $Gly^{A21}$ $Glu^{B30}$ insulin, human; $Gly^{A21}$ $Gln^{B3}$ $Glu^{B30}$ insulin, human; $Gln^{B3}$ $Glu^{B30}$ insulin, human; $Asp^{B28}$ insulin, human; $Lys^{B28}$ insulin, human; $Leu^{B28}$ insulin, human; $Val^{B28}$ insulin, human; $Ala^{B28}$ insulin, human; $Asp^{B28}$ $Pro^{B29}$ insulin, human; $Lys^{B28}$ $Pro^{B29}$ insulin, human; $Leu^{B28}$ $Pro^{B29}$ insulin, human; $Val^{B28}$ $Pro^{B29}$ insulin, human; $Ala^{B28}$ $Pro^{B29}$ insulin, human. An insulin analog of this invention can also include an insulin molecule comprising a B-chain with additional lysines added.

As used herein, the term "insulin fragment" means a segment of the amino acid sequence found in the insulin that retains some or all of the activity of the insulin. Insulin fragments are denoted by stating the position(s) in an amino acid sequence followed by a description of the amino acid. For example, a "B25–B30 human insulin" fragment would be the six amino acid sequence corresponding to the B25, B26, B27, B28, B29 and B30 positions in the human insulin amino acid sequence.

As used herein, the term "insulin fragment analog" means a segment of the amino acid sequence found in the insulin a molecule wherein one or more of the amino acids in the segment have been replace while retaining some or all of the activity of the insulin.

As used herein, the term "polypeptide" means a peptide having two or more amino acid residues.

As used herein, the term "amphiphilically balanced" means capable of substantially dissolving in water and capable of penetrating biological membranes.

As used herein, the term "polyalkylene glycol" refers to straight or branched polyalkylene glycol polymers such as polyethylene glycol, polypropylene glycol, and polybutylene glycol, and includes the monoalkylether of the polyalkylene glycol. The term "polyalkylene glycol subunit" refers to a single polyalkylene glycol unit. For example, a polyethylene glycol subunit would be —O—$CH_2$—$CH_2$—O—.

As used herein, the term "lipophilic" means the ability to dissolve in lipids and/or the ability to penetrate, interact with and/or traverse biological membranes, and the term, "lipophilic moiety" or "lipophile" means a moiety which is lipophilic and/or which, when attached to another chemical entity, increases the lipophilicity of such chemical entity. Examples of lipophilic moieties include, but are not limited to, alkyls, fatty acids, esters of fatty acids, cholesteryl, adamantyl and the like.

As used herein, the term "lower alkyl" refers to substituted or unsubstituted alkyl moieties having from one to five carbon atoms.

As used herein, the term "higher alkyl" refers to substituted or unsubstituted alkyl moieties having six or more carbon atoms.

Unless otherwise noted herein, the term "bile salt" includes bile salts and the free acids thereof.

Unless otherwise noted herein, the term "fatty acid" includes fatty acids and pharmaceutically acceptable salts or esters thereof.

As used herein, the term "bile salt component" means a mixture of one or more salts.

As used herein, the term "fatty acid component" means a mixture of one or more fatty acids.

As used herein, the "precipitation point" of a compound or component of the pharmaceutical composition is the pH at which at least 25% of the compound or component precipitates out of the composition. Accordingly, lowering the precipitation point means lowering the pH at which at least 25% of the compound or component precipitates out of the composition. Conversely, raising the precipitation point means raising the pH at which at least 25% of the compound or component precipitates out of the composition.

As used herein, the "solubility point" of a compound or component of the pharmaceutical composition is the pH at which at least 75% of the compound or component is solubilized in the composition. Accordingly, lowering the solubility point means lowering the pH at which at least 75% of the compound or component is solubilized in the composition. Conversely, raising the solubility point means raising the pH at which at least 75% of the compound or component is solubilized in the composition.

As used herein, the term "medium-chain fatty acid" means a saturated or unsaturated fatty acid having from 8 to 14 carbon atoms.

As used herein, the term "long-chain fatty acid" means a saturated or unsaturated fatty acid having greater than 14 carbon atoms.

According to embodiments of the present invention, a pharmaceutical composition of this invention comprises insulin, a fatty acid component and a bile salt component, or a bile salt component without a fatty acid component. A pharmaceutical composition of this invention also comprises insulin, an insulin polypeptide, an insulin-oligomer conjugate or an insulin polypeptide-oligomer conjugate, along with a fatty acid component, and a bile salt component. The insulin drug-oligomer conjugate includes an insulin drug covalently coupled to an oligomeric moiety. The fatty acid component includes a fatty acid, and the bile salt component includes a bile salt.

According to these embodiments of the present invention, the fatty acid component and the bile salt component, when together, can be present in a weight-to-weight ratio of between 1:15 and 15:1. In certain embodiments, for example, the fatty acid component and the bile salt component can be present in any weight-to-weight ratio of, for example, anywhere between 1:10 and 10:1, 1:5 and 5:1, 1:3 and 3:1 and/or 1:2 and 2:1, as well as any value in between any of these ranges.

According to some embodiments of the present invention, the fatty acid component is present in an amount sufficient to lower the precipitation point of the bile salt compared to a precipitation point of the bile salt if the fatty acid component were not present in the pharmaceutical composition. The fatty acid component can be present in an amount sufficient to lower the precipitation point of the bile salt by at least 0.5 pH units, and can be present in an amount sufficient to lower the precipitation point of the bile salt by at least 1.0 pH units.

According to other embodiments of the present invention, the bile salt component is present in an amount sufficient to lower the solubility point of the fatty acid compared to a solubility point of the fatty acid if the bile salt were not present in the pharmaceutical composition. For example, the bile salt component can be present in an amount sufficient to lower the solubility point of the fatty acid by at least 0.25 pH units, or in an amount sufficient to lower the solubility point of the fatty acid by at least 0.5 pH units.

According to still other embodiments of the present invention, the fatty acid component is present in an amount sufficient to lower the precipitation point pH of the bile salt compared to a precipitation point pH of the bile salt if the fatty acid were not present in the pharmaceutical composition as described above, and the bile salt component is present in an amount sufficient to lower the solubility point pH of the fatty acid compared to a solubility point pH of the fatty acid if the bile salt were not present in the pharmaceutical composition as described above.

The bile salt in the bile salt component can be various bile salts as will be understood by those skilled in the art, including unconjugated and conjugated bile salts. Unconjugated bile salts are bile salts in which the primary side chain has a single carboxyl group which is at the terminal position and which is unsubstituted. Exemplary unconjugated bile salts include, but are not limited to, cholate, ursodeoxycholate, chenodeoxycholate, and deoxycholate. Conjugated bile salts are bile salts in which the primary side chain has a carboxyl group that is substituted with, for example, an amino acid derivative linked via its nitrogen atom to the carboxyl group. Exemplary conjugated bile salts include, but are not limited to, taurocholate, glycocholate, taurodeoxycholate, and glycodeoxycholate. Mixtures of the various unconjugated and conjugated bile salts can also be used. The bile salt can be a pharmaceutically acceptable salt of cholic acid or the bile salt can be sodium cholate. In additional embodiments, the bile salt component can consist essentially of sodium cholate.

The fatty acid in the fatty acid component of this invention can be various fatty acids as will be understood by those skilled in the art, including natural and synthetic fatty acids. The fatty acid can have between a lower limit of 2, 3, 4, 5, 6, 7, 8, 9, 10, 11, 12, 13, 14, 15, 16, 17, 18, or 19 carbon atoms and an upper limit of 3, 4, 5, 6, 7, 8, 9, 10, 11, 12, 13, 14, 15, 16, 17, 18, 19, 20, 21 or 22 carbon atoms. The fatty acid can be either saturated or unsaturated. Exemplary saturated fatty acids include, but are not limited to, ethanoic acid, propanoic acid, butanoic acid, pentanoic acid, hexanoic acid, heptanoic acid, octanoic acid, nonanoic acid, decanoic acid, undecanoic acid, dodecanoic acid, tridecanoic acid, tetradecanoic acid, pentadecanoic acid, hexadecanoic acid, heptadecanoic acid, octadecanoic acid, nonadecanoic acid, eicosanoic acid, one or more of which can be referred to by their common names such as acetic acid, caproic acid, caprylic acid, capric acid, lauric acid, myristic acid, palmitic acid, stearic acid, arachidic acid, behenic acid, lignoceric acid, and cerotic acid. Exemplary unsaturated fatty acids include, but are not limited to, cis-9-octadecenoic acid, trans-9-octadecenoic acid, 9,12-octadecatrienoic acid, 9,12,15-octadecenoic acid, and 5,8,11,14-eicosatetraenoic acid, one or more of which can be referred to by their common names such as oleic acid, elaidic acid, linoleic acid, linolenic acid, and arachidonic acid.

In some embodiments, the fatty acid component comprises a mixture of two or more fatty acids. In other embodiments, the fatty acid component comprises a medium-chain fatty acid and a long-chain fatty acid. In certain embodiments, the medium-chain fatty acid is capric acid, lauric acid, or a mixture thereof. In other embodiments, the long-chain fatty acid is oleic acid.

The insulin drug can be various insulin drugs as will be understood by those skilled in the art. The insulin drug can be an insulin polypeptide. The insulin polypeptide can have an A-chain polypeptide and a B-chain polypeptide. The A-chain polypeptide can be devoid of lysine residues. The B-chain polypeptide can comprise a single lysine residue. The A-chain polypeptide and the B-chain polypeptide can be cross-linked, and can be cross-linked using one or more disulfide bonds. In certain embodiments, the A-chain polypeptide and the B-chain polypeptide can each comprise cysteine residues, one or more of which are coupled using one or more disulfide bonds to cross-link the A-chain polypeptide with the B-chain polypeptide. In certain embodiments, the insulin polypeptide is insulin (e.g., recombinant insulin), an insulin analog, an insulin fragment, or an insulin analog fragment. In certain embodiments, the insulin polypeptide is human insulin, a human insulin analog, a human insulin fragment, or a human insulin analog fragment.

The insulin drug can be conjugated to an oligomer. The oligomer can be various oligomers as will be understood by those skilled in the art. In general, the oligomer can be any oligomer capable of being coupled to a polypeptide as will be understood by those skilled in the art. For example, the oligomer can be a poly-dispersed oligomer as described in U.S. Pat. No. 4,179,337 to Davis et al.; U.S. Pat. No. 5,567,422 to Greenwald; U.S. Pat. No. 5,359,030 to Ekwuribe; U.S. Pat. No. 5,438,040 to Ekwuribe, U.S. Pat. No. 5,681,811 to Ekwuribe, and U.S. Pat. No. 6,309,633 to Ekwuribe et al., the disclosures of each of which are incorporated herein by reference in their entireties. As another example, the oligomer can be a non-polydispersed oligomer as described in U.S. Pat. No. 6,835,802 to Ekwuribe et al. entitled "Methods of Synthesizing Substantially Monodispersed Mixtures of Polymers Having Polyethylene Glycol Mixtures." published as U.S. Pub. No. 2003-0004304 A1; U.S. Pat. No. 6,858,580 to Ekwuribe et al. entitled "Mixtures of Drug-Oligomer Conjugates Comprising Polyalkylene Glycol, Uses Thereof, and Methods of Making Same," published as U.S. Pub. No. 2003-0228275 A1; and U.S. Pat. No. 6,828,297 to Ekwuribe et al. entitled "Mixtures of Insulin Drug-Oligomer Conjugates Comprising Polyalkylene Glycol, Uses Thereof, and Methods of Making Same," published as U.S. Pub. No. 0027748 A1; the disclosures of each of which are incorporated herein in their entireties.

In some embodiments, the oligomer consists essentially of a hydrophilic moiety as will be understood by those skilled in the art including, but not limited to, polyalkylene glycols such as polyethylene glycol or polypropylene glycol, polyoxyethylenated polyols, copolymers thereof and block copolymers thereof, provided that the hydrophilicity of the block copolymers is maintained. The hydrophilic moiety can be a linear or branched polyalkylene glycol moiety. The polyalkylene glycol moiety can have at least 1, 2, 3, 4, 5, 6 or 7 polyalkylene glycol subunits. The polyalkylene glycol moiety can have between a lower limit of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, or 49 polyalkylene glycol subunits and an upper limit of 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more polyalkylene glycol subunits. In certain embodiments, the polyalkylene glycol moiety has between a lower limit of 2, 3, 4, 5, or 6 polyalkylene glycol subunits and an upper limit of 5, 6, 7, 8, 9, 10, 11, 12, 13, 14, 15, 16, 17, 18, 19, or 20 polyalkylene glycol subunits. In other embodiments, the polyalkylene glycol moiety can have between a lower limit of 3, 4, 5, or 6 polyalkylene glycol subunits and an upper limit of 5, 6, 7, 8, 9, 10, 11, or 12 polyalkylene glycol subunits. The polyalkylene glycol moiety can also, in some embodiments, have between a lower limit of 4, 5, or 6 polyalkylene glycol subunits and an upper limit of 6, 7, or 8 polyalkylene glycol subunits. The polyalkylene glycol moiety of the oligomer can be a lower alkyl polyalkylene glycol moiety such as a polyethylene glycol moiety, a polypropylene glycol moiety, or a polybutylene glycol moiety. When the polyalkylene glycol moiety is a polypropylene glycol moiety, the moiety can have a uniform (i.e., not random) structure. An exemplary polypropylene glycol moiety having a uniform structure is as follows:

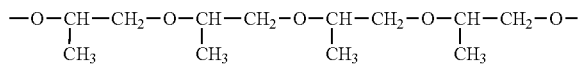

This uniform polypropylene glycol structure can be described as having only one methyl substituted carbon atom adjacent each oxygen atom in the polypropylene glycol chain. Such uniform polypropylene glycol moieties can exhibit both lipophilic and hydrophilic characteristics.

The oligomer can comprise one or more other moieties as will be understood by those skilled in the art including, but not limited to, additional hydrophilic moieties, lipophilic moieties, spacer moieties, linker moieties, and terminating moieties. The various moieties in the oligomer are covalently coupled to one another by either hydrolyzable or non-hydrolyzable bonds.

The oligomer can further comprise one or more additional hydrophilic moieties (i.e., moieties in addition to the polyalkylene glycol moiety) including, but not limited to, sugars, polyalkylene glycols, and polyamine/PEG copolymers. Adjacent polyalkylene glycol moieties will be considered to be the same moiety if they are coupled by ether bonds. For example, the moiety

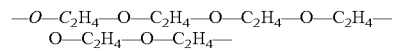

is a single polyethylene glycol moiety having six polyethylene glycol subunits. If this moiety were the only hydrophilic moiety in the oligomer, the oligomer would not contain an additional hydrophilic moiety. Adjacent polyethylene glycol moieties are considered to be different moieties if they are coupled by a bond other than an ether bond. For example, the moiety

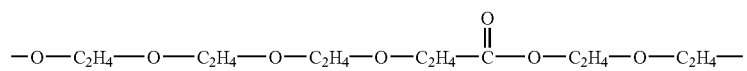

is a polyethylene glycol moiety having four polyethylene glycol subunits and an additional hydrophilic moiety having two polyethylene glycol subunits. In some embodiments, oligomers according to embodiments of the present invention can comprise a polyalkylene glycol moiety and no additional hydrophilic moieties.

The oligomer of this invention can consists essentially of one or more lipophilic moieties as will be understood by those skilled in the art. The lipophilic moiety has at least 1, 2, 3, 4, 5, or 6 carbon atoms. The lipophilic moiety can have between a lower limit of 1, 2, 3, 4, 5, 6, 7, 8, 9, 10, 11, 12, 13, 14, 15, 16, 17, 18, 19, 20, 21, 22, 23, 24, 25, 26, 27, 28, or 29 carbon atoms and an upper limit of 2, 3, 4, 5, 6, 7, 8, 9, 10, 11, 12, 13, 14, 15, 16, 17, 18, 19, 20, 21, 22, 23, 24, 25, 26, 27, 28, 29, or 30 carbon atoms. The lipophilic moiety can have between a lower limit of 2, 3, 4, 5, 6, 7, 8, 9, or 10 carbon atoms and an upper limit of 4, 5, 6, 7, 8, 9, 10, 11, 12, 13, 14, 15, 16, 17, 18, 19, 20, 21, or 22 carbon atoms. The lipophilic moiety can have between a lower limit of 3, 4, 5, 6, 7, 8, or 9 carbon atoms and an upper limit of 4, 5, 6, 7, 8, 9, 10, 11, 12, 13, or 14 carbon atoms. The lipophilic moiety can also have between a lower limit of 3, 4, 5, 6, or 7 carbon atoms and an upper limit of 6, 7, 8, 9, or 10 carbon atoms. The lipophilic moiety can be selected from the group consisting of saturated or unsaturated, linear or branched alkyl moieties, saturated or unsaturated, linear or branched fatty acid moieties, cholesterol, and adamantane. Exemplary alkyl moieties include, but are not limited to, saturated, linear alkyl moieties such as methyl, ethyl, propyl, butyl, pentyl, hexyl, heptyl, octyl, nonyl, decyl, undecyl, dodecyl, tridecyl, tetradecyl, pentadecyl, hexadecyl, octadecyl, nonadecyl and eicosyl; saturated, branched alkyl moieties such as isopropyl, sec-butyl, tert-butyl, 2-methylbutyl, tert-pentyl, 2-methyl-pentyl, 3-methylpentyl, 2-ethylhexyl, 2-propylpentyl; and unsaturated alkyl moieties derived from the above saturated alkyl moieties including, but not limited to, vinyl, allyl, 1-butenyl, 2-butenyl, ethynyl, 1-propynyl, and 2-propynyl. Exemplary fatty acid moieties include, but are not limited to, unsaturated fatty acid moieties such as lauroleate, myristoleate, palmitoleate, oleate, elaidate, erucate, linoleate, linolenate, arachidonate, eicosapentaentoate, and docosahexaenoate; and saturated fatty acid moieties such as acetate, caproate, caprylate, caprate, laurate, arachidate, behenate, lignocerate, and cerotate. The fatty acid moiety can be natural or synthetic.

The oligomer can further comprise one or more spacer moieties as will be understood by those skilled in the art. Spacer moieties can, for example, be used to separate a hydrophilic moiety from a lipophilic moiety, to separate a lipophilic moiety or hydrophilic moiety from the insulin polypeptide, to separate a first hydrophilic or lipophilic moiety from a second hydrophilic or lipophilic moiety, or to separate a hydrophilic moiety or lipophilic moiety from a linker moiety. Spacer moieties can be selected from the group comprising sugar, cholesterol and glycerine moieties. Sugar moieties can be various sugar moieties as will be understood by those skilled in the art including, but not limited to, monosaccharide moieties and disaccharide moieties. In some embodiments, monosaccharide moieties have between 4 and 6 carbon atoms.

The oligomer can further comprise one or more linker moieties that are used to couple the oligomer with the insulin polypeptide as will be understood by those skilled in the art. Linker moieties can include, but are not limited to, alkyl and fatty acid moieties. The alkyl linker moiety can be a saturated or unsaturated, linear or branched alkyl moiety as will be understood by those skilled in the art including, but not limited to, methyl, ethyl, propyl, butyl, pentyl, hexyl, heptyl, octyl, nonyl, decyl, undecyl, dodecyl, tridecyl, tetradecyl, pentadecyl, hexadecyl, octadecyl, nonadecyl, eicosyl, isopropyl, sec-butyl, tert-butyl, 2-methylbutyl, tert-pentyl, 2-methyl-pentyl, 3-methylpentyl, 2-ethylhexyl, 2-propylpentyl, vinyl, allyl, 1-butenyl, 2-butenyl, ethynyl, 1-propynyl, and 2-propynyl. The alkoxy moiety can be various alkoxy moieties including, but not limited to, methoxy, ethoxy, propoxy, butoxy, pentyloxy, hexyloxy, heptyloxy, octyloxy, nonyloxy, decyloxy, undecyloxy, dodecyloxy, tridecyloxy, tetradecyloxy, pentadecyloxy, hexadecyloxy, octadecyloxy, nonadecyloxy, eicosyloxy, isopropoxy, sec-butoxy, tert-butoxy, 2-methylbutoxy, tert-pentyloxy, 2-methyl-pentyloxy, 3-methylpentyloxy, 2-ethylhexyloxy, 2-propylpentyloxy, vinyloxy, allyloxy, 1-butenyloxy, 2-butenyloxy, ethynyloxy, 1-propynyloxy, and 2-propynyloxy. The alkyl linker moiety can have between a lower limit of 1, 2, 3, 4, 5, 6, 7, 8, 9, 10, 11, 12, 13, 14, 15, 16, 17, 18, 19, or 20 carbon atoms and an upper limit of 2, 3, 4, 5, 6, 7, 8, 9, 10, 11, 12, 13, 14, 15, 16, 17, 18, 19, 20, 21, 22, 23, 24, 25, 26, 27, 28, 29, or 30 carbon atoms, and in some embodiments, can have between 1, 2, 3, 4, or 5 carbon atoms and 8, 9, 10, 11, or 12 carbon atoms. The fatty acid linker moiety can be a saturated or unsaturated, linear or branched fatty acid moiety as will be understood by those skilled in the art including, but not limited to, lauroleate, myristoleate, palmitoleate, oleate, elaidate, erucate, linoleate, linolenate, arachidonate, eicosapentaentoate, docosahexaenoate, acetate, caproate, caprylate, caprate, laurate, arachidate, behenate, lignocerate, and cerotate. The fatty acid linker moiety can be a natural or synthetic fatty acid. The fatty acid linker moiety can have between a lower limit of 1, 2, 3, 4, 5, 6, 7, 8, 9, 10, 11, 12, 13, 14, 15, 16, 17, 18, 19, or 20 carbon atoms and an upper limit of 2, 3, 4, 5, 6, 7, 8, 9, 10, 11, 12, 13, 14, 15, 16, 17, 18, 19, 20, 21, 22, 23, 24, 25, 26, 27, 28, 29, or 30 carbon atoms and in some embodiments, can have between 1, 2, 3, 4, or 5 carbon atoms and 8, 10, 12, 14 or 16 carbon atoms. When the linker moiety is a fatty acid, the oligomeric moiety can be coupled to the insulin drug via the carbonyl group of a carboxylic acid moiety of the fatty acid.

The oligomer can further comprise one or more terminating moieties at the one or more ends of the oligomer, which are not coupled to the insulin polypeptide. The terminating moiety can be an alkyl or alkoxy moiety. The alkyl or alkoxy moiety can have between a lower limit of 1, 2, 3, 4, 5, 6, 7, 8, 9, 10, 11, 12, 13, 14, 15, 16, 17, 18, 19, or 20 carbon atoms and an upper limit of 2, 3, 4, 5, 6, 7, 8, 9, 10, 11, 12, 13, 14, 15, 16, 17, 18, 19, 20, 21, 22, 23, 24, 25, 26, 27, 28, 29, or 30 carbon atoms. The alkyl or alkoxy moiety can also have between a lower limit of 1, 2, 3, 4, 5, 6, or 7 carbon atoms and an upper limit of 5, 6, 7, 8, 9, 10, 11, 12, 13, or 14 carbon atoms. The alkyl or alkoxy moiety in some embodiments has between a lower limit of 1, 2, 3, 4, or 5 carbon atoms and an upper limit of 5, 6, 7, 8, 9, or 10 carbon atoms. The alkyl or alkoxy moiety in certain embodiments, has between a lower limit of 1, 2, 3, or 4 carbon atoms and an upper limit of 5, 6, or 7 carbon atoms. The alkyl moiety can be a linear or branched, saturated or unsaturated alkyl moiety as will be understood by those skilled in the art including, but not limited to, methyl, ethyl, propyl, butyl, pentyl, hexyl, heptyl, octyl, nonyl, decyl, undecyl, dodecyl, tridecyl, tetradecyl, pentadecyl, hexadecyl, octadecyl, nonadecyl, eicosyl, isopropyl, sec-butyl, tert-butyl, 2-methylbutyl, tert-pentyl, 2-methyl-pentyl, 3-methylpentyl, 2-ethylhexyl, 2-propylpentyl, vinyl, allyl, 1-butenyl, 2-butenyl, ethynyl, 1-propynyl, and 2-propynyl. The alkoxy moiety can be various alkoxy moieties including, but not limited to, methoxy, ethoxy, propoxy, butoxy, pentyloxy, hexyloxy, heptyloxy, octyloxy, nonyloxy, decyloxy, undecyloxy, dodecyloxy, tridecyloxy, tetradecyloxy, pentadecyloxy, hexadecyloxy, octadecyloxy, nonadecyloxy, eicosyloxy, isopropoxy, sec-butoxy, tert-butoxy, 2-methylbutoxy, tert-pentyloxy, 2-methyl-pentyloxy, 3-methylpentyloxy, 2-ethylhexyloxy, 2-propylpentyloxy, vinyloxy, allyloxy, 1-butenyloxy, 2-butenyloxy, ethynyloxy, 1-propynyloxy, and 2-propynyloxy. The terminating moiety can be a lower alkyl moiety such as methyl, ethyl, propyl, isopropyl, butyl, sec-butyl, tert-butyl, pentyl, or tert-pentyl, or a lower alkoxy moiety such as methoxy, ethoxy, propoxy, isopropoxy, butoxy, sec-butoxy, tert-butoxy, pentyloxy, or tert-pentyloxy. In some embodiments, the terminating moiety is methyl or methoxy. While the terminating moiety can be an alkyl or alkoxy moiety, it is to be understood that the terminating moiety can be various moieties as will be understood by those skilled in the art including, but not limited to, sugars, cholesterol, alcohols, and fatty acids.

According to embodiments of the present invention, the insulin drug-oligomer conjugate comprises the structure of Formula I:

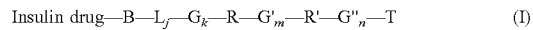

$$\text{Insulin drug}-B-L_j-G_k-R-G'_m-R'-G''_n-T \qquad (I)$$

wherein:
Insulin drug is insulin, an insulin drug, or insulin polypeptide as described above;
B is a bonding moiety;
L is a linker moiety;
G, G' and G'' are individually selected spacer moieties;
R is a lipophilic moiety and R' is a polyalkylene glycol moiety, or R' is the lipophilic moiety and R is the polyalkylene glycol moiety and only one of the R or R' can be present;
T is a terminating moiety; and
j, k, m and n are individually 0 or 1.

The bonding moiety can be, but is not limited to, an ester moiety, a thio-ester moiety, an ether moiety, a carbamate moiety, a thio-carbamate moiety, a carbonate moiety, a thio-carbonate moiety, an amide moiety, a urea moiety, and/or a covalent bond. The linker moiety, spacer moieties, lipophilic moiety, polyalkylene glycol moiety, and terminating moiety are described herein. In certain embodiments, oligomers of these embodiments do not include spacer moieties (i.e., k, m and n are 0).

In other embodiments, the insulin drug-oligomer conjugate comprises the structure of Formula II:

$$\text{Insulin drug}-X(CH_2)_mY(C_2H_4O)_nR \qquad (II)$$

wherein:
Insulin drug is a drug of the present invention;
X is —C(O)— or —O—;
Y is an ester, an ether, a carbamate, a carbonate, or an amide bonding moiety, and can be an ether bonding moiety;
m is between a lower limit of 0, 1, 2, 3, 4, 5, 6, 7, 8, 9, 10, 11, 12, 13, 14, 15, 16, 17, 18, 19, or 20 and an upper limit of 2, 3, 4, 5, 6, 7, 8, 9, 10, 11, 12, 13, 14, 15, 16, 17, 18, 19, 20, 21, 22, 23, 24, 25, 26, 27, 28, 29, or 30, and can be between a lower limit of 2, 3, 4, 5, 6, 7, 8, 9, or 10 and an upper limit of 4, 5, 6, 7, 8, 9, 10, 11, 12, 13, 14, 15, 16, 17, 18, 19, 20, 21, or 22, and can also be between a lower limit of 3, 4, 5, 6, 7, 8, or 9 and an upper limit of 4, 5, 6, 7, 8, 9, 10, 11, 12, 13, or 14, and/or between a lower limit of 3, 4, 5, 6, or 7 and an upper limit of 6, 7, 8, 9, or 10;
n is between a lower limit of 0, 1, 2, 3, 4, 5, 6, 7, 8, 9, 10, 11, 12, 13, 14, 15, 16, 17, 18, 19, or 20 and an upper limit of 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50, and can be between a lower limit of 2, 3, 4, 5, or 6 and an upper limit of 5, 6, 7, 8, 9, 10, 11, 12, 13, 14, 15, 16, 17, 18, 19, or 20, and can also be between a lower limit of 3, 4, 5, or 6 and an upper limit of 5, 6, 7, 8, 9, 10, 11, or 12 polyalkylene glycol subunits, and/or a lower limit of 4, 5, or 6 and an upper limit of 6, 7, or 8 polyalkylene glycol subunits, and can be 7 in certain embodiments;
m and n cannot both be 0; and
R is a terminating moiety as described herein.

In still other embodiments, the insulin drug-oligomer conjugate comprises the structure of Formula III:

$$\text{Insulin drug}-x_1\text{-}(CH_2)_m(OC_2H_4)_nOR \qquad (III)$$

wherein:
Insulin drug is insulin or an insulin polypeptide as described above;
$X_1$ is —C(O)— or —O—;
m is between a lower limit of 0, 1, 2, 3, 4, 5, 6, 7, 8, 9, 10, 11, 12, 13, 14, 15, 16, 17, 18, 19, or 20 and an upper limit of 4, 5, 6, 7, 8, 9, 10, 11, 12, 13, 14, 15, 16, 17, 18, 19, 20, 21, 22, 23, 24, 25, 26, 27, 28, 29, or 30, and can be between a lower limit of 2, 3, 4, 5, 6, 7, 8, 9, or 10 and an upper limit of 2, 3, 4, 5, 6, 7, 8, 9, 10, 11, 12, 13, 14, 15, 16, 17, 18, 19, 20, 21, or 22, and can also be between a lower limit of 3, 4, 5, 6, 7, 8, or 9 and an upper limit of 4, 5, 6, 7, 8, 9, 10, 11, 12, 13, or 14, and/or between a lower limit of 3, 4, 5, 6, or 7 and an upper limit of 6, 7, 8, 9, or 10;
n is between a lower limit of 0, 1, 2, 3, 4, 5, 6, 7, 8, 9, 10, 11, 12, 13, 14, 15, 16, 17, 18, 19, or 20 and an upper limit of 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50, and can be between a lower limit of 2, 3, 4, 5, or 6 and an upper limit of 5, 6, 7, 8, 9, 10, 11, 12, 13, 14, 15, 16, 17, 18, 19, or 20, and can also be between a lower limit of 3, 4, 5, or 6 and an upper limit of 5, 6, 7, 8, 9, 10, 11, or 12 polyalkylene glycol subunits, and/or between a lower limit of 4, 5, or 6 and an upper limit of 6, 7, or 8 polyalkylene glycol subunits, and can be 7 in certain embodiments;
m and n cannot both be 0; and
R is a terminating moiety as described herein.

In yet other embodiments, the insulin drug-oligomer conjugate comprises the structure of Formula IV:

$$\text{Insulin drug}-\overset{O}{\underset{\|}{C}}-(CH_2)_m(OC_2H_4)_nOR \qquad (IV)$$

wherein:
Insulin drug is insulin or an insulin polypeptide as described above;
m is between a lower limit of 0, 1, 2, 3, 4, 5, 6, 7, 8, 9, 10, 11, 12, 13, 14, 15, 16, 17, 18, 19, or 20 and an upper limit of 4, 5, 6, 7, 8, 9, 10, 11, 12, 13, 14, 15, 16, 17, 18, 19, 20, 21, 22, 23, 24, 25, 26, 27, 28, 29, or 30, and can be between a lower limit of 2, 3, 4, 5, 6, 7, 8, 9, or 10 and an upper limit of 4, 5, 6, 7, 8, 9, 10, 11, 12, 13, 14, 15, 16, 17, 18, 19, 20, 21, or 22, and can also be between a lower limit of 3, 4, 5, 6, 7, 8, or 9 and an upper limit of 4, 5, 6, 7, 8, 9, 10, 11, 12, 13, or 14, and/or between a lower limit of 3, 4, 5, 6, or 7 and an upper limit of 6, 7, 8, 9, or 10;
n is between a lower limit of 0, 1, 2, 3, 4, 5, 6, 7, 8, 9, 10, 11, 12, 13, 14, 15, 16, 17, 18, 19, or 20 and an upper limit of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50, and can be between a lower limit of 2, 3, 4, 5, or 6 and an upper limit of 5, 6, 7, 8, 9, 10, 11, 12, 13, 14, 15, 16, 17, 18, 19, or 20, and can also be between a lower limit of 3, 4, 5, or 6 and an upper limit of 5, 6, 7, 8, 9, 10, 11, or 12 polyalkylene glycol subunits, and/or between a lower limit of 4, 5, or 6 and an upper limit of 6, 7, or 8 polyalkylene glycol subunits;
m and n are not both 0; and
R is a terminating moiety as described herein.

In still other embodiments, the insulin drug-oligomer conjugate comprises the structure of Formula V:

$$\text{Insulin drug}-\overset{O}{\underset{\|}{C}}-(CH_2)_5(OC_2H_4)_7OCH_3 \qquad (V)$$

wherein the insulin drug is a drug of the present invention. When the insulin drug is a human insulin and the conjugate of Formula V consists of the single oligomer coupled to the Lysine at the B29 position of the human insulin, the insulin-oligomer conjugate is referred to as HIM2.

In still other embodiments of the present invention, the drug-oligomer conjugate comprises the structure of Formula VI:

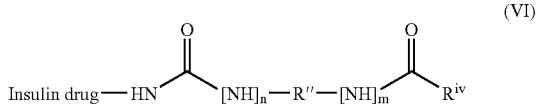

wherein:

Insulin drug is insulin or an insulin polypeptide as described above;

$R'''$ is a hydrophilic moiety, which can be, for example, a polyalkylene glycol moiety; a lower polyalkylene glycol moiety; and/or a polyethylene glycol moiety or polypropylene glycol moiety, where the polyalkylene glycol moiety has at least 1, 2, or 3 polyalkylene glycol subunits; and $R^{iv}$ is a lipophilic moiety, which can be an alkyl moiety having between 1 and 24 carbon atoms and/or a lower alkyl moiety; or $R^{iv}$ is a hydrophilic moiety, which can be a polyalkylene glycol moiety, a lower polyalkylene glycol moiety, and/or a polyethylene glycol moiety or polypropylene glycol moiety, where the polyalkylene glycol moiety has at least 1, 2, or 3 polyalkylene glycol subunits; and $R'''$ is a lipophilic moiety, which can be an alkyl moiety having between 1 and 24 carbon atoms, and/or a lower alkyl moiety; and n and m are individually 0 or 1.

When the drug portion of the drug-oligomer conjugate of Formula VI is human insulin, $R'''$ can be a polyethylene glycol having between a lower limit of 1, 2, 3, 4, 5, 6, or 7 polyethylene glycol subunits and an upper limit of 2, 3, 4, 5, 6, 7, 8, 9, or 10 polyethylene glycol subunits or $R'''$ can be a polypropylene glycol having between a lower limit of 1, 2, 3, 4, 5, 6, or 7 polypropylene glycol subunits and an upper limit of 2, 3, 4, 5, 6, 7, 8, 9, or 10 polypropylene glycol subunits, and $R^{iv}$ can be an alkyl having 1, 2, 3, 4, 5, 6, 7, 8, 9, 10, 11, 12, 13, 14, 15, 16, 17, 18, 19, or 20 carbon atoms. In some embodiments, $R'''$ can be a polyethylene glycol having between a lower limit of 1, 2, 3, or 4 polyethylene glycol subunits and an upper limit of 2, 3, 4, 5, 6, or 7 polyethylene glycol subunits or $R'''$ can be a polypropylene glycol having between a lower limit of 1, 2, 3, or 4 polypropylene glycol subunits and an upper limit of 2, 3, 4, 5, 6, or 7 polypropylene glycol subunits, and $R^{iv}$ can be an alkyl having 1, 2, 3, 4, 5, 6, 7, 8, 9, or 10 carbon atoms. In yet other embodiments, $R'''$ can be a polyethylene glycol having between a lower limit of 1, 2, or 3 polyethylene glycol subunits and an upper limit of 3, 4, or 5 polyethylene glycol subunits or $R'''$ can be a polypropylene glycol having between a lower limit of 1, 2, or 3 polypropylene glycol subunits and an upper limit of 3, 4, or 5 polypropylene glycol subunits, and $R^{iv}$ can be an alkyl having 3, 4, 5, or 6 carbon atoms.

In yet other embodiments of the present invention, the insulin drug-oligomer conjugate comprises the structure of Formula VII:

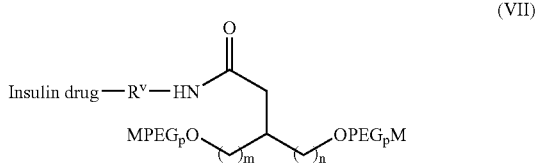

wherein:

Insulin drug is a drug of the present invention;

$R^v$ is an alkyl or a fatty acid moiety as described above with reference to the lipophilic moiety;

p is between a lower limit of 1, 2, 3, 4, 5, 6, 7, 8, 9, 10, 11, 12, 13, 14, 15, 16, 17, 18, 19, or 20 and an upper limit of 4, 5, 6, 7, 8, 9, 10, 11, 12, 13, 14, 15, 16, 17, 18, 19, 20, 21, 22, 23, 24, 25, 26, 27, 28, 29, or 30, and can be between a lower limit of 2, 3, 4, 5, 6, 7, 8, 9, or 10 and an upper limit of 4, 5, 6, 7, 8, 9, 10, 11, 12, 13, 14, 15, 16, 17, 18, 19, 20, 21, or 22, and can also be between a lower limit of 3, 4, 5, 6, 7, 8, or 9 and an upper limit of 4, 5, 6, 7, 8, 9, 10, 11, 12, 13, or 14, and/or between a lower limit of 3, 4, 5, 6, or 7 and an upper limit of 6, 7, 8, 9, or 10; and m and n are each at least 1 and m+n is from 2–17, and is preferably 4–15 and is more preferably 4–9.

In the various embodiments described above, the oligomer is covalently coupled to the insulin drug. In some embodiments, the oligomer is coupled to the insulin drug utilizing a hydrolyzable bond (e.g., an ester or carbonate bond). A hydrolyzable coupling can provide an insulin drug-oligomer conjugate that acts as a prodrug. In certain instances, for example where the insulin drug-oligomer conjugate is biologically inactive (i.e., the conjugate lacks the ability to affect the body through the insulin polypeptide's primary mechanism of action), a hydrolyzable coupling can provide for a time-release or controlled-release effect, providing the biologically active insulin drug over a given time period as one or more oligomers are cleaved from their respective biologically inactive insulin drug-oligomer conjugates to provide the biologically active insulin drug. In other embodiments, the oligomer is coupled to the insulin drug utilizing a non-hydrolyzable bond (e.g., a carbamate, amide, or ether bond). Use of a non-hydrolyzable bond is desirable to allow the biologically inactive insulin drug-oligomer conjugate to circulate in the bloodstream for an extended period of time, preferably at least 2 hours.

Oligomers employed in the various embodiments described above are commercially available or can be synthesized by various methods as will be understood by those skilled in the art. For example, polydispersed oligomers can be synthesized by the methods provided in one or more of the following references: U.S. Pat. No. 4,179,337 to Davis et al.; U.S. Pat. No. 5,567,422 to Greenwald; U.S. Pat. No. 5,359,030 to Ekwuribe; U.S. Pat. No. 5,438,040 to Ekwuribe, U.S. Pat. No. 5,681,811 to Ekwuribe, U.S. Pat. No. 6,309,633 to Ekwuribe et al. Non-polydispersed (e.g., substantially monodispersed and monodispersed) oligomers can be synthesized by methods provided in one or more of the following references: U.S. Pat. No. 6,835,802 to Ekwuribe et al. entitled "Methods of Synthesizing Substantially Monodispersed Mixtures of Polymers Having Polyethylene Glycol Mixtures," published as U.S. Pub. No. 2003-0004304 A1: U.S. Pat. No. 6,858,580 to Ekwuribe et al. entitled "Mixtures of Drug-Oligomer Conjugates Comprising Polyalkylene Glycol, Uses Thereof, and Methods of Making Same," published as U.S. Pub. No. 2003-0228275 A1 and U.S. Pat. No. 6,828,297 to Ekwuribe et al. entitled "Mixtures of Insulin Drug-Oligomer Conjugates Comprising Polyalkylene Glycol, Uses Thereof, and Methods of Making Same," published as U.S. Pub. No. 2003-0027748 A1. Oligomers according to embodiments of the present invention can be substantially monodispersed or monodispersed. Exemplary methods for synthesizing substantially monodispersed oligomers and monodispersed oligomers are provided in the Examples set forth herein.

In various embodiments described above, more than one oligomer (i.e., a plurality of oligomers) can be coupled to the insulin drug. The oligomers in the plurality can be the same. However, it is to be understood that the oligomers in the plurality can be different from one another, or, alternatively, some of the oligomers in the plurality can be the same and some can be different. When a plurality of oligomers is coupled to the insulin drug, one or more of the oligomers can be coupled to the insulin drug with hydrolyzable bonds and one or more of the oligomers can be coupled to the insulin drug with non-hydrolyzable bonds. Alternatively, all of the bonds coupling the plurality of oligomers to the insulin drug can be hydrolyzable, but have varying degrees of hydrolyzability such that, for example, one or more of the oligomers is rapidly removed from the insulin drug by hydrolysis in the body and one or more of the oligomers is slowly removed from the insulin drug by hydrolysis in the body.

The oligomer can be coupled to the insulin drug at various nucleophilic residues of the insulin drug including, but not limited to, nucleophilic hydroxyl functions and/or amino functions. When the insulin drug is a polypeptide, a nucleophilic hydroxyl function can be found, for example, at seine and/or tyrosine residues, and a nucleophilic amino function can be found, for example, at histidine and/or lysine residues, and/or at the one or more N-termini of the polypeptide. When an oligomer is coupled to the one or more N-termini of the insulin polypeptide, the coupling can form a secondary amine. When the insulin drug is human insulin, for example, the oligomer can be coupled to an amino functionality of the insulin, including the amino functionality of $Gly^{A1}$, the amino functionality of $Phe^{B1}$, and the amino functionality of $Lys^{B29}$. When one oligomer is coupled to the human insulin, the oligomer can be coupled to the amino functionality of $Lys^{B29}$. When two oligomers are coupled to the human insulin, the oligomers can be coupled to the amino functionality of $Phe^{B1}$ and the amino functionality of $Lys^{B29}$. While more than one oligomer can be coupled to the human insulin, a higher activity (improved glucose lowering ability) is observed for the mono-conjugated human insulin. Monoconjugates (i.e., when one oligomer is coupled to the insulin drug) can be prepared using methods described in U.S. Pat. No. 6,913,903, entitled "Methods of Synthesizing Insulin Polypeptide-Oligomer Conjugates, and Proinsulin Polypeptide-Oligomer Conjugates and Methods of Synthesizing Same," published as U.S. Pub. No. 2003-0087808, the disclosure of which is incorporated herein by reference in its entirety for the teaching of these methods.

According to other embodiments of the present invention, a pharmaceutical composition comprises i) an insulin and/or an insulin drug-oligomer conjugate and ii) a fatty acid component and a bile salt component, or a bile salt component without a fatty acid component. The insulin drug-oligomer conjugate includes an insulin drug covalently coupled to an oligomeric moiety. The fatty acid component includes a fatty acid, and the bile salt component includes a bile salt.

The insulin drug-oligomer conjugate includes an insulin drug covalently coupled to an oligomeric moiety, as described herein. The fatty acid component and the bile salt component, when together, can be present in a weight-to-weight ratio of any values between 1:15 and 15:1, and can be present, for example, in a weight-to-weight ratio of between 1:10 and 10:1, 1:5 and 5:1, 1:3 and 3:1 and/or 1:2 and 2:1.

According to the embodiments of the present invention, the fatty acid component is present in a first amount such that, at the precipitation point of the bile salt, the bile salt precipitates as first bile salt particles that, upon a return to a pH above the precipitation point of the bile salt, re-solubilize more quickly than second bile salt particles that would have precipitated if the fatty acid component were not present in the composition. The precipitation point of the bile salt in the formulation can be at or below a pH of 6.0, and can also be at or below a pH of 5.5. The pH above the precipitation point can be various pH values above the precipitation point. In some embodiments, the pH above the precipitation point is at least 0.5 pH units above the precipitation point. In other embodiments, the pH above the precipitation point is at least 0.8 pH units above the precipitation point.

In some embodiments, the first bile salt particles have an average diameter of less than 500 microns and the second bile salt particles have an average diameter of greater than 550 microns. In other embodiments, the first bile salt particles have an average diameter of less than 100 microns and the second bile salt particles have an average diameter of greater than 150 microns.

In some embodiments, the first bile salt particles are able to re-solubilize in less than 75% of the time it would have taken for the second bile salt particles to re-solubilize. In other embodiments, the first bile salt particles are able to re-solubilize in less than half the time it would have taken for the second bile salt particles to re-solubilize.

According to still other embodiments of the present invention, a pharmaceutical composition comprises an insulin drug-oligomer conjugate, between 0.1 and 15% (w/v) of a fatty acid component, and between 0.1 and 15% (w/v) of a bile salt component.

The insulin drug-oligomer conjugate may include an insulin drug covalently coupled to an oligomeric moiety as described herein. The fatty acid component and the bile salt component, when together, are present in a weight-to-weight ratio of any value between 1:15 and 15:1, and can be present, for example, in a weight-to-weight ratio of between 1:2 and 2:1.

According to certain embodiments of the present invention, the concentration of the fatty acid component is between a lower limit of 0.1, 0.2, 0.3, 0.4, 0.5, 0.6, 0.7, 0.8, 0.9, 1, 2, 3, 4, 5, 6, 7, 8, 9, 10, 11, 12, 13, or 14% (w/v) and an upper limit of 0.2, 0.3, 0.4, 0.5, 0.6, 0.7, 0.8, 0.9, 1, 2, 3, 4, 5, 6, 7, 8, 9, 10, 11, 12, 13, 14, or 15% (w/v). The concentration of the fatty acid component can be between 0.5 and 10% (w/v). between 0.5 and 5% (w/v), and/or between 1 and 3% (w/v).

According to certain embodiments of the present invention, the concentration of the bile acid component can be between a lower limit of 0.1, 0.2, 0.3, 0.4, 0.5, 0.6, 0.7, 0.8, 0.9, 1, 2, 3, 4, 5, 6, 7, 8, 9, 10, 11, 12, 13, or 14% (w/v) and an upper limit of 0.2, 0.3, 0.4, 0.5, 0.6, 0.7, 0.8, 0.9, 1, 2, 3, 4, 5, 6, 7, 8, 9, 10, 11, 12, 13, 14, or 15% (w/v). The concentration of the bile salt component can be between 0.5 and 10% (w/v), between 1 and 5% (w/v), and/or between 2 and 4% (w/v).

The present invention also provides a pharmaceutical composition comprising an insulin drug-oligomer conjugate comprising an insulin drug covalently coupled to an oligomeric moiety and a bile salt, in a pharmaceutically acceptable carrier.

Further provided herein is a pharmaceutical composition comprising, in a pharmaceutically acceptable carrier: an insulin drug; a bile salt, and a fatty acid, wherein the fatty acid and the bile salt are present in a weight-to-weight ratio of between 1:5 and 5:1, and wherein the fatty acid is present in an amount wherein the solubility of the bile salt in the presence of the fatty acid is greater than the solubility of the bile salt in a corresponding composition lacking the fatty acid.

The pharmaceutical compositions of this invention can comprise a bile salt that can be taurocholate, taurodeoxycholate, cholate, deoxycholate, glycodeoxycholate and/or mixtures thereof.

In some embodiments, the pharmaceutical composition of this invention can comprise bile salt that can be present in a concentration in the range of about 0.15% to about 10% bile salt and/or in the range of about 0.5% to about 5% bile salt.

The pharmaceutical compositions of this invention can have a pH of between 6.2 and 9.0 and can comprise a buffering component as described herein.

In certain embodiments, the pharmaceutical composition of this invention can be a liquid pharmaceutical composition, which can be suitable for oral administration. Alternatively, the pharmaceutical composition of this invention can be a solid dosage pharmaceutical composition.

The pharmaceutical composition of this invention in various embodiments can comprise a composition suitable for a route of administration comprising buccal, transdermal, peroral and/or nasal administration.

In some embodiments of the pharmaceutical composition of the present invention, the native insulin drug and/or the insulin drug oligomer conjugate can be an insulin polypeptide, which can be human insulin. In embodiments wherein the insulin is coupled to an oligomeric moiety, the moiety can be to the lysine at the B29 position of the human insulin. The insulin polypeptide can be an insulin analog including, but not limited to, $Gly^{A21}$ insulin, human; $Gly^{A21}$ $Gln^{B3}$ insulin, human; $Ala^{A21}$ insulin, human; $Ala^{A21}$ $Gln^{B3}$ insulin, human; $Gln^{B3}$ insulin, human; $Gln^{B30}$ insulin, human; $Gly^{A21}$ $Glu^{B30}$ insulin, human; $Gly^{A21}$ $Gln^{B3}$ $Glu^{B30}$ insulin, human; $Gln^{B3}$ $Glu^{B30}$ insulin, human; $Asp^{B28}$ insulin, human; $Lys^{B28}$ insulin, human; $Leu^{B28}$ insulin, human; $Val^{B28}$ insulin, human; $Ala^{B28}$ insulin, human; $Asp^{B28}$ $Pro^{B29}$ insulin, human; $Lys^{B28}$ $Pro^{B29}$ insulin, human; $Leu^{B28}$ $Pro^{B29}$ insulin, human; $Val^{B28}$ $Pro^{B29}$ insulin, human; $Ala^{B28}$ $Pro^{B29}$ insulin, human. An insulin analog of this invention can also comprise a B-chain with additional lysines added.

The pharmaceutical composition of this invention can comprise an insulin drug-oligomer conjugate that can be present as a substantially monodispersed mixture and/or as a monodispersed mixture.

In some embodiments, the pharmaceutical composition can comprise an insulin drug-oligomer conjugate that can be amphiphilically balanced. The oligomeric moiety can be hydrophilic (e.g., polyethylene glycol) and/or the oligomeric moiety can be lipophilic (e.g., alkane). In certain embodiments, the oligomeric moiety can comprise a hydrophilic moiety and a lipophilic moiety.

It is also contemplated that in various embodiments, the pharmaceutical compositions of this invention can comprise a fatty acid and a bile salt, wherein the fatty acid and the bile salt can be present in a weight to weight ratio of about 1:4, 1:3, 1:2 or 1:1.

The fatty acids of this invention can be one or more fatty acids and can be in the range of $C_4$ to $C_{20}$ and the fatty acids can be, but are not limited to lauric acid, capric acid, oleic acid and/or mixtures thereof.

In certain embodiments of the invention wherein the pharmaceutical composition comprises a fatty acid and a bile salt, the bile salt can be present in a range of about 0.5% to about 20% weight/volume and the fatty acid can be present in a range of about 0.2% to about 10% weight/volume. In some embodiments, the bile salt can be cholate and the fatty acid can be laurate and in some embodiments, the bile salt can be cholate and the cholate can be present in the amount of about 1.5% weight/volume and the fatty acid can be laurate and the laurate can be present in the amount of 2% weight/volume.

In certain embodiments, the fatty acid can be caprate and laurate and the bile salt and fatty acid can be present in the proportions of three parts bile salt, one part caprate and one part laurate.

The present invention additionally provides a method of treating an insulin deficiency in a subject in need of such treatment, said method comprising administering to the subject a therapeutically effective amount of a pharmaceutical composition of this invention.

The methods of this invention can comprise orally administering the pharmaceutical composition to the subject and/or administering the composition by buccal, transdermal, peroral and/or nasal administration.

In additional embodiments, the present invention provides herein a method of delivering an insulin drug and/or an insulin drug oligomer conjugate across the gut wall in a subject by simultaneously contacting the gut wall with 1) a bile salt and the insulin drug oligomer conjugate, 2) a bile salt and the insulin drug, 3) a bile salt, a fatty acid and the insulin drug oligomer conjugate, and/or 4) a bile salt, a fatty acid and the insulin drug, comprising administering to the subject the various pharmaceutical compositions of this invention comprising insulin drugs and/or insulin drug oligomer conjugates and comprising bile salts and fatty acids, or comprising bile salts, as described herein.

In some embodiments of the methods of delivering an insulin drug and/or an insulin drug/oligomer conjugate across the gut wall, the fatty acids can be laurate and caprate and the fatty acids and bile salts can be present in the pharmaceutical composition in the ratio of three parts bile salt, one part laurate and one part caprate.

Pharmaceutical compositions according to the present invention can further comprise a buffering component. The buffering component can comprise various buffering agents as will be understood by those skilled in the art. Exemplary buffering agents include, but are not limited to, inorganic acids (e.g., phosphoric acid), organic acids (e.g., citric acid), organic bases (e.g., tris-base (tris(hydroxymethyl)aminomethane), trolamine (triethanolamine), or histadine), and mixtures thereof. The buffering component can comprise an organic base, and can comprise tris-base, trolamine, phosphate and/or a mixture thereof. In some embodiments, the buffering component comprises an organic acid and an organic base, and can comprise citric acid and tris-base, trolamine, phosphate and/or a mixture thereof. The buffering agent can be present in an amount that will buffer the pharmaceutical composition against the acidic environment that may be experienced in the gut as will be understood by one skilled in the art.

In addition to the bile salt component and fatty acid component, pharmaceutical compositions according to embodiments of the present invention can include various suitable excipients as will be understood by those skilled in the art, such as those found in the *National Formulary* 19, pages 2404–2406 (2000), the disclosure of pages 2404 to 2406 being incorporated herein by reference in their entirety for these teachings. For example, the pharmaceutical compositions can include lubricating agents such as, for example, talc, magnesium stearate and mineral oil; wetting agents; emulsifying and suspending agents; binding agents such as starches, gum arabic, microcrystalline cellulose, cellulose, methylcellulose, and syrup; anticaking agents such as calcium silicate; coating agents such as methacrylates and shellac; preserving agents such as methyl- and propyl hydroxybenzoates; sweetening agents; or flavoring agents. Polyols, and inert fillers can also be used. Examples of polyols include, but are not limited to, mannitol, sorbitol, xylitol, sucrose, maltose, glucose, lactose, dextrose, and the like. Other inert fillers that can be used encompass those that are known in the art and are useful in the manufacture of various dosage forms. If desired, the solid formulations can include other components such as bulking agents and/or granulating agents, and the like. The drug products of the invention can be formulated so as to provide quick, sustained, or delayed release of the active ingredient after administration to a subject by employing procedures well known in the art.

The present invention also provides pharmaceutical compositions according to embodiments of the present invention that include those suitable for oral, rectal, topical, inhalation (e.g., via an aerosol) buccal (e.g., sub-lingual), vaginal, parenteral (e.g., subcutaneous, intramuscular, intradermal, intraarticular, intrapleural, intraperitoneal, intracerebral, intraarterial, or intravenous), topical (i.e., both skin and mucosal surfaces, including airway surfaces) and transdermal administration, although the most suitable route in any given case will depend on the nature and severity of the condition being treated and on the nature of the particular insulin drug-oligomer conjugate which is being used.

Pharmaceutical compositions suitable for oral administration can be presented in discrete units, such as capsules, cachets, lozenges, or tables, each containing a predetermined amount of the insulin drug-oligomer conjugates; as a powder or granules; as a solution or a suspension in an aqueous or non-aqueous liquid; or as an oil-in-water or water-in-oil emulsion. Such formulations can be prepared by any suitable method of pharmacy which includes the step of bringing into association the insulin drug-oligomer conjugate, the fatty acid component, the bile salt component, and a suitable carrier (which can contain one or more accessory ingredients as noted above). In general, the pharmaceutical composition according to embodiments of the present invention are prepared by uniformly and intimately admixing the insulin drug-oligomer conjugate, the fatty acid component, and the bile salt component with a liquid or finely divided solid carrier, or both, and then, if necessary, shaping the resulting mixture.

In some embodiments of the present invention, the pharmaceutical composition is a liquid pharmaceutical composition suitable for oral administration. When the pharmaceutical composition is a liquid pharmaceutical composition, the composition can include a buffering agent as described above. Liquid pharmaceutical compositions according to embodiments of the present invention have a pH that is physiologically compatible. Liquid pharmaceutical compositions according to embodiments of the present invention can have a pH that is between 6.2 and 9.0. In some embodiments, liquid pharmaceutical compositions according to embodiments of the present invention have a pH that is between a lower limit of 6.3, 6.4, 6.5, 6.6, 6.7, 6.8, 6.9, 7.0, 7.1, 7.2, 7.3, 7.4, 7.5, 7.6, or 7.7 and an upper limit of 7.9, 8.0, 8.1, 8.2, 8.3, 8.4, 8.5, 8.6, 8.7, 8.8, or 8.9. In some embodiments, liquid pharmaceutical compositions according to embodiments of the present invention have a pH that is between 7.0 and 8.5. In other embodiments, liquid pharmaceutical compositions according to embodiments of the present invention have a pH that is between 7.4 and 8.2.

In other embodiments of the present invention, the pharmaceutical composition is a solid pharmaceutical composition suitable for oral administration. The solid pharmaceutical composition can be prepared by various methods as will be understood by those skilled in the art. For example, a tablet can be prepared by compressing or molding a powder or granules containing the insulin drug-oligomer conjugate, the fatty acid component, the bile salt component, optionally with one or more accessory ingredients. Compressed tablets can be prepared by compressing, in a suitable machine, the mixture in a free-flowing form, such as a powder or granules optionally mixed with a binder, lubricant, inert diluent, and/or surface active/dispersing agent(s). Molded tablets can be made by molding, in a suitable machine, the powdered compound moistened with an inert liquid binder.

Pharmaceutical compositions suitable for buccal (sublingual) administration include lozenges comprising the insulin and/or the insulin drug-oligomer conjugate, the fatty acid component, and the bile salt component or the bile salt component in the absence of a fatty acid component, in a flavored base, usually an artificial sweetener and acacia or tragacanth; and pastilles comprising the insulin and/or the insulin drug-oligomer conjugate, the fatty acid component, and the bile salt component, or the bile salt component alone, in an inert base such as gelatin and glycerin or sucrose and acacia.

Pharmaceutical compositions according to embodiments of the present invention suitable for parenteral administration can comprise sterile aqueous and non-aqueous injection solutions comprising the insulin and/or the insulin drug-oligomer conjugate, the fatty acid component, and the bile salt component, or the bile salt component without a fatty acid component, which preparations can be isotonic with the blood of the intended recipient. These preparations can contain anti-oxidants, buffers, bacteriostats and solutes that render the composition isotonic with the blood of the intended recipient. Aqueous and non-aqueous sterile suspensions can include suspending agents and thickening agents. The compositions can be presented in unit/dose or multi-dose containers, for example sealed ampoules and vials, and can be stored in a freeze-dried (lyophilized) condition requiring only the addition of the sterile liquid carrier, for example, saline or water-for-injection immediately prior to use.

Extemporaneous injection solutions and suspensions can be prepared from sterile powders, granules and tablets of the kind previously described. For example, an injectable, stable, sterile composition comprising the insulin and/or the insulin drug-oligomer conjugate, the fatty acid component, and the bile salt component or the bile salt component alone, in a unit dosage form in a sealed container can be provided. The mixture of the insulin and/or the insulin drug-oligomer conjugate, the fatty acid component, and the bile salt component or the bile salt component alone, is provided in the form of a lyophilizate which is capable of being reconstituted with a suitable pharmaceutically acceptable carrier to form a liquid composition suitable for injection thereof into a subject.

As used herein, a "pharmaceutically acceptable carrier" according to the present invention is a component such as a carrier, diluent, or excipient of a composition that is compatible with the other ingredients of the composition in that it can be combined with the compounds and/or compositions of the present invention without eliminating the biological activity of the compounds or the compositions, and is suitable for use in subjects as provided herein without undue adverse side effects (such as toxicity, irritation, allergic response, and death). Side effects are "undue" when their risk outweighs the benefit provided by the pharmaceutical composition. Non-limiting examples of pharmaceutically acceptable components include, without limitation, any of the standard pharmaceutical carriers such as phosphate buffered saline solutions, water, emulsions such as oil/water emulsions or water/oil emulsions, microemulsions, and various types of wetting agents.

The unit dosage form of the compositions of this invention can range from about 10 mg to about 10 grams of insulin and/or the insulin drug-oligomer conjugate. When the insulin and/or insulin drug-oligomer conjugate is substantially water-insoluble, a sufficient amount of emulsifying agent that is physiologically acceptable can be employed in sufficient quantity to emulsify the insulin drug-oligomer conjugate in an aqueous carrier. One such useful emulsifying agent is phosphatidyl choline.

Pharmaceutical compositions suitable for rectal administration can be presented as unit dose suppositories. These can be prepared by admixing the insulin and/or the insulin drug-oligomer conjugate, the fatty acid component, and the bile salt component or the bile salt component alone, with one or more conventional solid carriers, for example, cocoa butter, and then shaping the resulting mixture.

Pharmaceutical compositions suitable for topical application to the skin can take the form of an ointment, cream, lotion, paste, gel, spray, aerosol, transdermal patch or oil. Carriers that can be used include, but are not limited to, petroleum jelly, lanoline, polyethylene glycols, alcohols, transdermal enhancers, and combinations of two or more thereof.

Pharmaceutical compositions suitable for transdermal administration can be presented as discrete patches adapted to remain in intimate contact with the epidermis of the recipient for a prolonged period of time. Compositions suitable for transdermal administration can also be delivered by iontophoresis (see, for example, *Pharmaceutical Research* 3 (6):318 (1986)) and typically take the form of an optionally buffered aqueous solution of the insulin and/or the insulin drug-oligomer conjugate, the fatty acid component, and the bile salt component, or the bile salt component alone. Suitable formulations comprise citrate or bis/tris buffer (pH 6) or ethanol/water and can contain, for example, from 0.1 to 0.2M active ingredient.

Methods of treating an insulin deficiency in a subject in need of such treatment by administering a therapeutically effective amount of any of the various pharmaceutical compositions of the present invention are also provided. The effective amount of insulin and/or of the insulin drug-oligomer conjugate, the use of which is in the scope of present invention, will vary somewhat from conjugate to conjugate, and subject to subject, and will depend, for example, upon factors such as the age and condition of the subject, the severity of the condition to be treated and/or the route of delivery. An appropriate "therapeutically effective amount" in any individual case can be determined by one of ordinary skill in the art by reference to the pertinent texts and literature and/or by using routine experimentation. (See, for example, Remington, *The Science And Practice of Pharmacy* (9$^{th}$ Ed. 1995).

A subject of this invention can be any animal that produces insulin and is therefore susceptible to disorders related to a deficiency of insulin and that would be able to be treated with the compositions of this invention. The subject can be any mammal and the mammal can be a human.

As an example, a dosage of from about 1.0 µg/kg to about 50 mg/kg, including any dosage range between these values, will have therapeutic efficacy, with all weights being calculated based upon the weight of the insulin and/or the insulin drug-oligomer conjugate. Toxicity concerns at the higher level may restrict intravenous dosages to a lower level such as up to about 10 mg/kg, with all weights being calculated based upon the weight of the active base. A dosage of from about 10 mg/kg to about 50 mg/kg can be employed for oral administration. Typically, a dosage of from about 0.5 mg/kg to 5 mg/kg can be employed for intramuscular injection. The frequency of administration can be, for example, one, two, three or more times per day or as necessary to control the condition. Control of the condition and efficacy of the treatment can be readily determined by those skilled in the art of studying and/or treating insulin deficiencies and/or related disorders. Alternatively, the pharmaceutical compositions of this invention can be administered by continuous infusion. The duration of treatment depends on the type of insulin deficiency being treated and can be for as long as the life of the subject.

In another aspect of the present invention, a method of providing a pharmaceutical composition is provided herein, which comprises selecting an amount of a bile salt to include in the composition based on the ability of the bile salt to increase the solubility of a fatty acid component when the composition has a pH of 8.5 or less.

According to other embodiments of the present invention, a method of providing a pharmaceutical composition is provided herein, which comprises selecting an amount of a fatty acid to include in the composition based on the ability of the fatty acid to lower the precipitation point of a bile salt component in the composition to a pH of 5.5 or less.

According to still other embodiments of the present invention, a method of providing a pharmaceutical composition is provided herein, which comprises selecting an amount of a fatty acid to include in the composition based on the ability of the fatty acid to alter the precipitation characteristics of a bile salt component in the composition.

The present invention will now be described with reference to the following examples. It should be appreciated that these examples are for the purposes of illustrating aspects of the present invention, and do not limit the scope of the invention as defined by the claims.

EXAMPLES

Example 1

Synthesis of 6-(2-{2-[2-(2-{2-[2-(2-methoxyethoxy) ethoxy]-ethoxy}-ethoxy) -ethoxy]-ethoxy}-ethoxy)-hexanoic acid 2,5-dioxo-pyrrolidin-1-yl ester (8)

Hexaethylene glycol monobenzyl ether (1). An aqueous sodium hydroxide solution prepared by dissolving 3.99 g (100 mmol) NaOH in 4 ml water was added slowly to monodispersed hexaethylene glycol (28.175 g, 25 ml, 100 mmol). Benzyl chloride (3.9 g, 30.8 mmol, 3.54 ml) was added and the reaction mixture was heated with stirring to 100° C. for 18 hours. The reaction mixture was then cooled, diluted with brine (250 ml) and extracted with methylene chloride (200 ml×2). The combined organic layers were washed with brine once, dried over $Na_2SO_4$, filtered and concentrated in vacuo to a dark brown oil. The crude product mixture was purified via flash chromatography (silica gel, gradient elution: ethyl acetate to 9/1 ethyl acetate/methanol) to yield 8.099 g (70%) of monodispersed compound 1 as a yellow oil.

Ethyl 6-methylsulfonyloxyhexanoate (2). A solution of monodispersed ethyl 6-hydroxyhexanoate (50.76 ml, 50.41 g, 227 mmol) in dry dichloromethane (75 ml) was chilled in an ice bath and placed under a nitrogen atmosphere. Triethylamine (34.43 ml, 24.99 g, 247 mmol) was added. A solution of methanesulfonyl chloride (19.15 ml, 28.3 g, 247 mmol) in dry dichloromethane (75 ml) was added dropwise from an addition funnel. The mixture was stirred for three and one half hours, slowly being allowed to come to room temperature as the ice bath melted. The mixture was filtered through silica gel, and the filtrate was washed successively with water, saturated $NaHCO_3$, water and brine. The organics were dried over $Na_2SO_4$, filtered and concentrated in vacuo to a pale yellow oil. Final purification of the crude product was achieved by flash chromatography (silica gel, 1/1 hexanes/ethyl acetate) to give the monodispersed compound 2 (46.13 g, 85%) as a clear, colorless oil. FAB MS: m/e 239 (M+H), 193 (M—$C_2H_5O$).

6-{2-[2-(2-{2-[2-(2-Benzyloxyethoxy)ethoxy]ethoxy}-ethoxy)-ethoxy]-ethoxy}-hex acid ethyl ester (3). Sodium hydride (3.225 g or a 60% oil dispersion, 80.6 mmol) was suspended in 80 ml of anhydrous toluene, placed under a nitrogen atmosphere and cooled in an ice bath. A solution of the monodispersed alcohol 9 (27.3 g, 73.3 mmol) in 80 ml dry toluene was added to the NaH suspension. The mixture was stirred at 0° C. for thirty minutes, allowed to come to room temperature and stirred for another five hours, during which time the mixture became a clear brown solution. The monodispersed mesylate 10 (19.21 g, 80.6 mmol) in 80 ml dry toluene was added to the NaH/alcohol mixture, and the combined solutions were stirred at room temperature for three days. The reaction mixture was quenched with 50 ml methanol and filtered through basic alumina. The filtrate was concentrated in vacuo and purified by flash chromatography (silica gel, gradient elution: 3/1 ethyl acetate/hexanes to ethyl acetate) to yield the monodispersed compound 3 as a pale yellow oil (16.52 g, 44%). FAB MS: m/e 515 (M+H).

6-{2-[2-(2-{2-[2-(2-hydroxyethoxy)ethoxy]ethoxy}-ethoxy)-ethoxy]-ethoxy}-hexan acid ethyl ester (4). Substantially monodispersed benzyl ether 3 (1.03 g, 2.0 mmol) was dissolved in 25 ml ethanol. To this solution was added 270 mg 10% Pd/C, and the mixture was placed under a hydrogen atmosphere and stirred for four hours, at which time TLC showed the complete disappearance of the starting material. The reaction mixture was filtered through Celite 545 to remove the catalyst, and the filtrate was concentrated in vacuo to yield the monodispersed compound 4 as a clear oil (0.67 g, 79%). FAB MS: m/e 425 (M+H), 447 (M+Na).

6-{2-[2-(2-{2-[2-(2-methylsulfonylethoxy)ethoxy]ethoxy}-ethoxy)-ethoxy]-ethoxy}acid ethyl ester (5). The monodispersed alcohol 4 (0.835 g, 1.97 mmol) was dissolved in 3.5 ml dry dichloromethane and placed under a nitrogen atmosphere. Triethylamine (0.301 ml, 0.219 g, 2.16 mmol) was added and the mixture was chilled in an ice bath. After two minutes, the methanesulfonyl chloride (0.16 ml, 0.248 g, 2.16 mmol) was added. The mixture was stirred for 15 minutes at 0° C., then at room temperature for two hours. The reaction mixture was filtered through silica gel to remove the triethylammonium chloride, and the filtrate was washed successively with water, saturated $NaHCO_3$, water and brine. The organics were dried over $Na_2SO_4$, filtered and concentrated in vacuo. The residue was purified by column chromatography (silica gel, 9/1 ethyl acetate/methanol) to give monodispersed compound 5 as a clear oil (0.819 g, 83%). FAB MS: m/e 503 (M+H).

6-(2-{2-[2-(2-{2-[2-(2-methoxyethoxy)ethoxy]-ethoxy}-ethoxy)-ethoxy]-ethoxy}-hexanoic acid ethyl ester (6). NaH (88 mg of a 60% dispersion in oil, 2.2 mmol) was suspended in anhydrous toluene (3 ml) under $N_2$ and chilled to 0° C. Monodispersed diethylene glycol monomethyl ether (0.26 ml, 0.26 g, 2.2 mmol) that had been dried via azeotropic distillation with toluene was added. The reaction mixture was allowed to warm to room temperature and stirred for four hours, during which time the cloudy grey suspension became clear and yellow and then turned brown. Mesylate 5 (0.50 g, 1.0 mmol) in 2.5 ml dry toluene was added. After stirring at room temperature over night, the reaction was quenched by the addition of 2 ml of methanol and the resultant solution was filtered through silica gel. The filtrate was concentrated in vacuo and the FAB MS: m/e 499 (M+H), 521 (M+Na). Additional purification by preparatory chromatography (silica gel, 19/3 chloroform/methanol) provided the monodispersed compound 6 as a clear yellow oil (0.302 g 57%). FAB MS: m/e 527 (M+H), 549 (M+Na).

6-(2-{2-[2-(2-{2-[2-(2-methoxyethoxy)ethoxy]-ethoxy}-ethoxy)-ethoxy]-ethoxy}-ethoxy)-hexanoic acid (7). Monodispersed ester 6 (0.25 g, 0.46 mmol) was stirred for 18 hours in 0.71 ml of 1 N NaOH. After 18 hours, the mixture was concentrated in vacuo to remove the alcohol and the residue dissolved in a further 10 ml of water. The aqueous solution was acidified to pH 2 with 2 N HCl and the product was extracted into dichloromethane (30 ml×2). The combined organics were then washed with brine (25 ml×2), dried over $Na_2SO_4$, filtered and concentrated in vacuo to yield the monodispersed compound 15 as a yellow oil (0.147 g, 62%). FAB MS: m/e 499 (M+H), 521 (M+Na).

6-(2-{2-[2-(2-{2-[2-(2-methoxyethoxy)ethoxy]-ethoxy}-ethoxy)-ethoxy]-ethoxy}-ethoxy)-hexanoic acid 2,5-dioxopyrrolidin-1-yl ester (8). Monodispersed acid 7 (0.209 g, 0.42 mmol) was dissolved in 4 ml of dry dichloromethane and added to a dry flask already containing NHS (N-hydroxysuccinimide) (57.8 mg, 0.502 mmol) and EDC (1-(3-dimethylaminopropyl)-3-ethylcarbodiimid hydrochloride) (98.0 mg, 0.502 mmol) under a $N_2$ atmosphere. The solution was stirred at room temperature overnight and filtered through silica gel to remove excess reagents and the urea formed from the EDC. The filtrate was concentrated in vacuo to provide the activated monodispersed oligomer 8 as a dark yellow oil (0.235 g, 94%). FAB MS: m/e 596 (M+H), 618 (M+Na).

Example 2

Synthesis of Activated $MPEG_7$-$C_8$ (14)

Mesylate of triethylene glycol monomethyl ether (9). To a solution of $CH_2Cl_2$ (100 mL) cooled to 0° C. in an ice bath was added monodispersed triethylene glycol monomethyl ether (25 g, 0.15 mol). Then triethylamine (29.5 mL, 0.22 mol) was added and the solution was stirred for 15 min at 0° C., which was followed by dropwise addition of methanesulfonyl chloride (13.8 mL, 0.18 mol, dissolved in 20 mL $CH_2Cl_2$). The reaction mixture was stirred for 30 min at 0° C., allowed to warm to room temperature, and then stirred for 2 h. The crude reaction mixture was filtered through Celite (washed $CH_2Cl_2$~200 mL), then washed with $H_2O$ (300 mL), 5% $NaHCO_3$ (300 mL), $H_2O$ (300 mL), sat. NaCl (300 mL), dried $MgSO_4$, and evaporated to dryness. The oil was then placed on a vacuum line for ~2h to ensure dryness and afforded the monodispersed compound 9 as a yellow oil (29.15 g, 80% yield).

Heptaethylene glycol monomethyl ether (10). To a solution of monodispersed tetraethylene glycol (51.5 g, 0.27 mol) in THF (1L) was added potassium t-butoxide (14.8 g, 0.13 mol, small portions over ~30 min). The reaction mixture was then stirred for 1h and then 9 (29.15 g, 0.12 mol) dissolved in THF (90 mL) was added dropwise and the reaction mixture was stirred overnight. The crude reaction mixture was filtered through Celite (washed $CH_2Cl_2$,~200 mL) and evaporated to dryness. The oil was then dissolved in HCl (250 mL, 1 N) and washed with ethyl acetate (250 mL) to remove excess 9. Additional washings of ethyl acetate (125 mL) may be required to remove remaining 9. The aqueous phase was washed repetitively with $CH_2Cl_2$ (125 mL volumes) until most of the compound 18 has been removed from the aqueous phase. The first extraction will contain 9, 10, and dicoupled side product and should be back extracted with HCl (125 mL, 1N). The organic layers were combined and evaporated to dryness. The resultant oil was then dissolved in $CH_2Cl_2$ (100 mL) and washed repetitively with $H_2O$ (50 mL volumes) until 10 was removed. The aqueous fractions were combined, total volume 500 mL, and NaCl was added until the solution became cloudy and then was washed with $CH_2Cl_2$ (2×500 mL). The organic layers were combined, dried $MgSO_4$, and evaporated to dryness to afford the monodispersed compound 10 as an oil (16.9 g, 41% yield). It may be desirable to repeat one or more steps of the purification procedure to ensure high purity.

8-Bromooctoanate (11). To a solution of monodispersed 8-bromooctanoic acid (5.0 g, 22 mmol) in ethanol (100 mL) was added $H_2SO_4$ (0.36 mL, 7.5 mmol) and the reaction was heated to reflux with stirring for 3 h. The crude reaction mixture was cooled to room temperature and washed $H_2O$ (100 mL), sat. $NaHCO_3$ (2×100 mL), $H_2O$ (100 mL), dried $MgSO_4$, and evaporated to dryness to afford a clear oil 11 (5.5 g, 98% yield).

$MPEG_7$-$C_8$ ester (12). To a solution of the monodispersed compound 10 (3.0 g, 8.8 mmol) in ether (90 mL) was added potassium t-butoxide (1.2 g, 9.6 mmol) and the reaction mixture was stirred for 1 h. Then dropwise addition of the monodispersed compound 11 (2.4 g, 9.6 mmol), dissolved in ether (10 mL), was added and the reaction mixture was stirred overnight. The crude reaction mixture was filtered through Celite (washed $CH_2Cl_2$,~200 mL) and evaporated to dryness. The resultant oil was dissolved in ethyl acetate and washed $H_2O$ (2×200 mL), dried $MgSO_4$, and evaporated to dryness. Column chromatography (Silica, ethyl acetate to ethyl acetate/methanol, 10:1) was performed and afforded the monodispersed compound 12 as a clear oil (0.843 g, 19% yield).

$MPEG_7$-$C_8$ acid (13). To the oil of the monodispersed compound 12 (0.70 g, 1.4 mmol) was added 1N NaOH (2.0 mL) and the reaction mixture was stirred for 4 h. The crude reaction mixture was concentrated, acidified (pH~2), saturated with NaCl, and washed $CH_2Cl_2$ (2×50 mL). The organic layers were combined, washed sat. NaCl, dried $MgSO_4$, and evaporated to dryness to afford the monodispersed compound 13 as a clear oil (0.35 g, 53% yield).

Activation of $MPEG_7$-$C_8$ acid. Monodispersed mPEG7-C8-acid 13 (0.31 g, 0.64 mmol) was dissolved in 3 ml of anhydrous methylene chloride and then solution of N-hydroxysuccinimide (0.079 g, 0.69 mmol) and EDCI·HCl (135.6 mg, 0.71 mmol) in anhydrous methylene chloride added. Reaction was stirred for several hours, then washed with 1N HCl, water, dried over $MgSO_4$, filtered and concentrated. Crude material was purified by column chromatography, concentrated to afford monodispersed activated $MPEG_7$-$C_8$ 14 as a clear oil and dried via vacuum.

Example 3

Synthesis of Activated $MPEG_7$-$C_{10}$ (19)

10-hydroxydecanoate (15). To a solution of monodispersed 10-hydroxydecanoic acid (5.0 g, 26.5 mmol) in ethanol (100 mL) was added $H_2SO_4$ (0.43 mL, 8.8 mmol) and the reaction was heated to reflux with stirring for 3 h. The crude reaction mixture was cooled to room temperature and washed $H_2O$ (100 mL), sat. $NaHCO_3$ (2×100 mL), $H_2O$ (100 mL), dried $MgSO_4$, and evaporated to dryness to afford the monodispersed compound 15 as a clear oil (6.9 g, 98% yield).

Mesylate of 10-hydroxydecanoate (16). To a solution of $CH_2Cl_2$ (27 mL) was added monodispersed 10-hydroxydecanoate 15 (5.6 g, 26 mmol) and cooled to 0° C. in an ice bath. Then triethylamine (5 mL, 37 mmol) was added and the reaction mixture was stirred for 15 min at 0° C. Then methanesulfonyl chloride (2.7 mL, 24 mmol) dissolved in $CH_2Cl_2$ (3 mL) was added and the reaction mixture was stirred at 0° C. for 30 min, the ice bath was removed and the reaction was stirred for an additional 2 h at room temperature. The crude reaction mixture was filtered through Celite (washed $CH_2Cl_2$, 80 mL) and the filtrate was washed $H_2O$ (100 mL), 5% $NaHCO_3$ (2×100 mL), $H_2O$ (100 mL), sat. NaCl (100 mL), dried $MgSO_4$, and evaporated to dryness to afford the monodispersed compound 16 as a yellowish oil (7.42 g, 97% yield).

$MPEG_7$-$C_{10}$ Ester (17). To a solution of substantially monodispersed heptaethylene glycol monomethyl ether 10 (2.5 g, 7.3 mmol) in tetrahydrofuran (100 mL) was added sodium hydride (0.194 g, 8.1 mmol) and the reaction mixture was stirred for 1 h. Then dropwise addition of mesylate of monodispersed 10-hydroxydecanoate 16 (2.4 g, 8.1 mmol), dissolved in tetrahydrofuran (10 mL), was added and the reaction mixture was stirred overnight. The crude reaction mixture was filtered through Celite (washed $CH_2Cl_2$, ~200 mL) and evaporated to dryness. The resultant oil was dissolved in ethyl acetate and washed $H_2O$ (2×200 mL), dried $MgSO_4$, evaporated to dryness, chromatographed (silica, ethyl acetate/methanol, 10:1), and chromatographed (silica, ethyl acetate) to afford the monodispersed compound 17 as a clear oil (0.570 g, 15% yield).

$MPEG_7$-$C_{10}$ Acid (18). To the oil of monodispersed $mPEG_7$-$C_{10}$ ester 17 (0.570 g, 1.1 mmol) was added 1N NaOH (1.6 mL) and the reaction mixture was stirred overnight. The crude reaction mixture was concentrated, acidified (pH~2), saturated with NaCl, and washed $CH_2Cl_2$ (2×50 mL). The organic layers were combined, washed sat. NaCl (2×50 mL), dried $MgSO_4$, and evaporated to dryness to afford the monodispersed compound 18 as a clear oil (0.340 g, 62% yield).

Activation of $MPEG_7$-$C_{10}$ Acid. The monodispersed acid 18 was activated using procedures as described herein to provide activated $MPEG_7$-$C_{10}$ Oligomer 19.

Example 4

Synthesis of Activated $C_{18}(PEG_6)$ Oligomer (22)

Synthesis of $C_{18}(PEG_6)$ Oligomer (20). Monodispersed stearoyl chloride (0.7 g, 2.31 mmol) was added slowly to a mixture of monodispersed $PEG_6$ (5 g, 17.7 mmol) and pyridine (0.97 g, 12.4 mmol) in benzene. The reaction mixture was stirred for several hours (~5). The reaction was followed by TLC using ethylacetate/methanol as a developing solvent. Then the reaction mixture was washed with water, dried over MgSO$_4$, concentrated and dried via vacuum. Purified monodispersed compound 20 was analyzed by FABMS: m/e 549/M$^+$H.

Activation of C$_{18}$(PEG$_6$) Oligomer. Activation of monodispersed C$_{18}$(PEG$_6$) oligomer was accomplished in two steps:

1) Monodispersed stearoyl-PEG$_6$20 (0.8 g, 1.46 mmol) was dissolved in toluene and added to a phosgene solution (10 ml, 20% in toluene) which was cooled with an ice bath. The reaction mixture was stirred for 1 h at 0° C. and then for 3 h at room temperature. Then phosgene and toluene were distilled off and the remaining substantially monodispersed stearoyl PEG6 chloroformate 21 was dried over P$_2$O$_5$ overnight.

2) To a solution of monodispersed stearoyl-PEG$_6$ chloroformate 21 (0.78 g, 1.27 mmol) and TEA (128 mg, 1.27 mmol) in anhydrous methylene chloride, N-hydroxy succinimide (NHS) solution in methylene chloride was added. The reaction mixture was stirred for 16 hours, then washed with water, dried over MgSO$_4$, filtered, concentrated and dried via vacuum to provide the monodispersed activated C$_{18}$(PEG$_6$) oligomer 22.

Example 5

Synthesis of Activated C$_{18}$(PEG$_8$) Oligomer (28)

Tetraethylene glycol monobenzylether (23). To the oil of monodispersed tetraethylene glycol (19.4 g, 0.10 mol) was added a solution of NaOH (4.0 g in 4.0 mL) and the reaction was stirred for 15 mm. Then benzyl chloride (3.54 mL, 30.8 mmol) was added and the reaction mixture was heated to 100° C. and stirred overnight. The reaction mixture was cooled to room temperature, diluted with sat. NaCl (250 mL), and washed CH$_2$Cl$_2$ (2×200 mL). The organic layers were combined, washed sat. NaCl, dried MgSO$_4$, and chromatographed (silica, ethyl acetate) to afford the monodispersed compound 23 as a yellow oil (6.21 g, 71% yield).

Mesylate of tetraethylene glycol monobenzylether (24). To a solution of CH$_2$Cl$_2$ (20 mL) was added monodispersed tetraethylene glycol monobenzylether 23 (6.21 g, 22 mmol) and cooled to 0° C. in an ice bath. Then triethylamine (3.2 mL, 24 mmol) was added and the reaction mixture was stirred for 15 min at 0° C. Then methanesulfonyl chloride (1.7 mL, 24 mmol) dissolved in CH$_2$Cl$_2$ (2 mL) was added and the reaction mixture was stirred at 0° C. for 30 min, the ice bath was removed and the reaction was stirred for an additional 2 h at room temperature. The crude reaction mixture was filtered through Celite (washed CH$_2$Cl$_2$, 80 mL) and the filtrate was washed H$_2$O (100 mL), 5% NaHCO$_3$ (2×100 mL), H$_2$O (100 mL), sat. NaCl (100 mL), and dried MgSO$_4$. The resulting yellow oil was chromatographed on a pad of silica containing activated carbon (10 g) to afford the monodispersed compound 24 as a clear oil (7.10 g, 89% yield).

Octaethylene glycol monobenzylether (25). To a solution of tetrahydrofuran (140 mL) containing sodium hydride (0.43 g, 18 mmol) was added dropwise a solution of monodispersed tetraethylene glycol (3.5 g, 18 mmol) in tetrahydrofuran (10 mL) and the reaction mixture was stirred for 1 h. Then mesylate of monodispersed tetraethylene glycol monobenzylether 24 (6.0 g, 16.5 mmol) dissolved in tetrahydrofuran (10 mL) was added dropwise and the reaction mixture was stirred overnight. The crude reaction mixture was filtered through Celite (washed, CH$_2$Cl$_2$, 250 mL) and the filtrate was washed H$_2$O, dried MgSO$_4$, and evaporated to dryness. The resultant oil was chromatographed (silica, ethyl acetate/methanol, 10:1) and chromatographed (silica, chloroform/methanol, 25:1) to afford the monodispersed compound 25 as a clear oil (2.62 g, 34% yield).

Synthesis of Stearate PEG$_8$-Benzyl (26). To a stirred cooled solution of monodispersed octaethylene glycol monobenzylether 25 (0.998 g, 2.07 mmol) and pyridine (163.9 mg, 2.07 mmol) was added monodispersed stearoyl chloride (627.7 mg, 2.07 mmol) in benzene. The reaction mixture was stirred overnight (18 hours). The next day the reaction mixture was washed with water, dried over MgSO$_4$, concentrated and dried via vacuum. Then the crude product was chromatographed on flash silica gel column, using 10% methanol/90% chloroform. The fractions containing the product were combined, concentrated and dried via vacuum to afford the monodispersed compound 26.

Hydrogenolysis of Stearate-PEG$_8$-Benzyl. To a methanol solution of monodispersed stearate-PEG$_8$-Bzl 26 (0.854 g 1.138 mmol ) Pd/C(10%) (palladium, 10% wt. on activated carbon) was added. The reaction mixture was stirred overnight (18 hours) under hydrogen. Then the solution was filtered, concentrated and purified by flash column chromatography using 10% methanol/90% chloroform, fractions with R$_f$=0.6 collected, concentrated and dried to provide the monodispersed acid 27.

Activation of C$_{18}$(PEG$_8$) Oligomer. Two step activation of monodispersed stearate-PEG8 oligomer 27 was performed as described for stearate-PEG$_6$ in Example 4 above to provide the monodispersed activated C$_{18}$(PEG$_8$) oligomer 28.

Example 6

Synthesis of Activated Triethylene Glycol Mono methyl Oligomers

A solution of toluene containing 20% phosgene (100 ml, approximately 18.7 g, 189 mmol phosgene) was chilled to 0° C. under a N$_2$ atmosphere. Monodispersed mTEG (triethylene glycol, monomethyl ether, 7.8 g, 47.5 mmol) was dissolved in 25 mL anhydrous ethyl acetate and added to the chilled phosgene solution. The mixture was stirred for one hour at 0° C., then allowed to warm to room temperature and stirred for another two and one half hours. The remaining phosgene, ethyl acetate and toluene were removed via vacuum distillation to leave the monodispersed mTEG chloroformate as a clear oily residue.

The monodispersed nTEG chloroformate was dissolved in 50 mL of dry dichloromethane to which was added TEA (triethyleamine, 6.62 mL, 47.5 mmol) and NHS (N-hydroxysuccinimide, 5.8 g, 50.4 mmol). The mixture was stirred at room temperature under a dry atmosphere for twenty hours during which time a large amount of white precipitate appeared. The mixture was filtered to remove this precipitate and concentrated in vacuo. The resultant oil was taken up in dichloromethane and washed twice with cold deionized water, twice with 1N HCl and once with brine. The organics were dried over MgSO$_4$, filtered and concentrated to provide the monodispersed title compound as a clear, light yellow oil. If necessary, the NHS ester could be further purified by flash chromatography on silica gel using EtOAc as the elutant.

Example 7

Synthesis of Activated Palmitate-TEG Oligomers

Monodispersed palmitic anhydride (5 g; 10 mmol) was dissolved in dry THF (20 mL) and stirred at room temperature. To the stirring solution, 3 mol excess of pyridine was added followed by monodispersed triethylene glycol (1.4 mL). The reaction mixture was stirred for 1 hour (progress of the reaction was monitored by TLC; ethyl acetate-chloroform; 3:7). At the end of the reaction, THF was removed and the product was mixed with 10% $H_2SO_4$ acid and extracted ethyl acetate (3×30 mL). The combined extract was washed sequentially with water, brine, dried over $MgSO_4$, and evaporated to give monodispersed palmitate-TEG oligomers.

A solution of N,N'-disuccinimidyl carbonate (3 mmol) in DMF (~10 mL) is added to a solution of the monodispersed palmitate-TEG oligomers (1 mmol) in 10 mL of anhydrous DMF while stirring. Sodium hydride (3 mmol) is added slowly to the reaction mixture. The reaction mixture is stirred for several hours (e.g., 5 hours). Diethyl ether is added to precipitate the monodispersed activated title oligomer. This process is repeated 3 times and the product is finally dried.

Example 8

Synthesis of Activated Hexaethylene Glycol Monomethyl Oligomers

Monodispersed activated hexaethylene glycol monomethyl ether was prepared analogously to that of monodispersed triethylene glycol as described herein. A 20% phosgene in toluene solution (35 mL, 6.66 g, 67.4 mmol phosgene) was chilled under a $N_2$ atmosphere in an ice/salt water bath. Monodispersed hexaethylene glycol (1.85 mL, 2.0 g, 6.74 mmol) was dissolved in 5 mL anhydrous EtOAc and added to the phosgene solution via syringe. The reaction mixture was kept stirring in the ice bath for one hour, removed and stirred a further 2.5 hours at room temperature. The phosgene, EtOAc, and toluene were removed by vacuum distillation, leaving monodispersed methyl hexaethylene glycol chloroformate as a clear, oily residue.

The monodispersed chloroformate was dissolved in 20 mL dry dichloromethane and placed under a dry, inert atmosphere. Triethylamine (0.94 mL, 0.68 g, 6.7 mmol) and then NHS (N-hydroxy succinimide, 0.82 g, 7.1 mmol) were added, and the reaction mixture was stirred at room temperature for 18 hours. The mixture was filtered through silica gel to remove the white precipitate and concentrated in vacuo. The residue was taken up in dichloromethane and washed twice with cold water, twice with 1 N HCl and once with brine. The organics were dried over $Na_2SO_4$, filtered and concentrated. Final purification was done via flash chromatography (silica gel, EtOAc) to obtain the activated monodispersed hexaethylene monomethyl ether.

Example 9

Synthesis of Activated Heptaethylene Glycol Monomethyl Ether

8-Methoxy-1-(methylsulfonyl)oxy-3,6-dioxaoctane (29). A solution of monodispersed triethylene glycol monomethyl ether molecules (4.00 mL, 4.19 g, 25.5 mmol) and triethylamine (4.26 mL, 3.09 g, 30.6 mmol) in dry dichloromethane (50 mL) was chilled in an ice bath and place under a nitrogen atmosphere. A solution of methanesulfonyl chloride (2.37 mL, 3.51 g, 30.6 mmol) in dry dichloromethane (20 mL) was added dropwise from an addition funnel. Ten minutes after the completion of the chloride addition, the reaction mixture was removed from the ice bath and allowed to come to room temperature. The mixture was stirred for an additional hour, at which time TLC ($CHCl_3$ with 15% MeOH as the elutant) showed no remaining triethylene glycol monomethyl ether.

The reaction mixture was diluted with another 75 mL of dichloromethane and washed successively with saturated $NaHCO_3$, water and brine. The organics were dried over $Na_2SO_4$, filtered and concentrated in vacuo to give a monodispersed mixture of compound 29 as a clear oil (5.31 g, 86%).

Heptaethylene glycol mono methyl ether (30). To a stirred solution of monodispersed tetraethylene glycol (35.7 mmol) in dry DMF (25.7 mL), under $N_2$ was added in portion a 60% dispersion of NaH in mineral oil, and the mixture was stirred at room temperature for 1 hour. To the resulting sodium salt of the tetraethylene glycol was added a solution of monodispersed mesylate 29 (23.36) in dry DMF (4 ml) in a single portion, and the mixture was stirred at room temperature for 3.5 hours. Progress of the reaction was monitored by TLC (12% $CH_3OH$—$CHCl_3$). The reaction mixture was diluted with an equal amount of 1N HCl, and extracted with ethyl acetate (2×20 ml) and discarded. Extraction of aqueous solution and work-up gave monodispersed heptaethylene glycol monomethyl ether 30 (82-84% yield). Oil; Rf 0.46 (methanol: chloroform=3:22); MS m/z calc'd for $C_{15}H_{32}O_8$ 340.21 ($M^++1$), found 341.2.

Activation of heptaethylene glycol monomethyl ether. Monodispersed heptaethylene glycol monomethyl ether 30 is activated by a procedure as described herein to activate triethylene glycol monomethyl ether to provide the activated heptaethylene glycol monomethyl ether.

Example 10

Synthesis of Activated Decaethylene Glycol Monomethyl Ether (33)

20-methoxy-1-(methylsulfonyl)oxy-3,6,9,12,15,18-hexaoxaeicosane (31). Monodispersed compound 31 was obtained in quantitative yield from compound 30 and methanesulfonyl chloride as described for 29 herein, as an oil; Rf 0.4 (ethyl acetate acetonitrile=1:5); MS m/z calc'd for $C_{17}H_{37}O_{10}$ 433.21 ($M^++1$), found 433.469.

Decaethylene glycol monomethyl ether (32). Monodispersed compound 32 was prepared from compound 31 and monodispersed triethylene glycol using the procedure described herein. Oil; Rf 0.41 (methanol: chloroform=6:10); MS m/z calc'd for $C_{21}H_{44}O_{11}$ 472.29 ($M^++1$), found 472.29.

Activation of decaethylene glycol monomethyl ether. Monodispersed decaethylene glycol monomethyl ether 32 is activated by a procedure as described herein to activate triethylene glycol monomethyl ether to provide the activated decaethylene glycol monomethyl ether 33.

Example 11

HIM2 Oral Liquid Process

A general procedure to manufacture an oral liquid pharmaceutical composition of the present invention is shown below: The process involves making a premix without the drug, filtering the premix, then adding the premix and drug solution together.

Quantitative Composition of HIM2 Oral Liquid, 6 mg/mL

| Excipient | Composition % w/v | mg/mL | Quantity per Batch (g) |
|---|---|---|---|
| HIM2 | 0.6 | 6 | 6.0[1] |
| Sodium Cholate | 3.0 | 30 | 30.0 |
| Oleic Acid, NF | 1.0 | 10 | 10.0 |
| Sucralose, 25% | 0.8 | 8 | 8.0 |
| Strawberry Flavor | 0.4 | 4 | 4.0 |
| Capric Acid | 0.5 | 5 | 5.0 |
| Lauric Acid | 0.5 | 5 | 5.0 |
| Citric Acid Anhydrous, USP | 6.72 | 67.2 | 67.2 |
| Trolamine, NF | 5.22 | 52.2 | 52.2 |
| Tromethamine, USP | 4.24 | 42.4 | 42.4 |
| Sodium Hydroxide, NF | 1.88 | 18.8 | 18.8 |
| Sodium Hydroxide, 5 N | QS | QS | QS |
| Hydrochloric Acid, 5 N | QS | QS | QS |
| Sterile Water for Irrigation, USP | QS | QS | QS |
| Total | 100% | 1.0 mL | 1077.4 g |

[1]Weight adjusted for protein content.

Preparation of Premix for HIM2 Oral Liquid

1. Add 94.3% of the tromethamine and the trolamine, citric acid and sodium hydroxide (NF) to 350 g sterile water for irrigation and stir until completely dissolved.

2. Moderately heat and maintain the temperature through steps 3 & 4, below.

3. Add the sodium cholate to step 2 and stir until dissolved.

4. Add the oleic acid, capric acid, lauric acid, sucralose solution and strawberry flavor to step 3 and stir until dissolved.

5. Adjust the temperature to approximately room temperature.

6. Adjust the pH of step 5, if necessary, to 7.8±0.1 using 5N sodium hydroxide or 5N hydrochloric acid.

7. QS to the pre-mix batch weight with sterile water for irrigation.

8. Filter the step 7 product.

Preparation of HIM2 Oral Liquid, 6 mg/mL

1. Dispense the required quantity of the Premix for HIM2 Oral Liquid and continue stirring while performing steps 2 through 4 below.

2. Add the remaining tromethamine to 140 g of the sterile water for irrigation and stir until dissolved.

3. Adjust the pH of step 2, if necessary, to 7.7±0.2 using 5N sodium hydroxide or 5N hydrochloric acid.

4. Filter the step 3 liquid.

5. Add all of the HIM2 to step 4 and stir until completely dissolved.

6. Add all of step 5 to step 1 and stir.

7. Adjust the temperature to approximately room temperature, if necessary

8. Adjust the pH of step 7, if necessary, to 7.6–7.9 using 5N sodium hydroxide or 5N hydrochloric acid.

Example 12

HIM2 Oral Tablet Process

A general procedure to manufacture an oral tablet formulation of the present invention is shown below: The process involves making a lyophilized powder, adding tableting excipients and compressing.

Quantitative Composition of HIM2 Oral Tablets, 10 mg

| Excipient | Quantity per Batch (g) |
|---|---|
| Lyo Portion | |
| HIM2 | 2.50[1] |
| Sodium Cholate | 30.0 |
| Oleic Acid, NF | 10.0 |
| Sucralose, 25% | 8.0 |
| Stawberry Flavor | 4.0 |
| Capric Acid | 5.0 |
| Lauric Acid | 5.0 |
| Citric Acid Anhydrous, USP | 67.2 |
| Trolamine, NF | 52.2 |
| Tromethamine, USP | 42.4 |
| Sodium Hydroxide, NF | 18.8 |
| Sodium Hydroxide, 5 N | QS |
| Hydrochloric Acid, 5 N | QS |
| Sterile Water for Irrigation, USP | QS |
| Total | 1077.4 g |
| Tablet Portion | |
| Lyo Portion | 127.6 |
| Citric Acid | 29, 7 |
| Sodium Citrate dihydrate | 84.2 |
| (tris(hydroxymethyl)aminomethane) | 106.7 |
| Microcrystilline Cellulose | 24.8 |
| Explotab | 9.4 |
| Total | 382.3 |

[1]Weight adjusted for protein content.

Procedure

1. Dispense the required ingredients with the exception of the Sterile Water for Irrigation, USP, 2. Dispense 1500 g of Sterile Water for Irrigation, USP, and add to the processing vessel above.

3. Add the following ingredients to step 2 and mix until dissolved completely:

a. all of the Sodium Cholate b. all of the Dibasic Sodium Phosphate Heptahydrate, USP 4. Add the following ingredients to step 3 and mix vigorously.

a. All of the Capric Acid b. All of the haiwie Lauric Acid c. All of the Sodium Hydroxide, NF (Note: Heat will be generated by the addition of Sodium Hydroxide, NF.)

5. Adjust the step 4 solution to a temperature between 45° C. and 50° C., and mix until a clear solution results.

6. Cool to room temperature and, if necessary, adjust the step 5 pH to 7.2–7.8 using Sodium Hydroxide, 1N, or Hydrochloric Acid, 1N.

7. Add all of the HIM2 PEG 7 to step 6 and mix vigorously until a clear solution results.

8. Determine the amount of additional Sterile Water for Irrigation, USP, to add (if necessary)

9. Lyophilize this solution until a white amorphous powder results.

10. Blend the lyo portion with the tableting excipients.

11. Compress on a tablet press to achieve desired size, shape and hardness.

Example 13

Liquid oral pharmaceutical compositions formulated as described herein were administered to male CF-1 mice (~20–25 g). The animals were fasted overnight and deprived of food during the experiment. Water was provided ad libitum. The mice were maintained in cages with 5 animals per cage and kept in a room with a 12:12 L:D cycle (6:00 a.m.–6:00 p.m.). The mice were tested in groups of 5 animals per dose. Each group of mice (N=5) received either insulin conjugate-075, insulin conjugate-076, insulin-conjugate-084, insulin-conjugate-098, insulin-conjugate-101, insulin conjugate-106 or HIM2 orally at 1.25 and 2.5 mg/kg.

Figure 7:
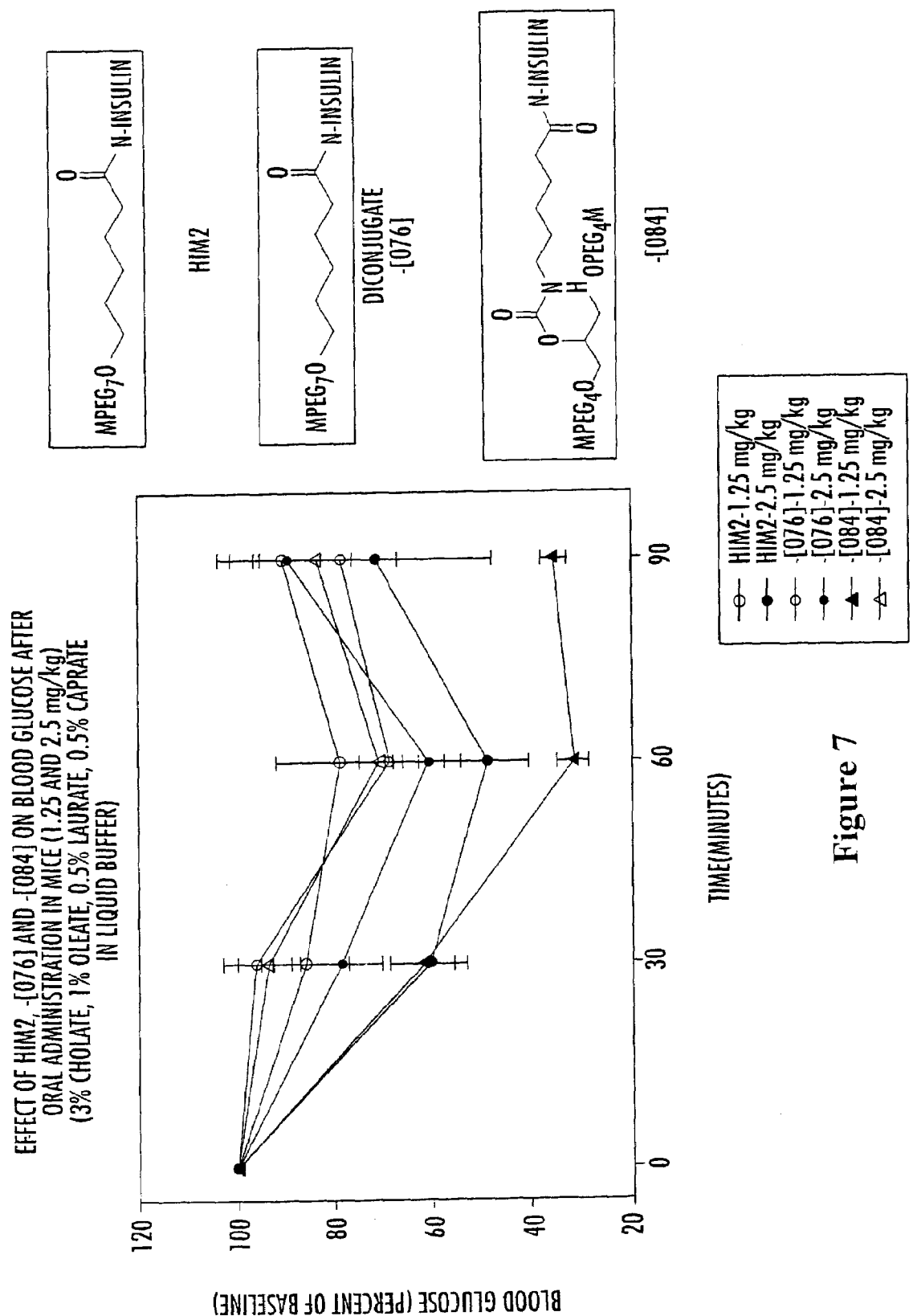
FIG. 7 illustrates a blood glucose vs. time curve resulting from oral administration of embodiments of the present invention in mice.
Figure 8:
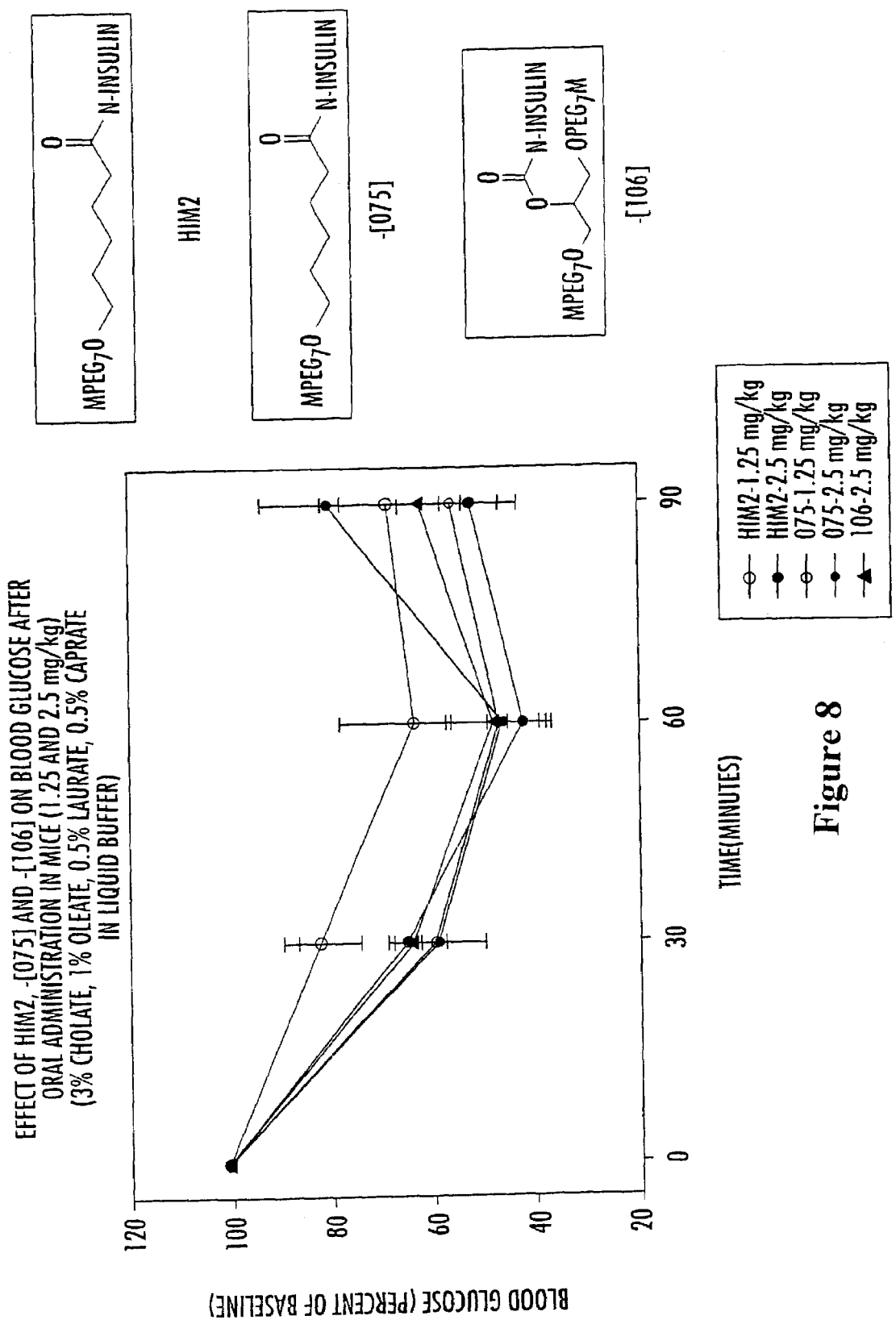
FIG. 8 illustrates a blood glucose vs. time curve resulting from oral administration of embodiments of the present invention in mice.
Figure 9:
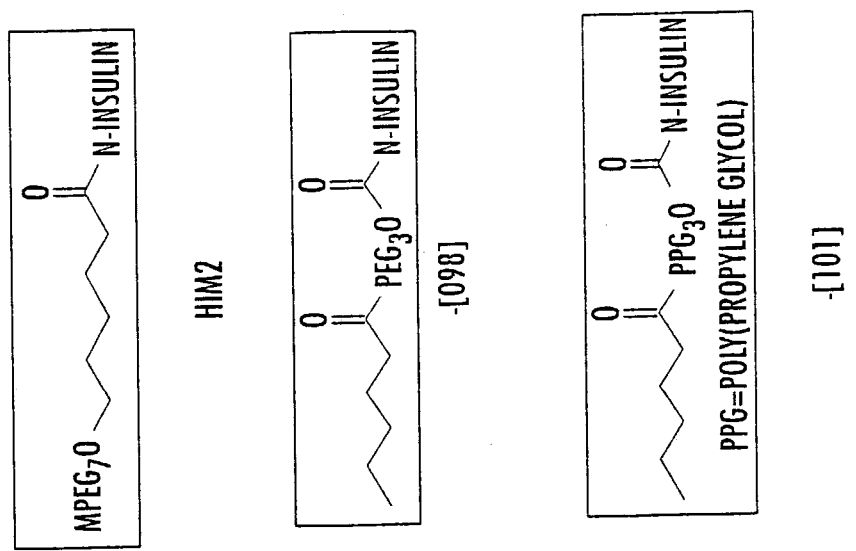
FIG. 9 illustrates a blood glucose vs. time curve resulting from oral administration of embodiments of the present invention in mice.
Figure 9:
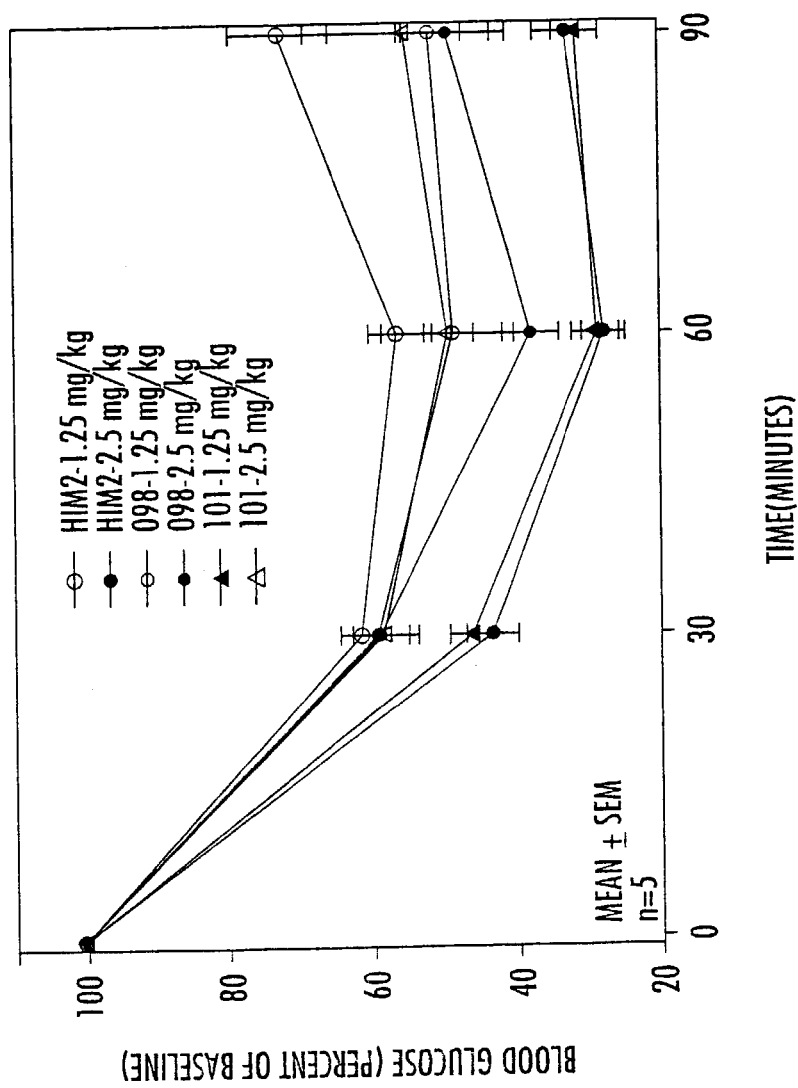

The insulin conjugates and HIM2 were provided at concentrations of 0.125 and 0.25 mg/ml. The dosing volume was 10.0 mL/kg. Total doses (each compound) the animals received were 1.25 and 2.5 mg/kg. Oral doses were administered using a gavaging needle (Popper gavage needle for mice #20; 5 cm from hub to bevel). The effect of the various conjugates on blood glucose level is illustrated in FIGS. 7, 8, and 9.

Example 14

Liquid oral pharmaceutical compositions formulated as described herein were administered to healthy human volunteers in a 4-way crossover study both pre-prandial and post-prandial. The insulin conjugate HIM2 was provided at concentrations of 0.125, 0.25 and 0.5 mg/ml and these were compared to baseline values where no dosing occurred. 20 mL oral doses were provided, followed by 70 mL of water.

Figure 2:
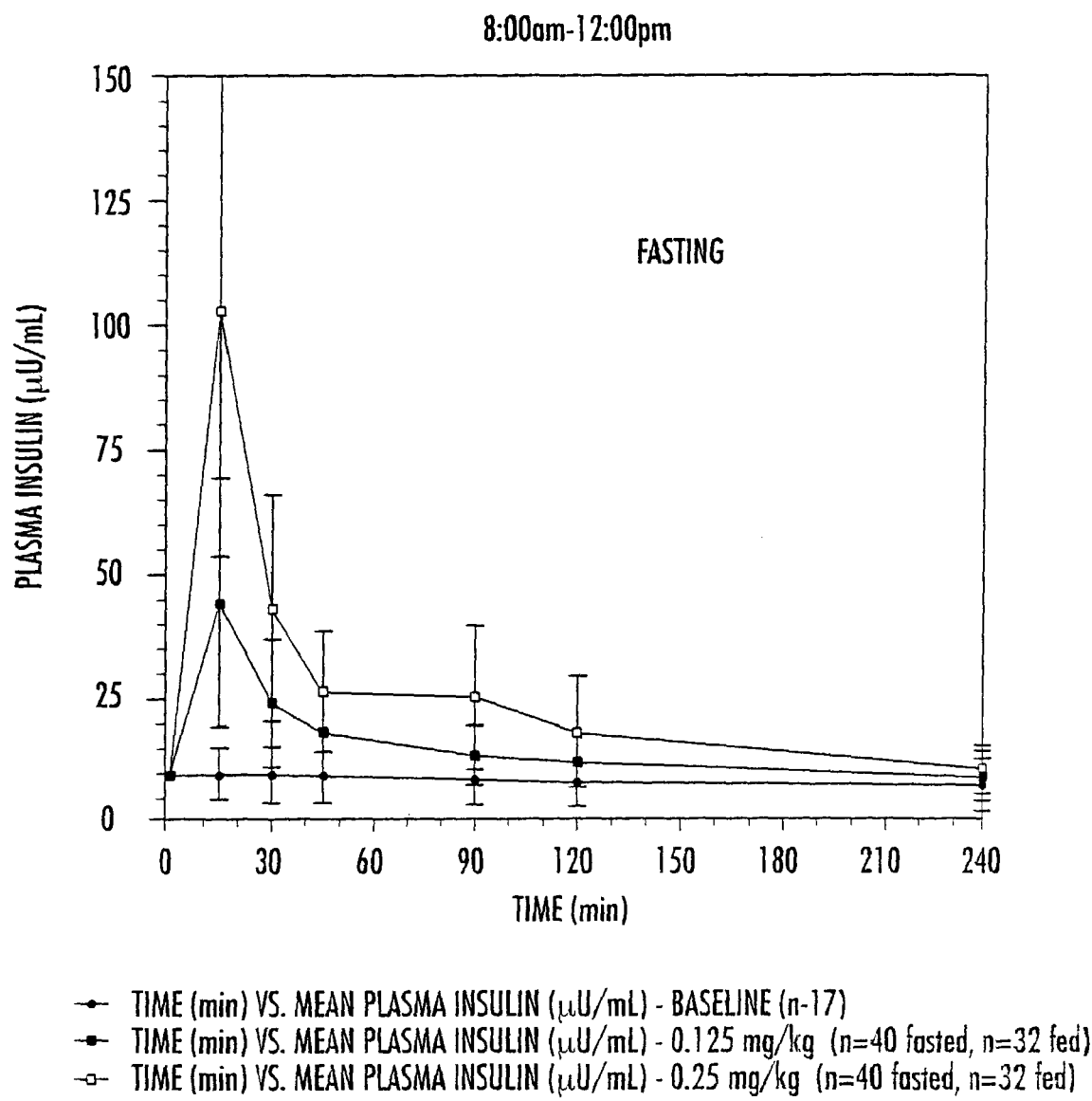
FIG. 2 illustrates a comparison of mean plasma insulin vs. time curve resulting from oral administration of various doses of embodiments of the present invention in fasting, non-diabetic subjects compared with a mean plasma insulin vs. time curve for baseline plasma insulin.
Figure 3:
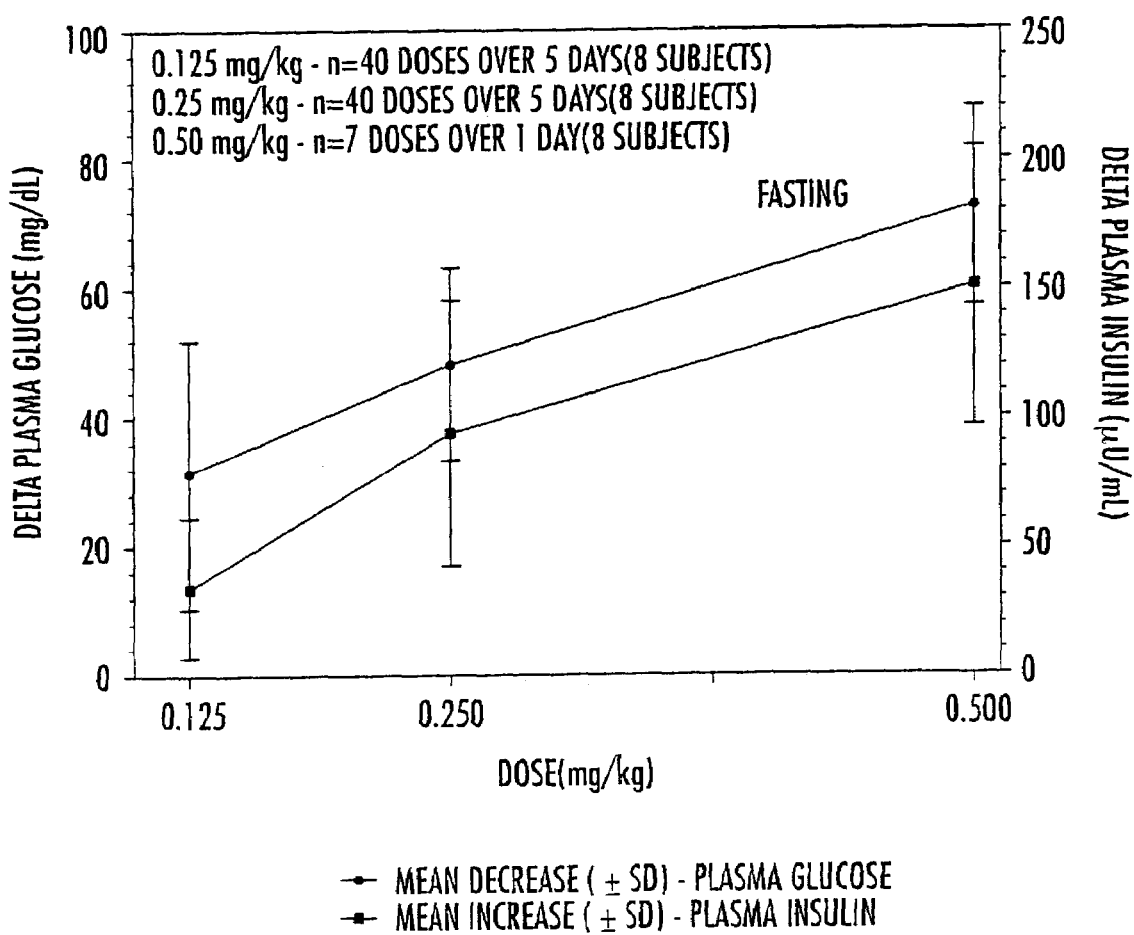
FIG. 3 illustrates glucose and insulin dose responses resulting from oral administration of embodiments of the present invention in fasting, non-diabetic subjects.

For the pre-prandial phase (fasted), subjects were fasted overnight and a single dose was administered in the morning. If blood glucose levels fell below 50 mg/dL, the subjects were rescued with a dextrose infusion. The effect of the conjugate HIM2 on blood glucose levels is illustrated in FIG. 1. HIM2 plasma levels (expressed in insulin equivalents) are shown in FIG. 2. The glucose/dose response and HIM2/dose response is shown in FIG. 3.

Figure 4:
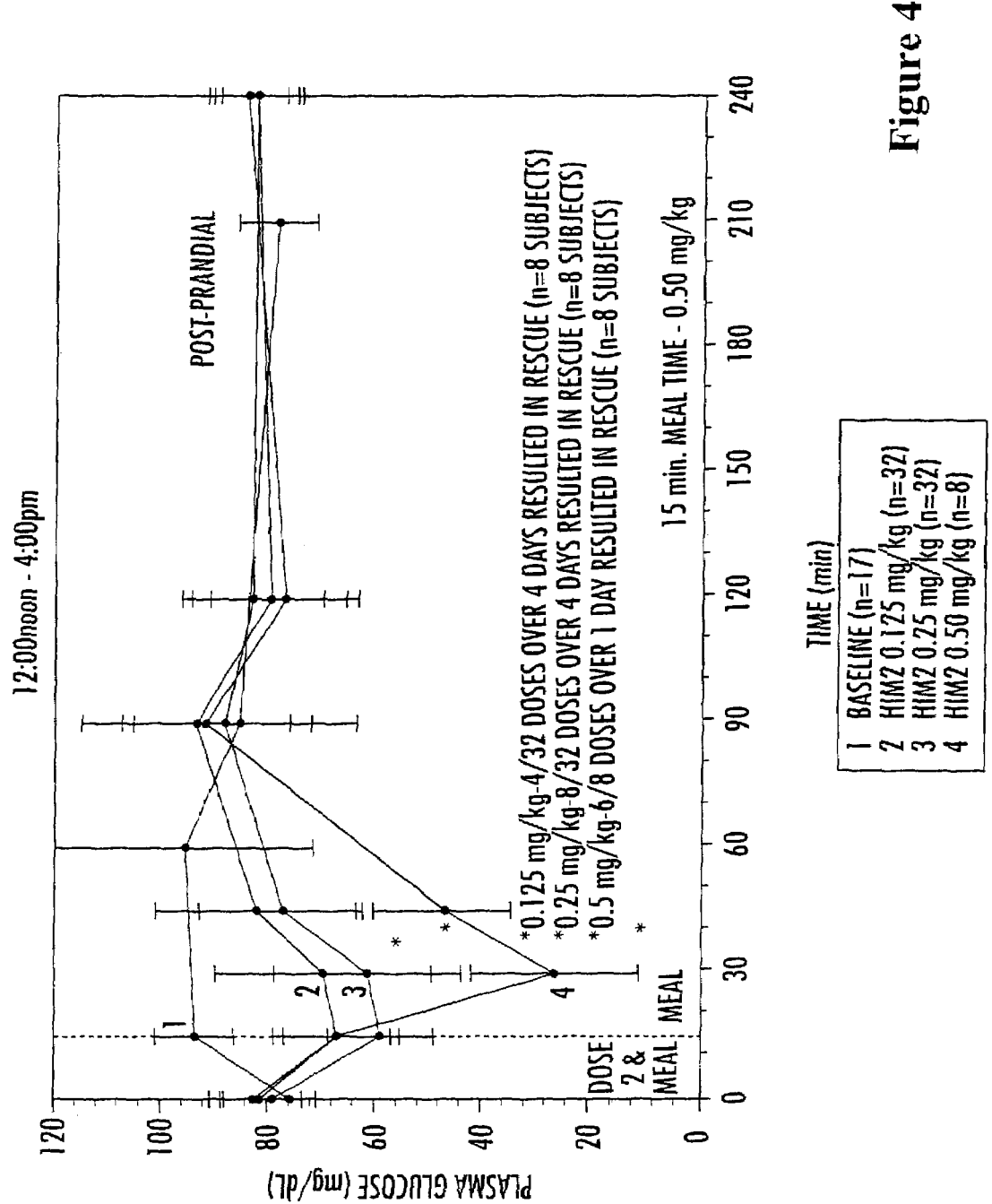
FIG. 4 illustrates a comparison of mean plasma glucose vs. time curves resulting from post-prandial, oral administration of various doses of embodiments of the present invention in non-diabetic subjects compared with a mean plasma glucose vs. time curve for baseline plasma glucose.
Figure 5:
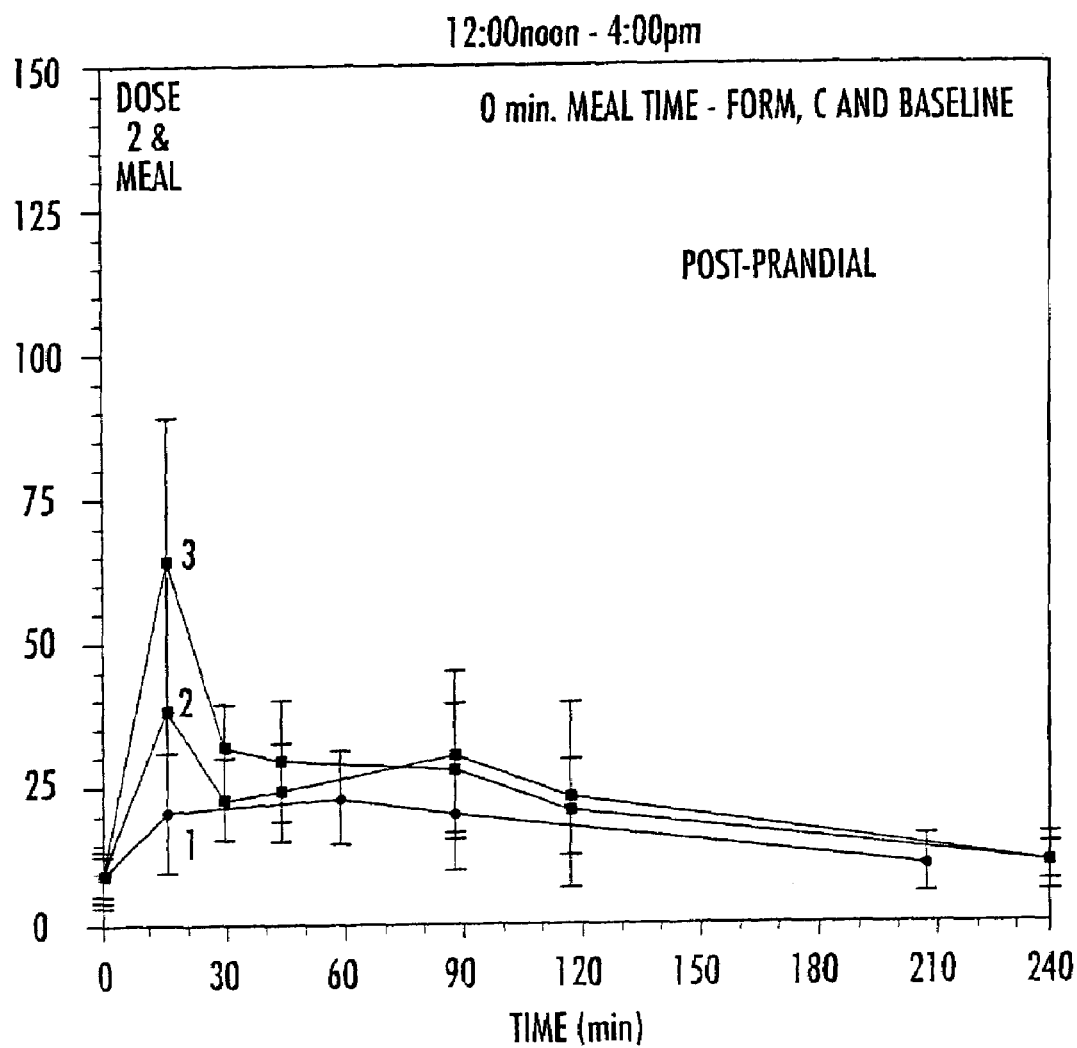
FIG. 5 illustrates a comparison of mean plasma insulin vs. time curve resulting from post-prandial, oral administration of various doses of embodiments of the present invention in non-diabetic subjects compared with a mean plasma insulin vs. time curve for baseline plasma insulin.
Figure 6:
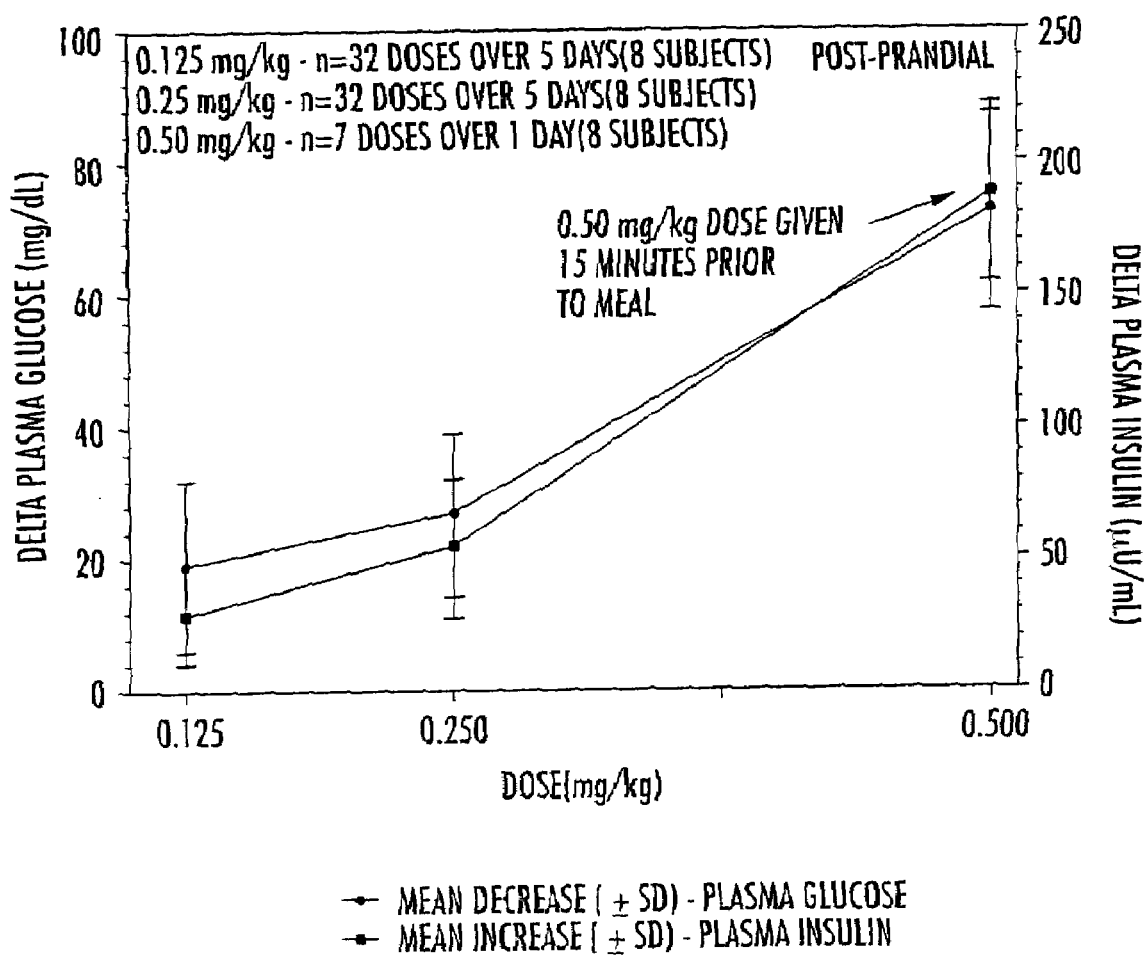
FIG. 6 illustrates glucose and insulin dose responses resulting from post-prandial oral administration of embodiments of the present invention in non-diabetic subjects.

For the post-prandial phase (fed), subjects received a single dose followed 15 minutes later by a meal. If blood glucose levels fell below 50 mg/dL, the subjects were rescued with a dextrose infusion. The effect of the conjugate HIM2 on blood glucose levels is illustrated in FIG. 4. HIM2 plasma levels (expressed in insulin equivalents) are shown in FIG. 5. The glucose/dose response and HIM2/dose response is shown in FIG. 6.

Example 15

Preparation of Formulations. Bile salts, sodium phosphate, and HIM2 were dissolved in purified water and adjusted to pH 7.8.

Mouse Model. CF1 mice of 20 to 25 g were administered intragastric boluses of 10 mL/kg of formulations containing 1.0 mg/mL HIM2 and sodium taurocholate or sodium taurodeoxycholate (5% bile salt and 1.5% bile salt) or formulations containing 0.5 mg/mL HIM2 and sodium glyocholate or sodium ursodeoxycholate (0.15% bile salt, 0.5% bile salt, 1.5% bile salt or 5% bile salt). Blood glucose was measured prior to and 60 minutes after dosing. Results are expressed as the ratio of 60 and 0 minute tail artery blood glucometer readings.

Dog Model. Adult male beagle dogs were fasted overnight. Oral doses of 0.2 mL/kg of formulations containing 5 mg/mL HIM2 (1 mg/kg) and various levels (0.15%, 0.5%, 1.5%; 5%, 10%) of four different bile salts (TDc, DC, UDC, cholate) were followed by a water chaser of 1.0 mL/kg. Blood was sampled prior to and 15, 30, 60, and 120 minutes after dosing.

Calculation of Glucose Area Over the Curve (AOC). AOC was calculated by the trapezoid rule as the integral of percent blood glucose drop with time.

Figure 10:
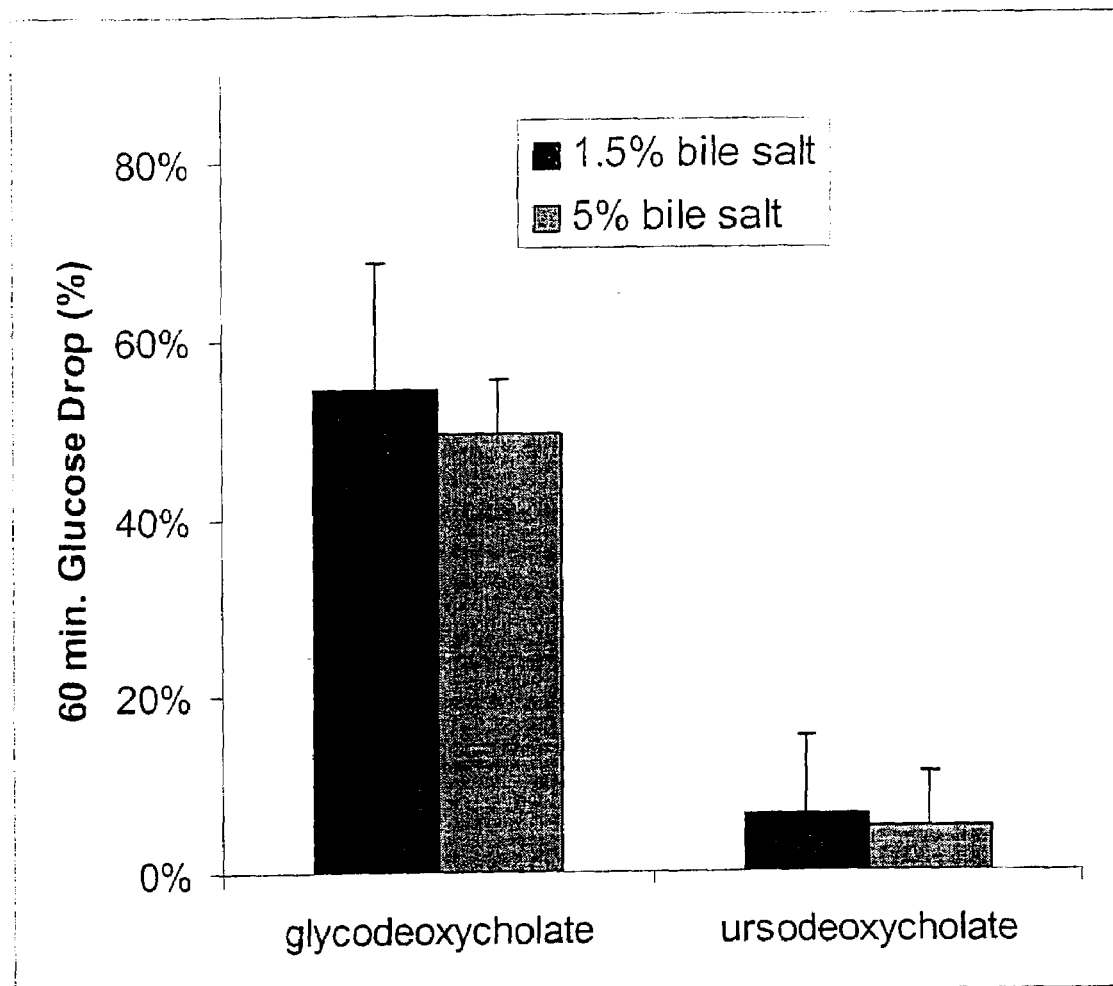
FIG. 10 illustrates a comparison of the percent drop in glucose over 60 minutes after administration of an intragastric bolus of 10 mL/kg of embodiments of the present invention in mice (error bars represent standard error (n=5))
Figure 11:
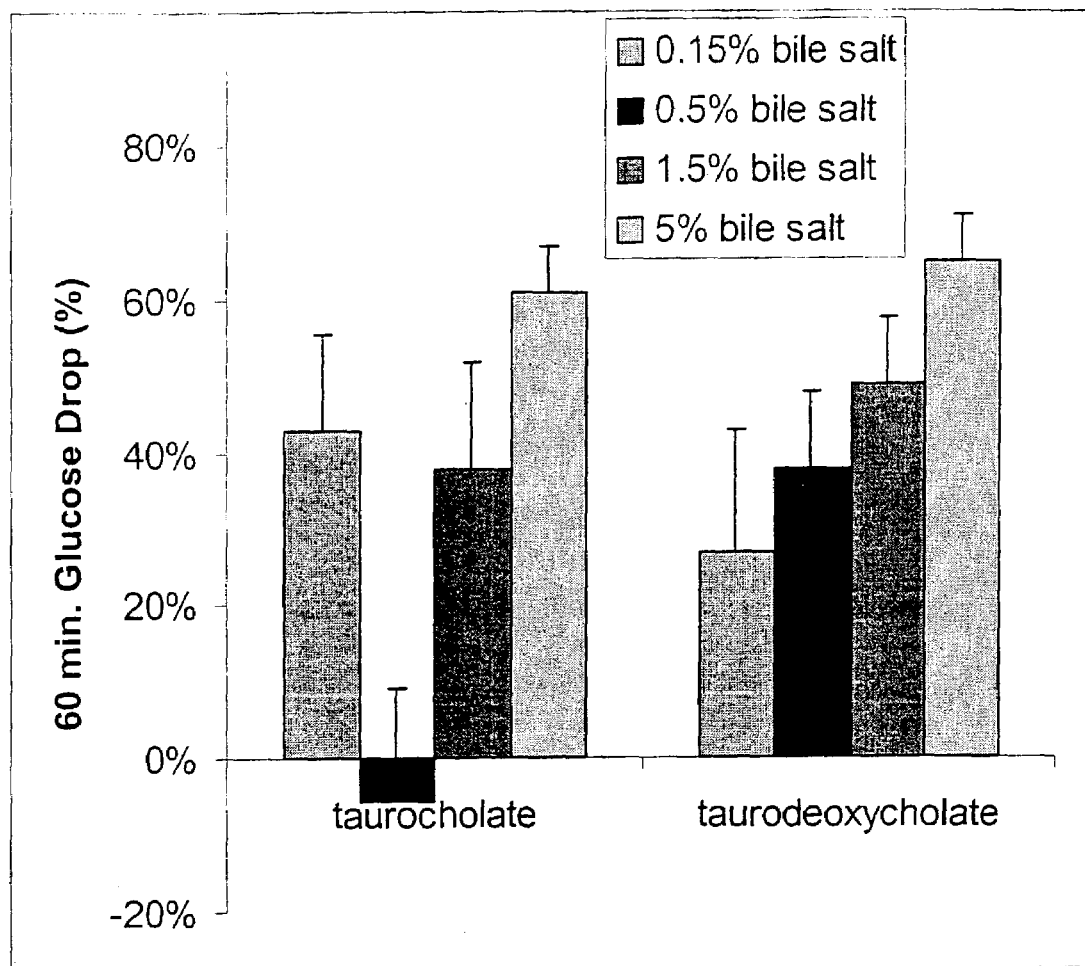
FIG. 11 illustrates a comparison of the percent drop in glucose over 60 minutes after administration of an intragastric bolus of 10 mL/kg of embodiments of the present invention in mice (error bars represent standard error (n=5))
Figure 12:
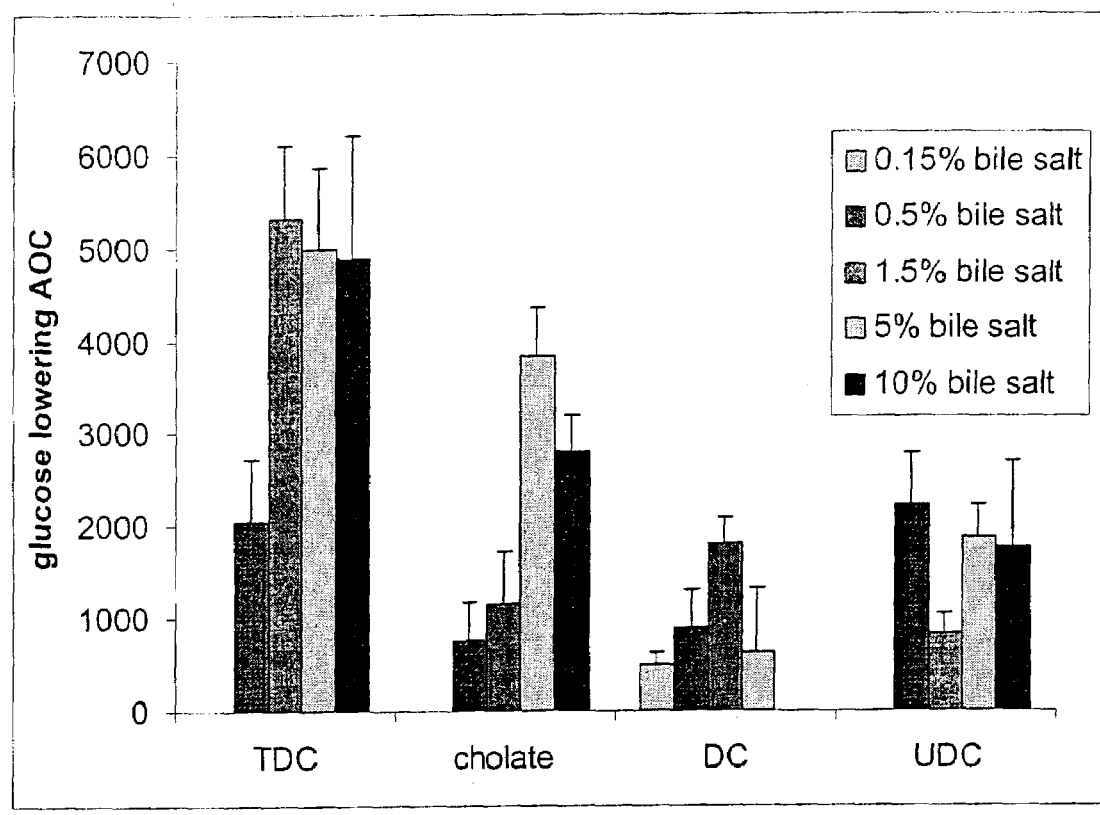
FIG. 12 illustrates a comparison of glucose lowering in dogs, calculated as Area Over the Curve (AOC), after administration of an oral dose of 0.2 mL/kg of embodiments of the present invention followed by a water chaser of 1.0 mL/kg. TDC=taurodeoxycholate, DC=deoxycholate, UDC=ursodeoxycholate.

Results of administering HIM2 in bile salt solutions to mice are shown in FIGS. 10 and 11. Dog study results are given in FIG. 12. In almost all cases, substantial reductions in blood glucose were observed as the result of co-administration of HIM2 and bile salts.

Similar levels of glucose reduction were observed in mice when HIM2 was administered with taurocholate, taurodeoxycholate or glycodeoxycholate (FIGS. 10 and 11). Ursodeoxycholate was significantly less effective than glycodeoxycholate ($p<0.05$).

In dogs a clear response to different bile salt levels was observed. For example, blood glucose Area Over the Curve (AOC) values were significantly higher ($p<0.05$) for HIM2 in 5% sodium cholate than for HIM2 in 0.5% or 1.5% sodium cholate. Likewise deoxycholate was significantly more effective at 1.5% than at 0.15% and taurodeoxycholate was more effective at 1.5% than at 0.5%. Ursodeoxycholate was the only bile salt that did not show a significant concentration effect in dogs.

All of the bile salts were effective at a level of 1.5%. This corresponds to about 500 micromoles per dose, or about 2% of mean daily bile salt secretion for non-obese humans (Reuben et al. 1985. "Bile salt secretion in obese and on-obese individuals with and without gallstones" *Clin. Sci.* (Lond.) 69(1)"71-9). Thus, absorption of HIM2 is enhanced using bile salts at levels that represent a small fraction of physiological secretion.

Example 16

A single-centered, randomized, open-label, 2-way crossover study on Hexyl-Insulin Monoconjugate 2 (HIM2) and regular recombinant insulin was conducted. The drug compounds were administered orally in liquid formulation according to example 11 to healthy adult subjects. Each subject received a dose that was prepared individually to account for that subject's body weight and for the dose that subject was to receive. The 6 mg/mL concentrate prepared in example 11 was mixed with a matching diluent to deliver the desired dose (0.06 mg/kg or 0.125 mg/kg or 0.25 mg/kg of HIM2 or regular insulin) in 20 mL of the mixture.

Twelve subjects were fasted overnight and given a single dose in the morning. Blood samples were collected at 0, 10, 15, 20, 30, 45, 90, 120, and 240 minutes post-dose while the subjects remained in the fasted state. Plasma insulin concentrations and plasma glucose concentrations were determined for each subject.

Figure 13:
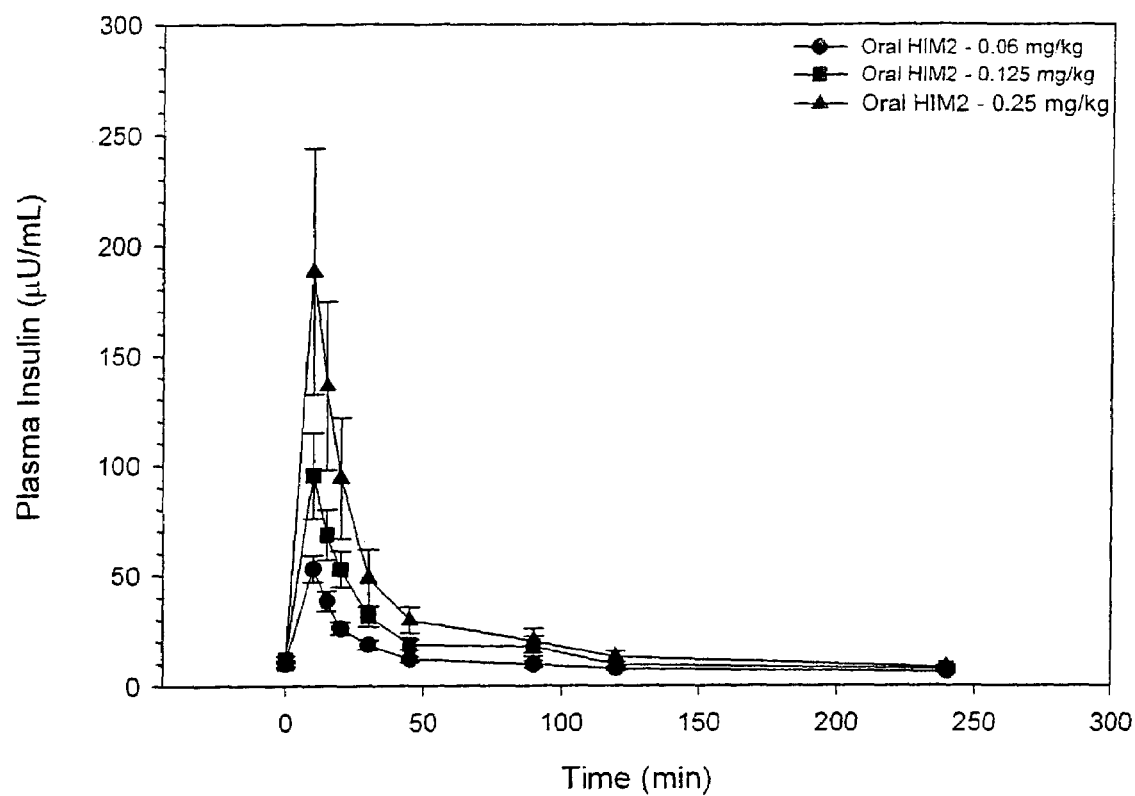
FIG. 13 illustrates a plasma insulin versus time curve resulting from oral administration of a composition of this invention comprising HIM2 to humans.
Figure 14:
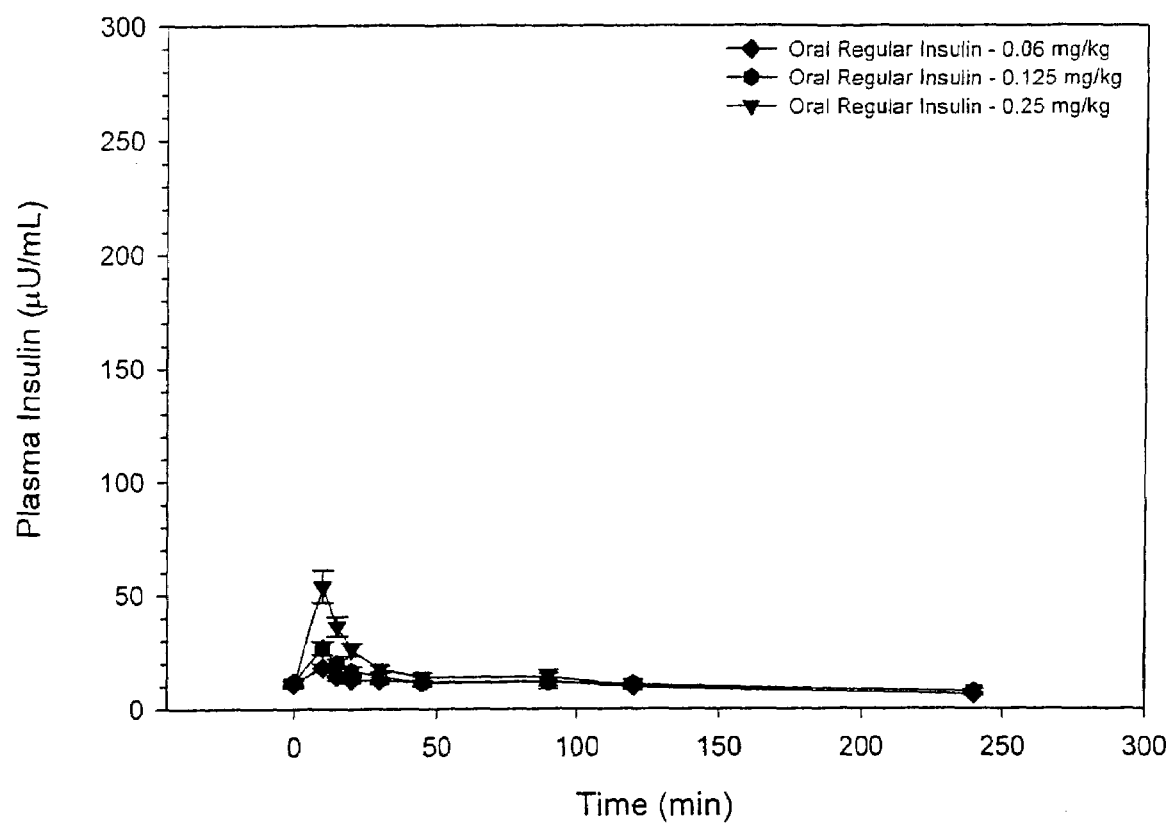
FIG. 14 illustrates a plasma insulin versus time curve resulting from oral administration of a composition of this invention comprising recombinant insulin to humans.

As shown in FIGS. 13 and 14, HIM2 and regular insulin delivered with the formulation at the doses used were orally available in a dose dependent manner. The higher plasma levels achieved with HIM2 are due to the enzymatic protection provided by the conjugation with an oligomer and to the longer circulating half life of the HIM2 molecule compared to the native insulin molecule.

| HIM2 Excipients details | |
|---|---|
| Excipient | Amount |
| Capric Acid | 51.77 |
| Croscarmellose Sodium | 30 |
| Insulin as Protein | 6.5 |
| Lauric Acid | 51.77 |
| Magnesium Stearate | 6 |
| Mannitol | 257.5 |
| Sodium Cholate | 155.31 |
| Sodium Hydroxide Pellets | 19.67 |
| Sodium Phosphate Monobasic Monohydrate | 21.48 |

Four adult, male Beagle dogs with body weights in the range 10–13 kg were fasted overnight. Tap water was available ad libitum (except for a period of no water for 2 hours pre-dosing until 1 hour post dosing). An assessment of hypoglycemia post-dosing was done.

Each tablet contained 6.5 mg of HIM2 in the excipient described above to achieve a target dose of ~0.5 mg/kg. Doses were administered by placing to the back of the throat. Immediately following the administration of the test article, the animals were given 1 ml/kg of tap water to the back of the throat using an appropriate-sized syringe.

Approximately 2.5 ml of blood was collected from the jugular vein in heparin-containing tubes from all animals immediately prior to the dose, and at 15, 30, 60 and 120 minutes post-dosing. The samples were mixed immediately by inverting, placed on a rocker and then centrifuged. An aliquot of plasma (0.75 ml) was frozen at −20° C. for subsequent analysis of insulin concentration.

Figure 15:
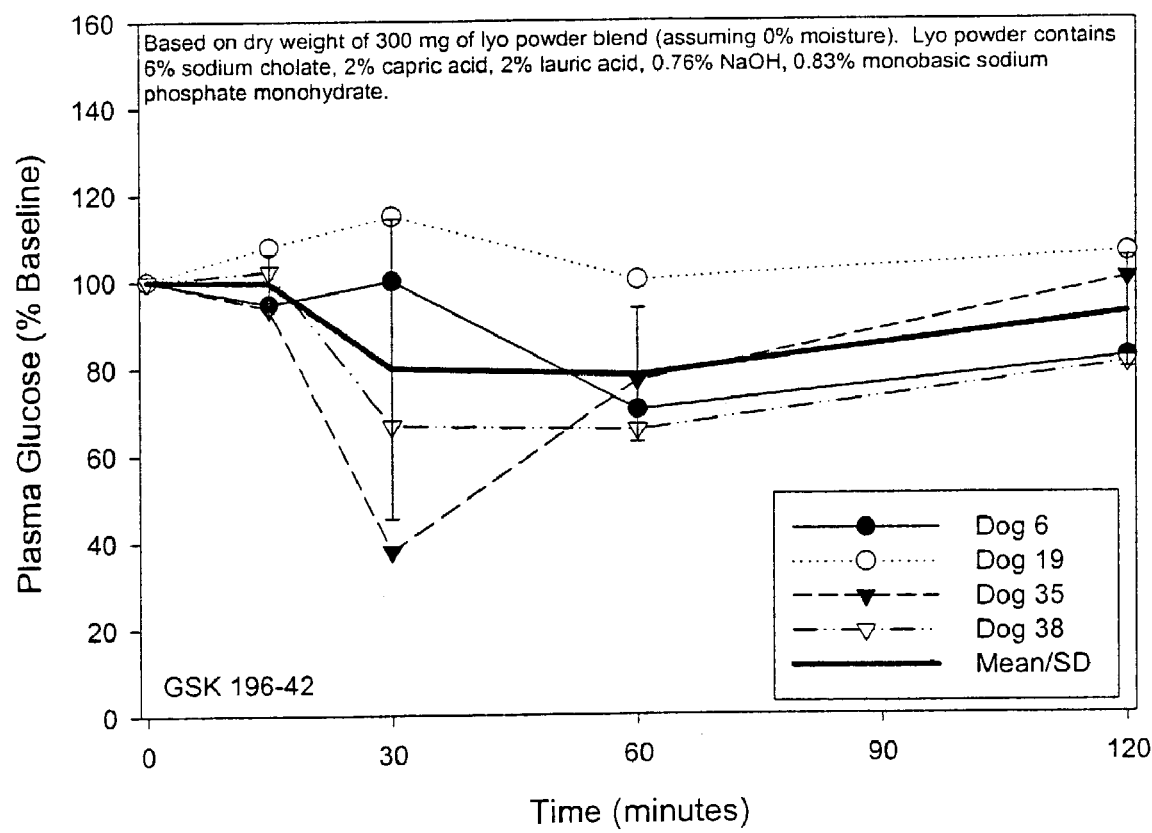
FIG. 15 illustrates a plasma glucose versus time curve resulting from oral administration of the embodiments of this invention to dogs.

The glucose-lowering effect of an uncoated tablet formulation was measured in fasted beagle dogs after oral dosing with one tablet that provided about 0.50 mg/kg of native insulin (FIG. 15) and pharmacodynamic effects were demonstrated.

The present invention has been described herein with reference to various embodiments. These embodiments do not serve to limit the invention, but are set forth for illustrative purposes. The scope of the invention is defined by the claims that follow.

That which is claimed is:

1. A pharmaceutical composition consisting of (a) an insulin drug-oligomer conjugate comprising an insulin drug covalently coupled to an oligomeric moiety, wherein the oligomeric moiety is polyethylene glycol, (b) a bile salt, and (c) a pharmaceutically acceptable carrier.

2. A pharmaceutical composition comprising (a) an insulin drug-oligomer conjugate comprising an insulin drug covalently coupled to an oligomeric moiety, wherein the oligomeric moiety is alkane, (b) a bile salt, and (c) a pharmaceutically acceptable carrier.

3. A pharmaceutical composition comprising:
insulin;
a bile salt; and
a fatty acid, wherein the fatty acid is present in an amount wherein the solubility of the bile salt in the presence of the fatty acid is greater than the solubiity of the bile salt in a corresponding composition lacking the fatty acid, wherein the bile salt is cholate and the cholate is present in the amount of about 1.5% weight/volume and the fatty acid is laurate and the laurate is present in the amount of 2% weight/volume.

4. The pharmaceutical composition of claim 3, wherein the fatty acid component and the bile salt component are present in a weight to weight ratio of between 1:4 and 1:1.

5. The pharmaceutical composition of claim 3, wherein the fatty acid component comprises one or more fatty acids in the range of $C_4$ to $C_{20}$.

6. The pharmaceutical composition of claim 3, wherein the fatty acid is selected from the group consisting of lauric acid, capric acid, oleic acid and mixtures thereof.

7. The pharmaceutical composition of claim 3, wherein the pH of the composition is between 6.2 and 9.0.

8. The pharmaceutical composition of claim 3, further comprising a buffering component.

9. The pharmaceutical composition of claim 3, wherein the pharmaceutical composition is a liquid pharmaceutical composition.

10. The pharmaceutical composition of claim 9, wherein the liquid pharmaceutical composition is suitable for oral administration.

11. The pharmaceutical composition of claim 3, wherein the composition is suitable for a route of administration selected from the group consisting of buccal, transdermal, peroral and nasal administration.

12. The pharmaceutical composition of claim 9, wherein the liquid pharmaceutical composition is suitable for parenteral administration.

13. The pharmaceutical composition of claim 3, wherein the pharmaceutical composition is a solid dosage pharmaceutical composition.

14. The pharmaceutical composition of claim 3, wherein the insulin is an insulin polypeptide.

15. The pharmaceutical composition of claim 14, wherein the insulin polypeptide is human insulin.

16. The pharmaceutical composition of claim 14, wherein the insulin polypeptide is an insulin analog selected from the group consisting of $Gly^{A21}$ insulin, human; $Gly^{A21}$ $Gln^{B3}$ insulin, human; $Ala^{A21}$ insulin, human; $Ala^{A21}$ $Gln^{B3}$ insulin, human; $Gln^{B3}$ insulin, human; $Gln^{B30}$ insulin, human; $Gly^{A21}$ $Glu^{B30}$ insulin, human; $Gly^{A21}$ $Gln^{B3}$ $Gln^{B30}$ insulin, human; $Gln^{B3}$ $Glu^{B30}$ insulin, human; $Asp^{B28}$ insulin, human; $Lys^{B28}$ insulin, human; $Leu^{B28}$ insulin, human; $Val^{B28}$ insulin, human; $Ala^{B28}$ insulin, human; $Asp^{b28}$ $Pro^{B29}$ insulin, human; $Lys^{B28}$ $Pro^{B29}$ insulin, human; $Leu^{B28}$ $Pro^{B29}$ insulin, human; $Val^{B28}$ $Pro^{B29}$ insulin, human; and $Ala^{B28}$ $Pro^{B29}$ insulin, human.

17. The pharmaceutical composition of claim 3, wherein the fatty acid further comprises caprate.

18. A method of treating an insulin deficiency in a subject in need of such treatment, said method comprising administering to the subject a therapeutically effective amount of a pharmaceutical composition comprising (a) an insulin drug-oligomer conjugate comprising an insulin drug covalently coupled to an oligomeric moiety wherein the oligomeric moiety is lipophilic, (b) a bile salt, and (c) a pharmaceutically acceptable carrier, wherein the oligomeric moiety is alkane.

19. A method of treating an insulin deficiency in a subject in need of such treatment, said method comprising administering to the subject a therapeutically effective amount of the pharmaceutical composition of claim 3.

20. The method of claim 19, wherein the fatty acid component and the bile salt component are present in a weight ratio of between 1:4 and 1:1.

21. The method of claim 19, wherein the fatty acid component comprises one or more fatty acids in the range of $C_4$ to $C_{20}$.

22. The method of claim 19, wherein the fatty acid is selected from the group consisting of lauric acid, capric acid, oleic acid and mixtures thereof.

23. The method of claim 19, wherein the pH of the composition is between 6.2 and 9.0.

24. The method of claim 19, further comprising a buffering component.

25. The method of claim 19, wherein the pharmaceutical composition is a liquid pharmaceutical composition.

26. The method of claim 19, wherein the pharmaceutical composition is a solid dosage pharmaceutical composition.

27. The method of claim 19, wherein the method comprises orally administering the pharmaceutical composition to the subject.

28. The method of claim 19, wherein the method comprises administering the pharmaceutical composition to the subject by an administration route selected from the group consisting of buccal, transdermal, peroral and nasal administration.

29. The method of claim 19, wherein the insulin is an insulin polypeptide.

30. The method of claim 29, wherein the insulin polypeptide is human insulin.

31. The method of claim 29, wherein the insulin polypeptide is an insulin analog selected from the group consisting of Gly$^{A21}$ insulin, human; Gly$^{A21}$ Gln$^{B3}$ insulin, human; Ala$^{A21}$ insulin, human; Ala$^{A21}$ Gln$^{B3}$ insulin, human; Gln$^{B3}$ insulin, human; Gln$^{B30}$ insulin, human; Gly$^{A21}$ Glu$^{B30}$ insulin, human; Gly$^{A21}$ Gln$^{B3}$ Glu$^{B30}$ insulin, human; Gln$^{B3}$ Glu$^{B30}$ insulin, human; Asp$^{B28}$ insulin, human; Lys$^{B28}$ insulin, human; Leu$^{B28}$ insulin, human; Val$^{B28}$ insulin, human; Ala$^{B28}$ insulin, human; Asp$^{B28}$ Pro$^{B29}$ insulin, human; Lys$^{B21}$ Pro$^{B29}$ insulin, human; Leu$^{B28}$Pro$^{B29}$ insulin, human; Val$^{B28}$ Pro$^{B29}$ insulin, human; and Ala$^{B28}$ Pro$^{B29}$ insulin, human.

32. The pharmaceutical composition of claim 4, wherein the fatty acid component and the bile salt component are present in a weight to weight ratio of between 1:3 and 1:2.

33. The method of claim 20, wherein the fatty acid component and the bile salt component are present in a weight ratio of between 1:3 and 1:2.

34. A method of treating an insulin deficiency in a subject in need of such treatment, comprising administering to the subject a therapeutically effective amount of the pharmaceutical composition comprising (a) insulin drug-oligomer conjugate comprising an insulin drug covalently coupled to an oligomeric moiety, (b) a bile salt, and (c) a pharmaceutically acceptable carrier, by nasally administering the pharmaceutical composition to the subject.

* * * * *

UNITED STATES PATENT AND TRADEMARK OFFICE
CERTIFICATE OF CORRECTION

PATENT NO. : 7,196,059 B2  
APPLICATION NO. : 10/382155  
DATED : March 27, 2007  
INVENTOR(S) : Soltero et al.

Page 1 of 1

It is certified that error appears in the above-identified patent and that said Letters Patent is hereby corrected as shown below:

Column 27, Line 18: "hex acid" should be --hexanoic acid--

Column 27, Line 37: "hexan acid" should be --hexanoic acid--

Column 27, Line 48: "ethoxy}acid" should be --ethoxy}-hexanoic acid--

Column 34, Line 46: "ethyl acetate acetonitrile" should be --ethyl acetate : acetonitrile--

Column 36, Line 49: "the haiwie Lauric" should be --the Lauric--

Column 41, Line 25: "consisting" should be --consisting of--

Column 42, Line 7: "$Lys^{B21}$" should be --$Lys^{B28}$--

Signed and Sealed this

Thirtieth Day of October, 2007

JON W. DUDAS  
*Director of the United States Patent and Trademark Office*